(12) United States Patent
Metallo et al.

(10) Patent No.: US 8,637,556 B2
(45) Date of Patent: Jan. 28, 2014

(54) LINKED MYC-MAX SMALL MOLECULE INHIBITORS

(75) Inventors: Steven J. Metallo, Silver Spring, MD (US); Edward V. Prochownik, Pittsburgh, PA (US); Ariele Viacava Follis, Memphis, TN (US)

(73) Assignees: University of Pittsburgh—Of the Commonwealth System of Higher Education, Pittsburgh, PA (US); Georgetown University, Washington, DC (US)

( * ) Notice: Subject to any disclaimer, the term of this patent is extended or adjusted under 35 U.S.C. 154(b) by 0 days.

(21) Appl. No.: 13/144,674

(22) PCT Filed: Jan. 15, 2010

(86) PCT No.: PCT/US2010/021183
§ 371 (c)(1),
(2), (4) Date: Sep. 30, 2011

(87) PCT Pub. No.: WO2010/083404
PCT Pub. Date: Jul. 22, 2010

(65) Prior Publication Data
US 2012/0015989 A1 Jan. 19, 2012

Related U.S. Application Data

(60) Provisional application No. 61/205,208, filed on Jan. 16, 2009.

(51) Int. Cl.
*A61K 31/427* (2006.01)
*A61K 31/4245* (2006.01)
*C07D 277/04* (2006.01)
*C07D 413/02* (2006.01)

(52) U.S. Cl.
USPC ........... 514/364; 514/369; 548/126; 548/183; 435/375

(58) Field of Classification Search
USPC .......................... 514/364, 369; 548/126, 183
See application file for complete search history.

(56) References Cited

U.S. PATENT DOCUMENTS 7,026,343 B2    4/2006 Prochownik et al.
7,872,027 B2    1/2011 Metallo

OTHER PUBLICATIONS

Horig et al. Journal of Translational Medicine 2004, 2(44), p. 1-8.*
Schafer et al. Drug Discovery Today, 2008, 13 (21/22), 913-916.*
Drin et al., "Physico-chemistry requirements for cellular uptake of pAntp peptide. Role of lipid-binding affinity," *Eur J Biochem.* 268(5):1304-1314, Mar. 2001.
Follis et al., "Structural rationale for the coupled binding and unfolding of the c-Myc oncoprotein by small molecules," *Chem Biol.* 15(11):1149-1155, Nov. 24, 2008.
Guo et al., "Efficacy, pharmacokinetics, tissue distribution, and metabolism of the Myc-Max disruptor, 10058-F4 [Z,E]-5-[4-ethylbenzylidine]-2-thioxothiazolidin-4-one, in mice," *Cancer Chemother Pharmacol.* 63(4):615-625, Mar. 2009 (published online May 29, 2008).
Kolly et al., "Proliferation, cell cycle exit, and onset of terminal differentiation in cultured keratinocytes: pre-programmed pathways in control of C-Myc and Notch1 prevail over extracellular calcium signals," *J Invest Dermatol.* 124(5):1014-1025, May 2005.
Li et al., "A global transcriptional regulatory role for c-Myc in Burkitt's lymphoma cells," *PNAS USA* 100(14):8164-8169, Jul. 8, 2003 (available online Jun. 13, 2003).
Mo et al., "Identification of small molecules that induce apoptosis in a Myc-dependent manner and inhibit Myc-driven transformation," *PNAS USA* 103 16 :6344-6349, Apr. 18, 2006.
Mustata et al., "Discovery of novel Myc-Max heterodimer disruptors with a three-dimensional pharmacophore model," *J Med Chem.* 52(5):1247-1250, Mar. 12, 2009.
Wang et al., "Improved low molecular weight Myc-Max inhibitors," *Mol Cancer Ther.* 6(9):2399-2408, 2007.
Yin et al., "Low molecular weight inhibitors of Myc-Max interaction and function," *Oncogene* 22(40):6151-6159, Sep. 18, 2003.
International Search Report from International Application No. PCT/US2010/021183 dated Aug. 10, 2010.
Follis, "Small-molecule perturbation of competing interactions between c-Myc and Max," *Bioorganic & Medicinal Chemistry Letters* 19:807-810, 2009 (published online Dec. 10, 2008).
Gomez-Curet et al., "c-Myc inhibition negatively impacts lymphoma growth," *Journal of Pediatric Surgery* 41:207-211, 2006.
Hammoudeh et al., "Multiple Independent Binding Sites for Small-Molecule Inhibitors on the Oncoprotein c-Myc," *J. Am. Chem. Soc.* 131:7390-7401, 2009 (published online May 11, 2009).
Huang et al., "A small-molecule c-Myc inhibitor, 10058-F4, induces cell-cycle arrest, apoptosis, and myeloid differentiation of human acute myeloid leukemia," *Experimental Hematology* 34:1480-1489, 2006.
Kirk, "Selective Fluorination in Drug Design and Development: An Overview of Biochemical Rationales," *Current Topics in Medicinal Chemistry* 6(14):1447-1456, 2006.
Leglise et al., "Leukemic Cell Maturation: Phenotypic Variability and Oncogene Expression in HL60 Cells: A Review," *Blood Cells* 13:319-337, 1988.
Müller et al., "Fluorine in Pharmaceuticals: Looking Beyond Intuition," *Science* 317:1881-1886, Sep. 28, 2007.
Park et al., "Fluorescence Polarization Assay to Quantify Protein-Protein Interactions," *Methods in Molecular Biology* 261:161-166, 2004.
Summers et al., "Synthesis of Fluorescent Labeled Derivatives of Aminopropylpyrimidines," *J. Org. Chem.* 40(11)1559-1561, 1975.

* cited by examiner

*Primary Examiner* — Yong Chu
(74) *Attorney, Agent, or Firm* — Klarquist Sparkman LLP.

(57) ABSTRACT

Provided herein are compounds and compositions for interfering with the association of Myc and Max. These compounds and compositions are useful in methods for inhibiting growth or proliferation of a cell. Methods of inhibiting growth or proliferation of a cell comprise contacting the cell with an amount of a compound that interferes with Myc and Max association effective to inhibit growth or proliferation of the cell.

18 Claims, 33 Drawing Sheets

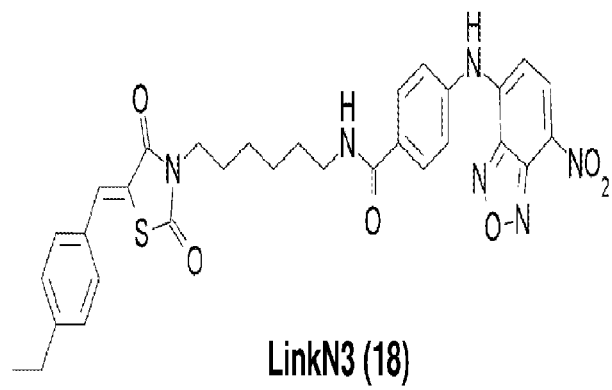
LinkN3 (18)
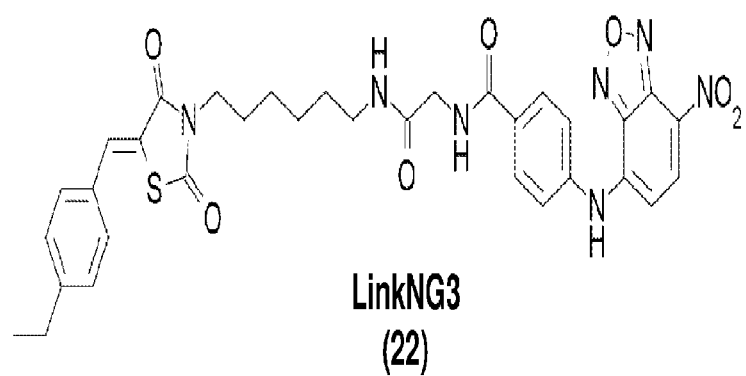
LinkNG3
(22)
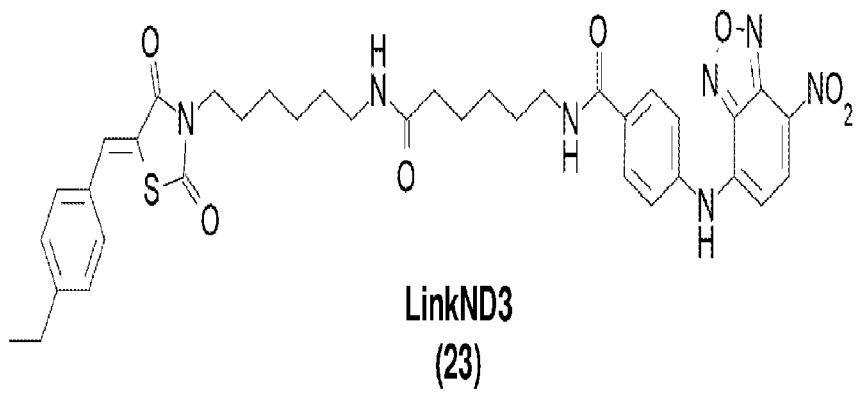
LinkND3
(23)
Fig. 3-2

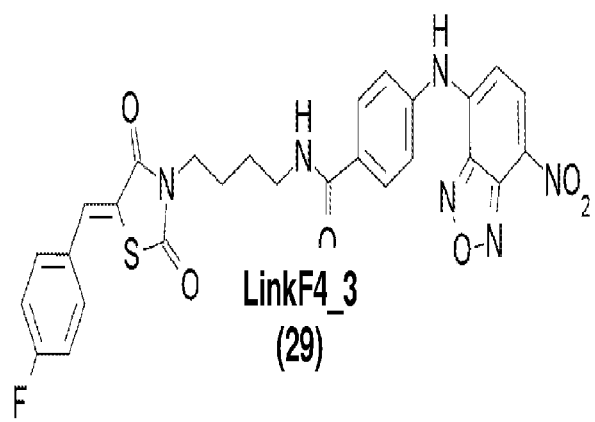
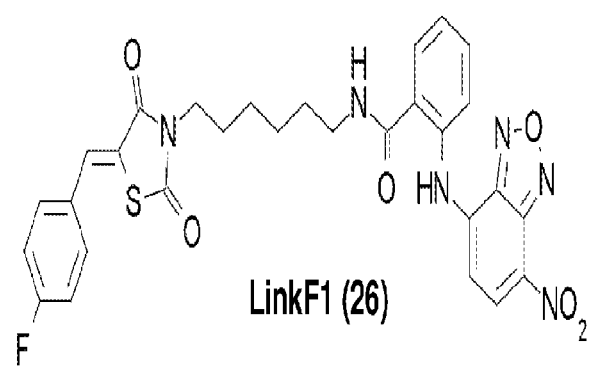
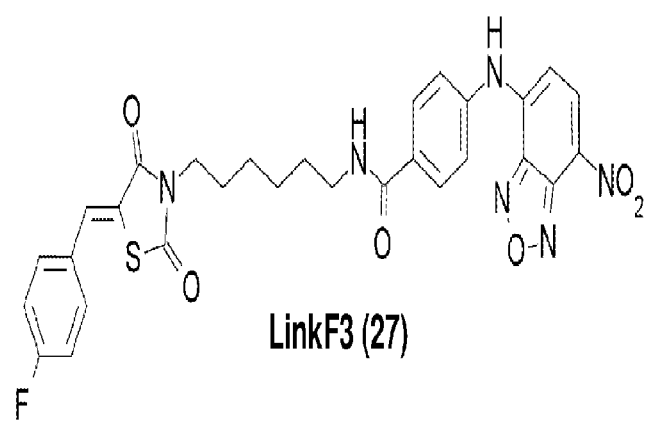
Fig. 3-4

Ac-C5-3-NBn-NBZ  Ac-C5-4-NBn-NBz d

R = Et, n = 3, o: 25
R = F, n = 5, o: 26
R = F, n = 5, p: 27
R = F, n = 3, o: 28
R = F, n = 3, p: 29

APP

```
  1 mdffrvvenq qppatmplnv sftnrnydld ycsvqpyfyc deeenfyqqq qqselqppap
 61 sediwkkfel lptpplspsr rsglcspsyv avtpfslrgd ndggggsfst adqlemvtel
121 lggdmvnqsf icdpddetfi kniiiqdcmw scfsaaaklv seklasyqaa rkdsgspnpa
181 rghsvcstss lylqdlsaaa secidpsvvf pyplndsssp kscasqdssa fspssdslls
241 stesspqgsp eplvlheetp pttssdseee qedeeeidvv svekrqapgk rsesgspsag
301 ghskpphspl vlkrchvsth qhnyaappst rkdypaakrv kldsvrvlrq isnnrkctsp
361 rssdteenvk rrthnvlerq rrnelkrsff alrdqipele nnekapkvvi lkkatayils
421 vqaeeqklis eedllrkrre qlkhkleqlr nsca
```

Fig. 26

LINKED MYC-MAX SMALL MOLECULE INHIBITORS

CROSS REFERENCE TO RELATED APPLICATIONS

This is the U.S. National Stage of International Application No. PCT/US2010/021183, filed Jan. 15, 2010, which was published in English under PCT Article 21(2), which in turn claims the benefit of U.S. Provisional Patent Application No. 61/205,208, filed Jan. 16, 2009. The provisional application is incorporated herein by reference in its entirety.

This application claims priority to U.S. Provisional Patent Application No. 61/205,208, filed Jan. 16, 2009, which is incorporated herein by reference in its entirety.

The cancer-associated basic-helix-loop-helix-leucine-zipper ("bHLH-Zip") transcription factor c-Myc is an appealing therapeutic target. c-Myc is among the most commonly deregulated oncoproteins in cancer, with particularly high levels occurring in lymphomas, breast cancer, prostate cancer, lung cancer, and colorectal cancer. For example, the c-Myc protein or the c-myc gene is overexpressed in 80% of breast cancers, 70% of colon cancer, 90% of gynecological cancers, 50% of hepatocellular carcinomas and a variety of hematological tumors also have abnormal expression. c-Myc is a global transcription factor of the bHLH-ZIP variety that, in association with another bHLH-ZIP partner, Max, binds to specific sites on its target genes and regulates transcription. Highly deregulated c-Myc expression leads to enhanced proliferation, increased cell size, a higher rate of metabolism, DNA damage, and ultimately transformation. All of these functions are highly dependent upon the ability of c-Myc and Max to heterodimerize.

There exists overwhelming evidence implicating c-Myc in the pathogenesis, evolution, and/or survival of many human cancers, and that its therapeutic targeting would be beneficial. This evidence derives from five different types of studies:

c-MYC deregulation in cancer: c-Myc, or its close relative N-Myc, is over-expressed or otherwise deregulated in a variety of cancers. In some cases, a correlation between the degree of over-expression and tumor stage or survival has been demonstrated.

Inactivation of negative regulators of c-Myc is common in human cancers: We have demonstrated that Mxi1, a member of the Mad family, is deleted in nearly half of prostate cancers and, in some cases, is associated with mutational inactivation of the non-deleted allele. Bin1, a protein that interacts with and inhibits the transcriptional regulatory domain (TRD) of c-Myc, is also inactivated or deleted in a significant fraction of prostate and breast cancers. More recently, the tumor suppressor p19$^{ARF}$ has been shown to interact with the c-Myc TRD and thus modulate its target gene induction and transforming activities.

Animal models: A number of animal models have demonstrated that the deregulated expression of c-Myc leads to the eventual emergence of a variety of clonal malignancies. The engineered knockouts of c-Myc negative regulators, including Mxi1, p19$^{ARF}$, and prdx1 also result in an increased cancer incidence, presumably as a consequence of the functional up-regulation of c-Myc. c-Myc can be inhibited for long periods of time in normal cells without significant impairment to the whole animal, although it can reversibly affect the histology of some rapidly proliferating tissues such as colonic epithelium. Moreover, inhibition of c-Myc in such animals can reverse ras-induced lung cancers, demonstrating that inhibition of c-Myc can be selective for malignant cells.

The role of Myc in cell cycle progression, survival, and transformation by other oncogenes. The c-Myc knockout animal is embryonic lethal and primary fibroblasts from such animals do not survive in vitro. Conditional inactivation of c-Myc in primary cells leads to immediate growth cessation and apoptosis; even a 50% reduction of c-Myc in fibroblasts inhibits their transformation by other oncogenes by >90% without affecting proliferation. Therefore it can be argued that even if c-Myc were not directly involved in a specific tumor's etiology, its targeting might still result in a cellular environment that was less conducive to supporting a number of oncogene-dependent pathways.

Transient inhibition of c-Myc may be sufficient to achieve therapeutic effect. Transient inhibition of c-Myc can lead to tumor regression, as shown utilizing tetracycline-regulatable Myc models of lymphoma and osteosarcoma. These c-Myc-dependent tumors regress and undergo apoptosis following c-Myc silencing. Unexpectedly, rather than leading to tumor re-growth, the re-induction of c-Myc leads to massive apoptosis in 80% of cases. These findings suggest that even transient inhibition of c-Myc might be both therapeutically successful and desirable.

In summary, current evidence favors the notion that c-Myc deregulation is critical for tumorigenesis, thus making this oncoprotein an attractive therapeutic target. The possibility that transient inhibition of c-Myc might be even more effective than long-term inhibition must also be given serious consideration.

Specific inhibition of c-Myc is thus a major therapeutic goal. Among the direct approaches taken to inhibit c-Myc has been the use of triplex-forming oligonucleotides, which interfere with cMYC gene transcription, and anti-sense oligonucleotides, which either promote c-Myc mRNA degradation or inhibit its translation. Indirect approaches have included the specific inhibition of downstream c-Myc target genes and "suicide" vectors encoding cytotoxic proteins under the control of c-Myc-responsive promoters. Despite some successes, most of these approaches continue to be hampered by technical difficulties pertaining largely to delivery and the fact that many transforming c-Myc target genes are functionally redundant and/or cell type-specific.

More recently, we and others have employed a different approach that utilizes low molecular weight compounds (hereafter referred to as "Myc-Max compounds") to inhibit or reverse the association between c-Myc and its obligate bHLH-LZ heterodimerization partner, Max. In its transcriptionally active form, the c-Myc-Max heterodimer binds specifically to canonical DNA sequences termed E-boxes, which are usually located within the proximal promoters or first introns of positively-regulated c-Myc target genes. Negative gene regulation by c-Myc, also requires Max, although DNA binding occurs at non-E-box-containing InR elements located at transcriptional initiation sites. Thus, Myc-Max compounds not only abrogate protein heterodimerization and DNA binding by c-Myc-Max but all subsequent downstream functions as well. However, most studies only demonstrated low potencies for such inhibitors (IC$_{50}$'s generally >20-50 µM).

We undertook a study to identify small molecules that could disrupt the c-Myc Max interaction and that might potentially be useful as therapeutic agents. Our initial screening test was based on a "yeast two hybrid approach." In this assay, the bHLH-ZIP moiety of c-Myc were fused to the DNA binding domain of a yeast transcription factor (Gal4). This chimeric protein could bind genes that contained Gal4 yeast binding sites but was unable to activate transcription. Via a similar approach the Max bHLH-ZIP domain was fused to the Gal4-transcriptional activation domain. When the two fusion proteins were co-expressed, the interaction between c-Myc and Max reconstituted the yeast transcription factor such that it could now bind to Gal4 sites and activate the transcription of an adjacent gene, which in this case encoded the easily assayable β-galactosidase.

We have previously described several small-molecules that prevent the interaction between c-Myc and its obligate bHLH-Zip heterodimerization partner Max. However, lack of mechanistic insight into their action has limited the development of improved analogs.

SUMMARY

Disclosed herein are methods and compositions for disruption of c-Myc binding and activation. In certain embodiments, the compositions comprise moieties that specifically bind c-Myc and further disrupt its association with its binding partner Max. For example, in some embodiments, the compositions comprise moieties which specifically bind c-Myc.

In certain embodiments, the binding moieties described herein are linked together via a linking molecule. Such linked moieties are thus able to bind at least two sites in c-Myc molecules, thereby disrupting its ability to associate with Max. Such molecules are particularly useful for regulating the expression of c-Myc within a cell. It has been surprisingly found that by combining relatively low affinity binding molecules, a synergistic level of binding affinity can be achieved.

In other embodiments, the composition of the c-Myc binding moieties comprises a compound having the formula

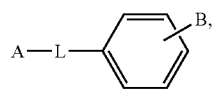

wherein A and B are moieties that bind Myc, and L is a flexible linker Some of the binding moieties of interest include: Bicyclo[2.2.1]hept-2-yl-[2-(4-nitro-phenyl)-ethyl]-amine; 4-Methyl-2-[N'-(6-methyl-2-phenyl-chroman-4-ylidene)-hydrazino]-thiazole-5-carboxylic acid (3-nitro-phenyl)-amide; 3-[3-(3,6-Dichloro-carbazol-9-yl)-2-hydroxy-propyl]-thiazolidine-2,4-dione; 1-(3-Chloro-phenyl)-3-diethylamino-pyrrolidine-2,5-dione; 1-[2,5-dioxo-1-(4-propoxy-phenyl)-pyrrolidin-3-yl]-piperidine-4-carboxylic acid; compounds generally having the formula

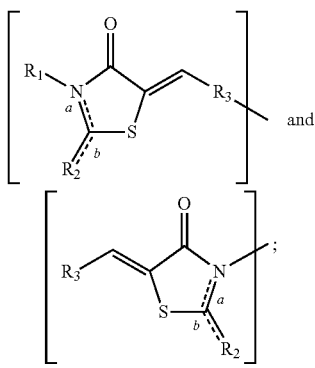

and a compound generally having the formula

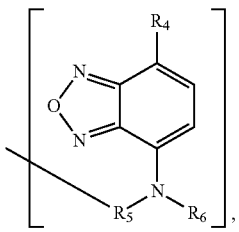

and pharmaceutically acceptable salts thereof, as described in further detail herein.

Various forms of linkages are also contemplated. For example, the linker can comprise —(CH$_2$)$_n$— where n is an integer from 1 to 10. In another embodiment the linker can comprise —[C(O)—NH]$_m$[(CH$_2$)$_n$—NH—C(O)]$_p$—, where m is an integer from 0 to 1, n is an integer from 1 to 10, and p is an integer from 1 to 3. In yet another embodiment the linker can comprise —[C(O)—NH]$_m$—[(CH$_2$)$_n$—NH—C(O)]$_p$—, where m is an integer from 0 to 1, n is an integer from 1 to 6, and p is an integer from 1 to 2.

Additionally embodied are methods of treatment for diseases wherein Myc dysregulation contributes to pathogenesis. For example, in certain embodiments, the compositions described herein can be formulated as pharmaceuticals designed to treat diseases such as Burkitt's lymphoma cell; non-Burkitt's lymphoma; prostate cancer; breast cancer; gastrointestinal cancer; melanoma; multiple myeloma; myeloid leukemia, and others.

BRIEF DESCRIPTION OF THE DRAWINGS

In FIGS. 1-4, reference numbers as well as descriptive names for certain compounds are provided. Reference numbers for the compounds are used in both the figures and in the Examples below.

FIG. 26. Exemplary c-myc amino acid sequence (GenBank Accession No. NP_002458; SEQ ID NO: 1).

SEQUENCE LISTING

Figure 1:
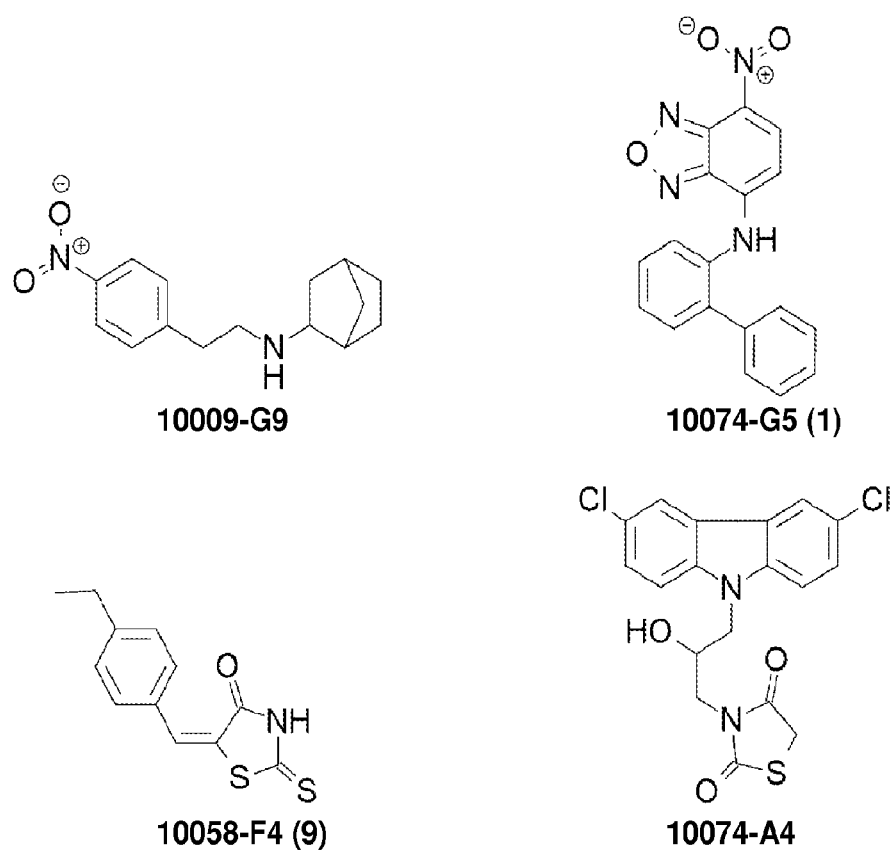
FIGS. 1-4 provide structures of various compounds described herein, including precursors, intermediates and linked compounds.
Figures 1, 2:
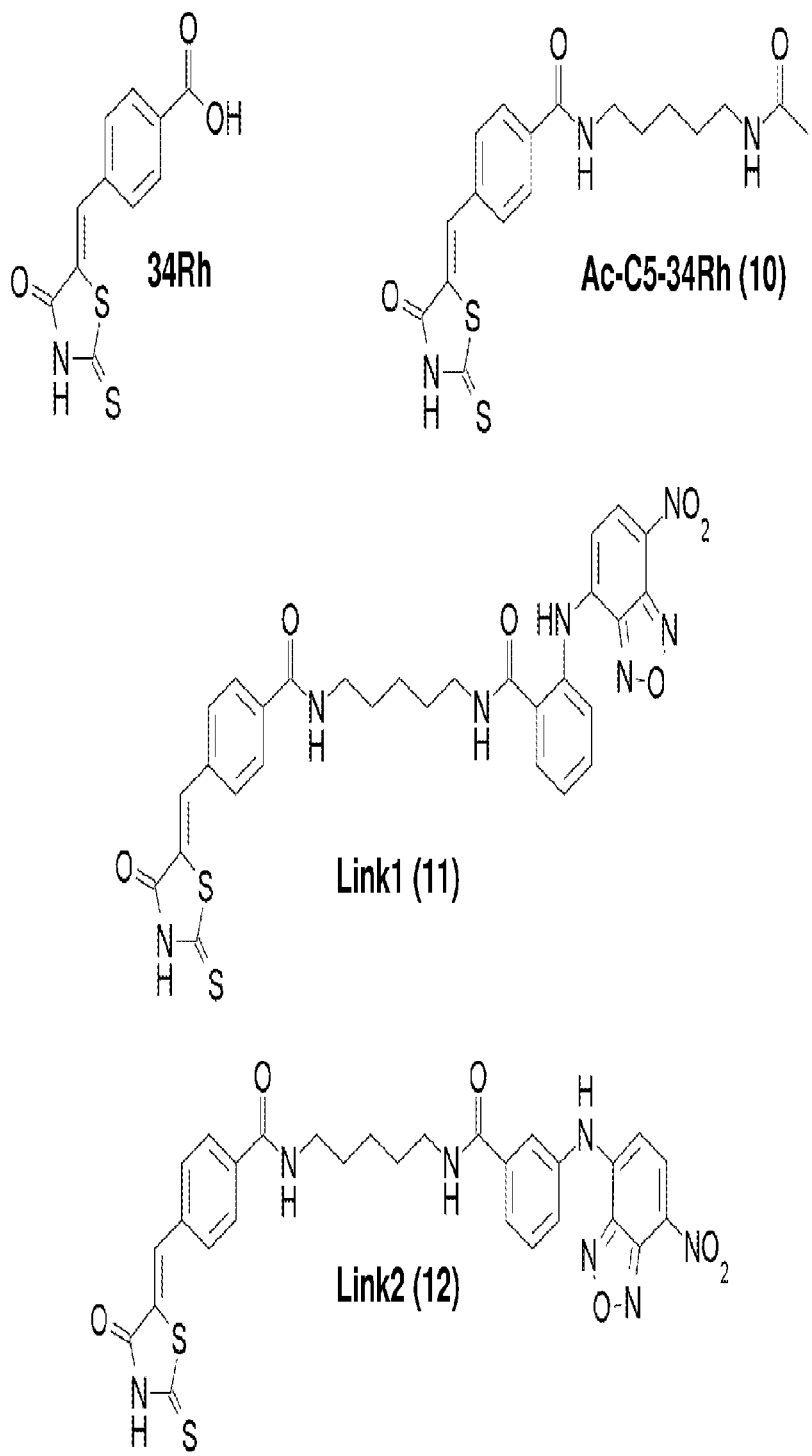
Figure 2:
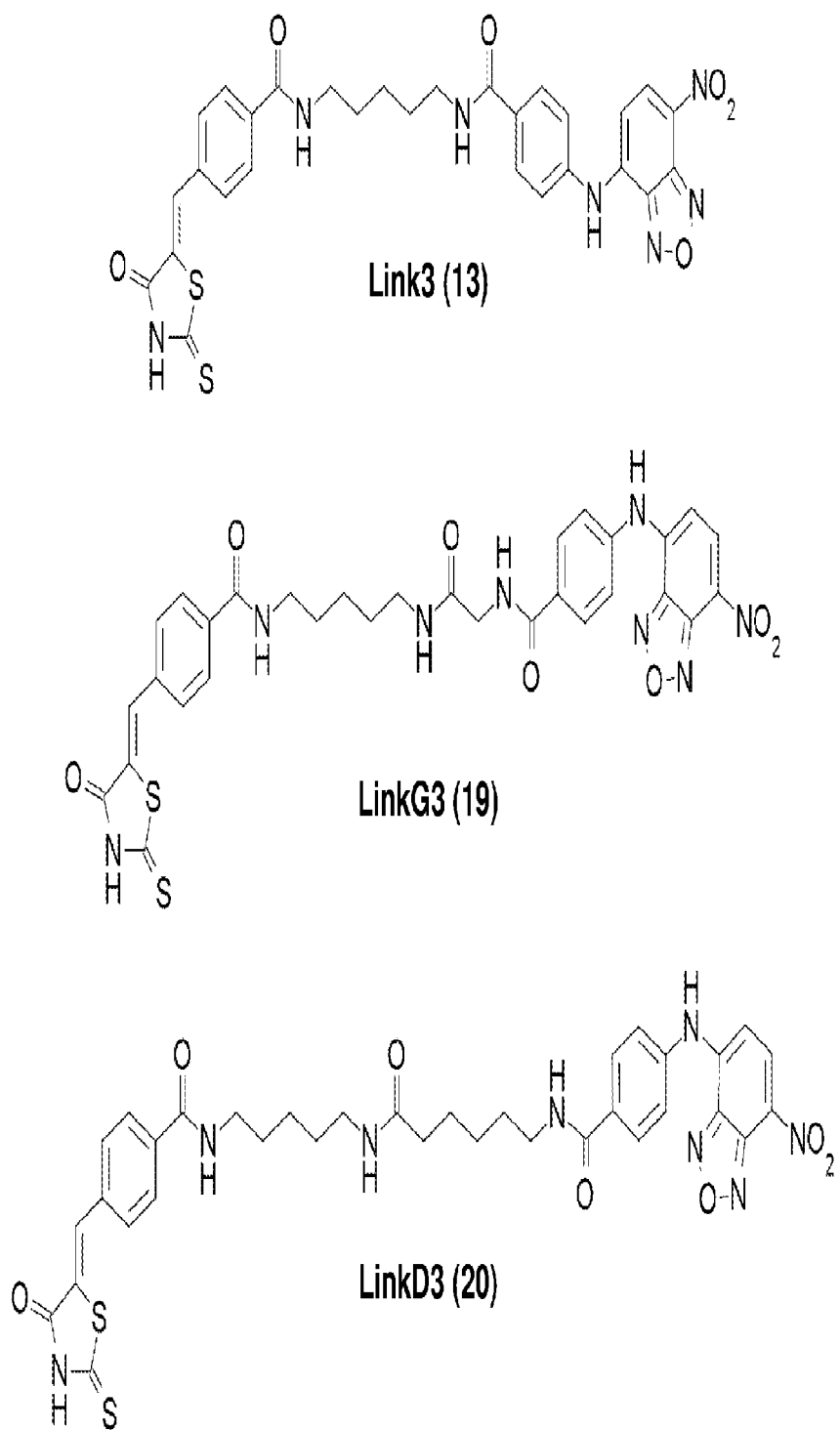
Figures 1, 3:
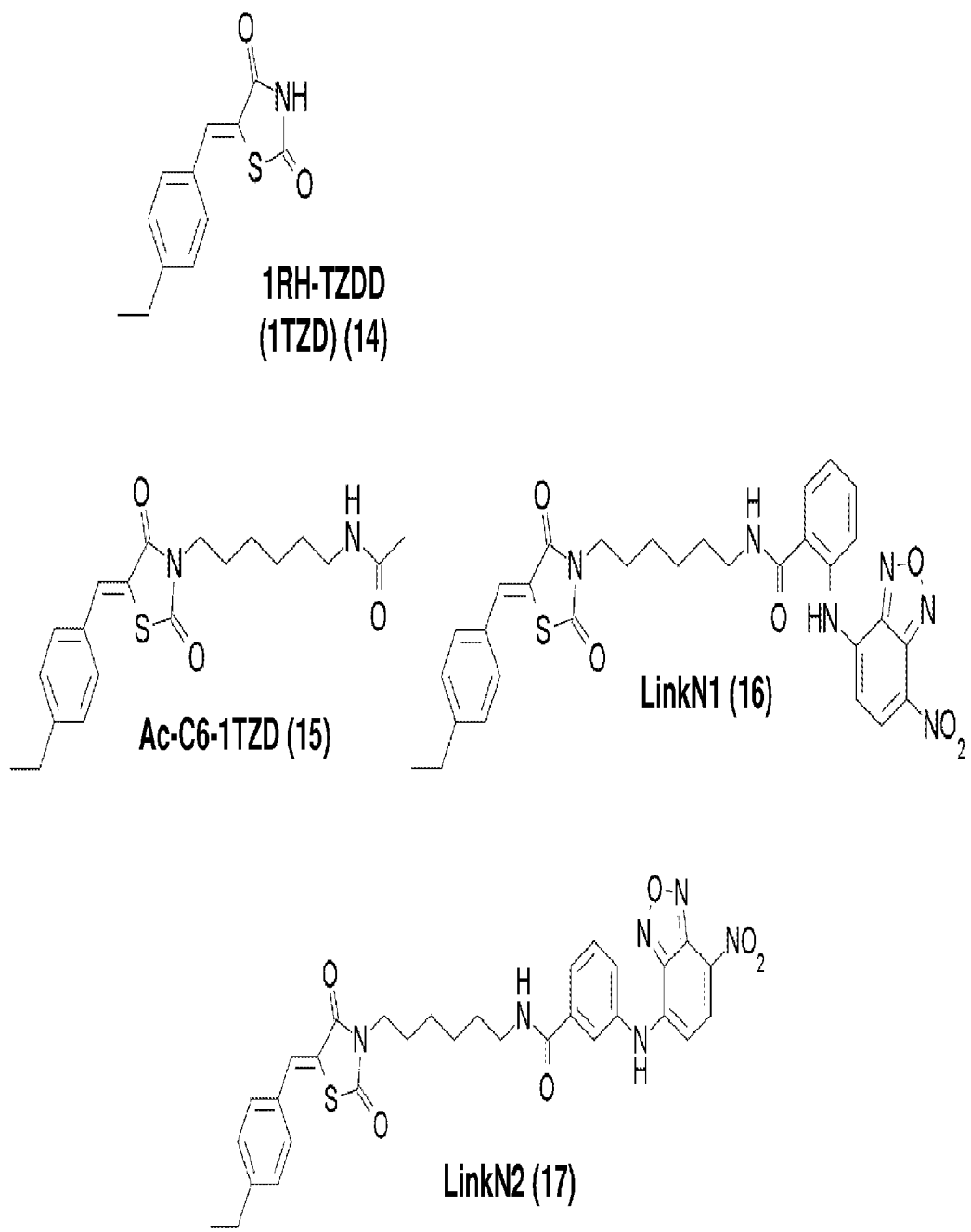
Figure 3:
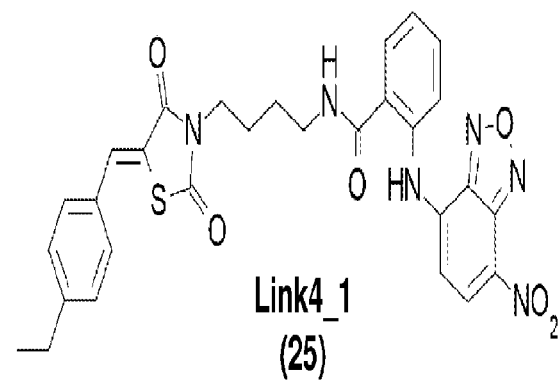
Figure 3:
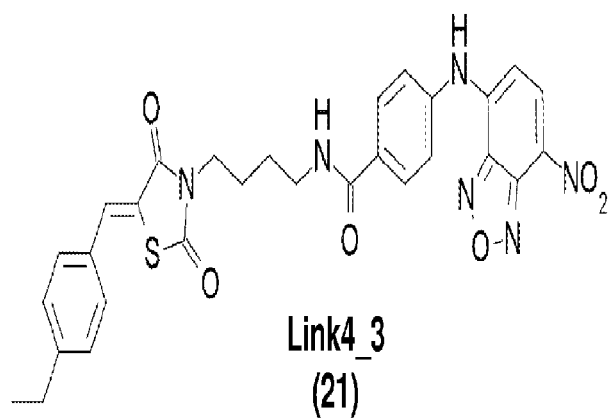
Figure 3:
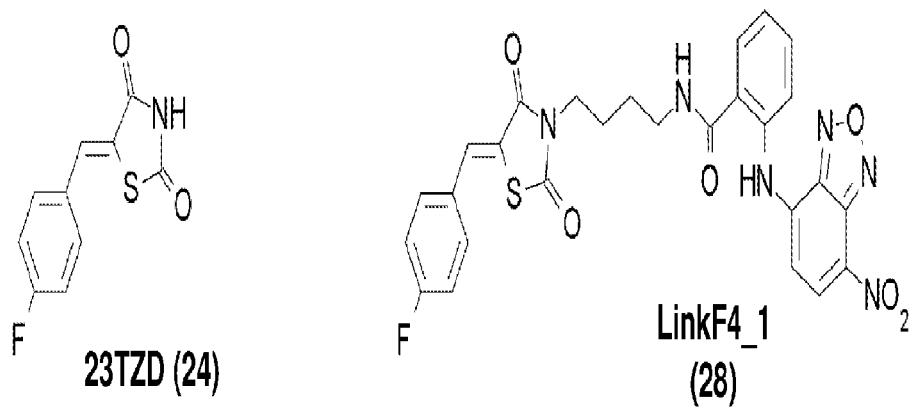
Figures 1, 4:
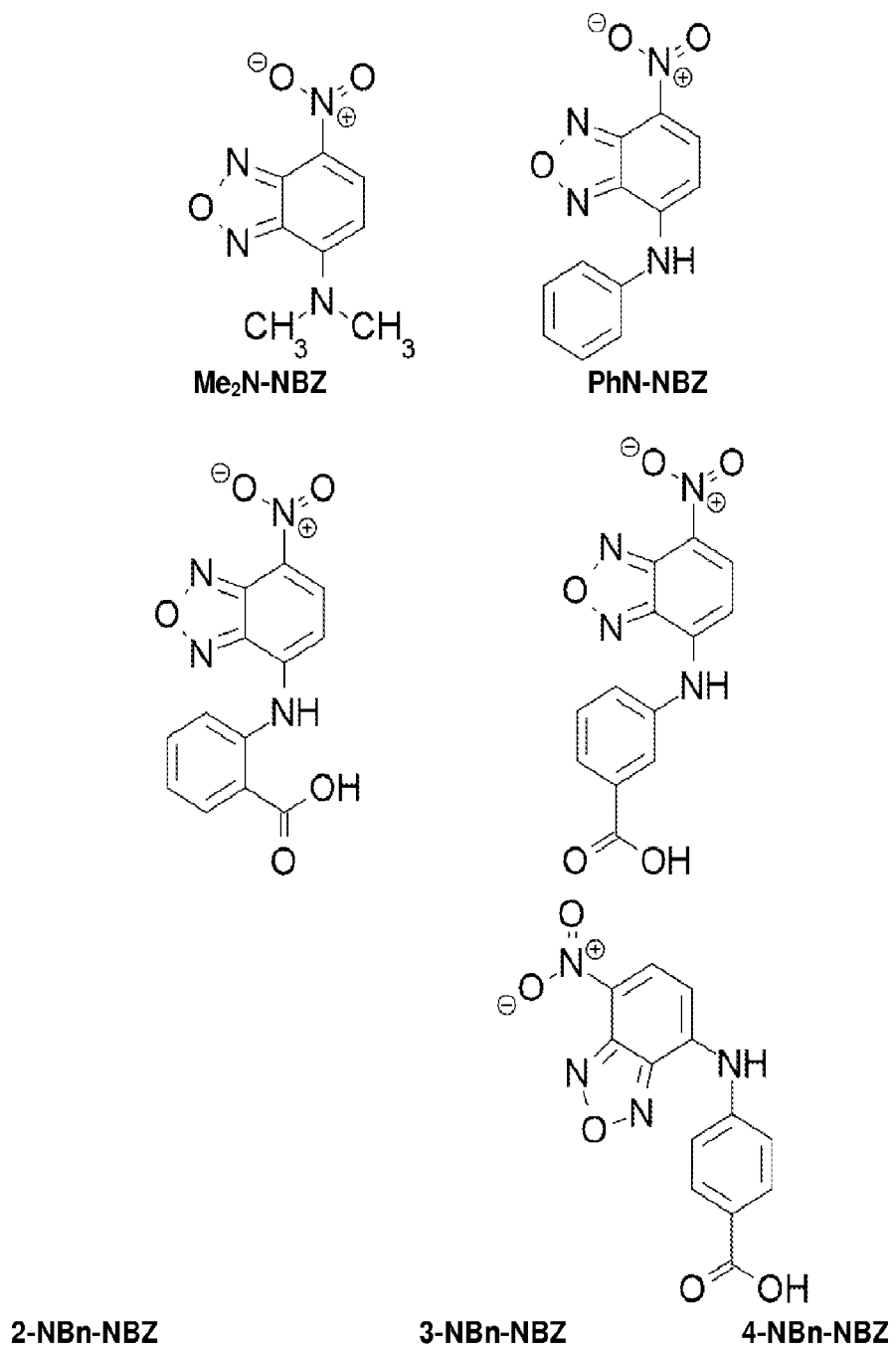
Figures 2, 4:
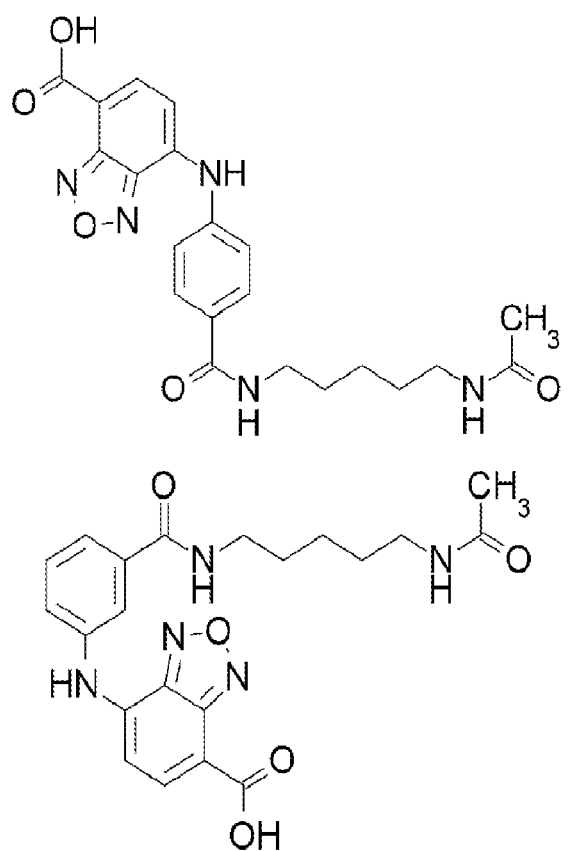

The amino acid sequence listed in the accompanying sequence listing is shown using standard three letter code for amino acids, as defined in 37 C.F.R. 1.822. The Sequence Listing is submitted as an ASCII text file, created on Feb. 7, 2013, 4.34 KB, which is incorporated by reference herein.

DETAILED DESCRIPTION

The use of numerical values in the various ranges specified in this application, unless expressly indicated otherwise, are stated as approximations as though the minimum and maximum values within the stated ranges are both preceded by the word "about", whether or not the term "about" is present. In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, and unless indicated otherwise, "a", "an" and/or "the" refer to one or more.

As used herein, the term "comprising", is intended to be inclusive and/or open-ended and does not exclude additional, unrecited elements or method steps.

A "drug product" is a compound, composition, formulation, etc. as is understood in the medical and pharmaceutical arts. Drug products comprise an "active agent" which is a compound or composition that has a specific pharmacological effect. A drug product is preferable "pharmaceutically acceptable," meaning that it is suitable for administration to a subject for a stated purpose, which is typically referred to as an "indication". Irrespective of whether a drug product or other composition, compound or material may or may not cause harm by its administration to a subject, it may be "pharmaceutically acceptable" if benefits of the composition, compound, material or drug product outweigh its risks. In one aspect, a compound, composition, material, excipient or drug product is pharmaceutically acceptable if it meets the requirements of an applicable regulatory agency, such as the US Food and Drug Administration, or any other applicable regulatory body, which includes, without limitation, compounds, compositions, materials or drug products that are Generally Recognized As Safe (GRAS). In a broader sense, a composition, compound, material or drug product and it is material is not biologically or otherwise undesirable for its intended use, that is, the material can be administered to an individual along with the relevant active compound without causing clinically unacceptable biological effects or interacting in a deleterious manner with any of the other components of the pharmaceutical composition in which it is contained.

Compounds that selectively prevent or disrupt the association between the c-Myc oncoprotein and its obligate heterodimeric partner Max ("Myc-Max compounds") have been previously identified by high-throughput screening of chemical libraries (see, U.S. Pat. No. 7,026,343 and U.S. patent application Ser. No. 11/707,421). Although these agents specifically inhibit the growth of c-Myc-expressing cells, their clinical applicability is limited by their low potency.

Described herein are several chemical modifications of one of these original compounds, which result in significant improvements in efficacy. These chemical modifications include linking two single binding Myc-Max compounds that bind to interfere with Myc and Max association at different binding sites. Compared to the single binding Myc-Max compounds, these linked compounds demonstrate increased binding affinity for the Myc BHLH-Zip construct. As such, the binding is synergistic over what would be expected for simple bi-valent compounds. As used herein, the term "synergistic" refers an effect which exceeds simple additive effects.

Our group has identified the starting compounds for the current studies. The cMyc-Max specific inhibitors that target the dimerization domain subtype BHLH-Zip include: (Z,E)-5-(4-ethyl-benzylidene)-2-thioxo-thiazolidin-4-one (hereinafter referred to as 10058-F4); 3-[3-(3,6-Dichloro-carbazol-9-yl)-2-hydroxy-propyl]-thiazolidine-2,4-dione (hereinafter referred to as 10074-A4); and biphenyl-2-yl-(7-nitro-benzo[1,2,5]oxadiazol-4-yl)-amine (hereinafter referred to as 10074-G5) (see, U.S. Pat. No. 7,026,343 and U.S. patent application Ser. No. 11/707,421).

10058-F4 is structurally the simplest, being comprised of a six-member ethylbenzylidine ring and a five-member thioxothiazolidin-4-one, or rhodanine ring (Yin X, et al. Oncogene 2003; 22:6151-9 and FIG. 1). The ability of 10058-F4 to target c-Myc-Max, to disrupt the heterodimer and/or to prevent its formation, and to abrogate various c-Myc-dependent functions has also been confirmed independently by several other groups (Kolly C, et al. Proliferation, cell cycle exit, and onset of terminal differentiation in cultured keratinocytes: pre-programmed pathways in control of C-Myc and Notch1 prevail over extracellular calcium signals. J Invest Dermatol 2005; 124:1014-25; Gomez-Curet I, et al. c-Myc inhibition negatively impacts lymphoma growth. J Pediatr Surg 2006; 41: 207-11; Mo H, Henriksson M. Identification of small molecules that induce apoptosis in a Myc-dependent manner and inhibit Myc-driven transformation. Proc Natl Acad Sci USA 2006; 103:6344-9 and Huang M J, et al. A small-molecule c-Myc inhibitor, 10058-F4, induces cell-cycle arrest, apoptosis, and myeloid differentiation of human acute myeloid leukemia. Exp Hematol. 2006; 34:1480-9). In combination, these properties have established 10058-F4 as an attractive starting point for the generation of analogs with improved efficacy.

Described herein are the consequences of linking together Myc-Max compounds to obtain linked compounds. Using several independent assays and analytic methods, a number of linked compounds have been identified as superior to any particular inhibitor when used alone. These results provides further proof of principle that improved compounds that inhibit Myc and Max association can be obtained by a stepwise design approach that includes identifying the binding sites of compounds in the bHLH-Zip domain and using a flexible linker to covalently link compounds that bind at different sites.

As used herein, the terms "linked compound" and "linked Myc-Max compound" refer to a compound having the formula

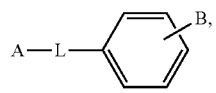

wherein A is a compound that interferes with Myc and Max association at a first site, B (which is shown with no specific attachment point, indicating that it can be ortho, meta or para to A-L-) is a second compound that interferes with Myc and Max association at a second site, and L is a flexible linker In certain embodiments the binding site for A on c-Myc is different than the binding site of B on c-Myc.

As used herein, the terms "A" and "B" represent single binding Myc-Max compounds or moeities that selectively prevent or disrupt the association between Myc and Max at particular sites, thereby interfering with Myc and Max association. In one non-limiting embodiment, A is 10058-F4 or a derivative thereof, and B is 10074-G5, or a derivative thereof. Non-limiting examples of single binding Myc-Max compounds include those that have been previously identified by high-throughput screening of chemical libraries (see, U.S. Pat. No. 7,026,343 and U.S. patent application Ser. No. 11/707,421, incorporated by reference in their entirety).

As used herein, the terms "Myc-Max inhibitory compound" and "Myc-Max inhibitory compounds" generally refer to compound(s) that interfere with Myc and Max association. Non-limiting examples of Myc-Max inhibitory compound(s) include single binding Myc-Max inhibitory compounds and linked Myc-Max compounds.

As used herein, the terms "derivative" and "derivatives" referring to a Myc-Max compound include chemically modified versions of the parental Myc-Max compound. The Myc-Max compounds, or derivatives thereof, may be derivatized to contain chemical groups that, for example: modify the solubility of the compound, for example by the addition of a poly(ethylene glycol) group; modify the cell permeability of the compound, for example by the addition of aliphatic groups; allow for attachment of the flexible linker, for example by the addition of one of more reactive carbonyl-containing groups, such as amide groups, acyl groups, or carboxylic groups; or permit detection of the compound, for example by conjugation with a fluorochrome, such as fluorescein isothiocyanate, Cy3 or Cy5 or a radionuclide-containing or caging group for in vitro or in vivo detection and location of the compounds or derivative thereof.

Non-limiting examples of A include derivatives of 10058-F4 (see FIGS. 1-10). Non-limiting derivatives of 10058-F4 include:

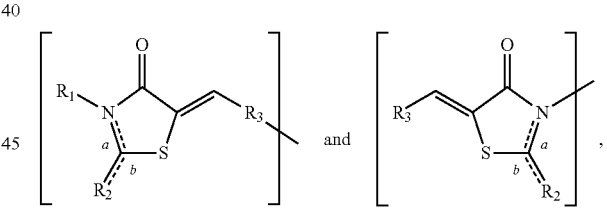

wherein $R_1$ is H, alkyl, or 5-6 atom heterocyclic group, or is not present, wherein the 5-6 atom heterocyclic group comprises one or more of

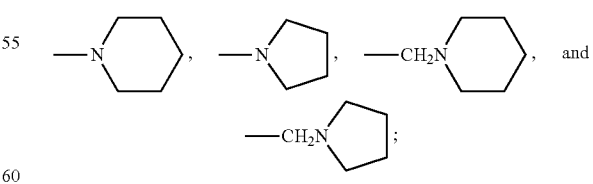

$R_2$ is O, S, $C_{1-3}$ alkoxyl group, or $C_{1-3}$ alkylthiyl group; and $R_3$ is one of phenyl, diphenyl, naphthyl, a substituted phenyl, cyclohexyl, and a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxy group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group and a and/or b are single or double bonds; including:

a)

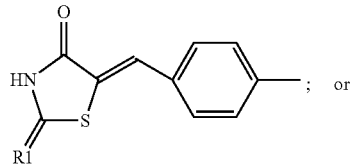

; or b)

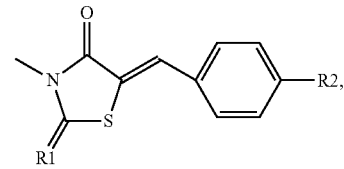

wherein $R_1$ is O or S and $R_2$ is halo or ethyl.

Non-limiting examples of B include derivatives of 10074-G5 (see FIGS. 1-10). Non-limiting derivatives of 10074-G5 include:

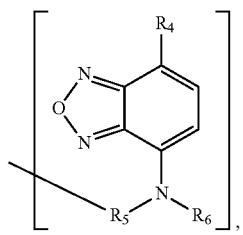

wherein $R_4$ is a nitro group or a carbonyl group; $R_5$ is one of phenyl, diphenyl, naphthyl, a substituted phenyl, cyclohexyl, a substituted cyclohexyl, or not present, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and $R_6$ is H, alkyl, or 5-6 atom heterocyclic group; including: is

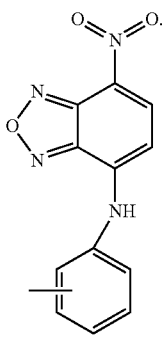

As used herein, the term "linker" refers to a linking group covalently attached between A and B. The linker can comprise different functional groups. A "linker" is typically biologically or pharmaceutically inert and/or acceptable. For example and without limitation, functional groups include $C_1$-$C_{10}$ alkyl groups, such as straight chain, branched, conjugated, aryl, and phenyl groups; and carbonyl groups, such as ester, amide, and carboxylic groups.

As used herein, the term "flexible linker" refers to a linker that contains at least one single covalent bond that allows for the atoms or functional groups within the linker to rotate freely around the single covalent bond. Non-limiting examples of covalent bonds include: $C_1$-$C_{10}$ alkyl groups, such as straight chain, branched, and conjugated groups; and carbonyl groups, such as ester, amide, and carboxylic groups. For example and without limitation, the flexible linker comprises —$[(CH_2)_m$—$Ar_n]_p$—, wherein Ar is an aryl group, m is from 1 to 10, n is from 1 to 5, and p is from 1 to 5. In this example, the —$CH_2$— groups enable at least one aryl functional group to rotate with respect another aryl functional group within the linker Therefore, the linker in its entirety is flexible. In another non-limiting example, the flexible linker comprises —$[C(O)$—$NH]_m$—$[(CH_2)_n$—$NH$—$C(O)]_p$, wherein m is from 0 to 1, n is from 1 to 10, and p is from 0 to 3. In yet another non-limiting example, the flexible linker comprises —$(CH_2)_m$—, wherein m is from 1 to 10.

In certain embodiments, linkage can be achieved by using a linear Boc protected amino aldehyde. Knoevenagel condensation between the position 5 of the thiazolidine dione ring of 3-[3-(3,6-Dichloro-carbazol-9-yl)-2-hydroxy-propyl]-thiazolidine-2,4-dione and the aldehyde would be followed by removal of the Boc protecting group and amide formation with 34-Rh or aminobenzoic acid derivatives of a compound generally having the formula:

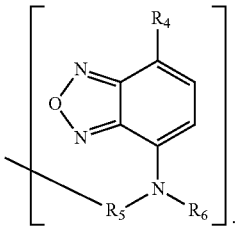

The connection of Bicyclo[2.2.1]hept-2-yl-[2-(4-nitrophenyl)-ethyl]-amine with a linker can be achieved by means of amide formation or Shiff's base formation (in certain examples, followed by reduction) from reaction of the compound's secondary amine with a carboxylic or carboxylic terminal linker respectively. 1-(3-Chloro-phenyl)-3-diethylamino-pyrrolidine-2,5-dione can be linked via substitution of carboxyl or amine group on the phenyl ring which can allow reaction with spacer compound. Alternately, one of the ethyl groups can be extended in the original synthesis and include a carboxyl group (or other similar reactive group) that would allow linkage via amide bond formation (or similar facile reaction). 1-[2,5-dioxo-1-(4-propoxy-phenyl)-pyrrolidin-3-yl]-piperidine-4-carboxylic acid can be connected to an amino terminal linker by means of amide bond formation with its carboxylic functionality. 4-Methyl-2-[N'-(6-methyl-2-phenyl-chroman-4-ylidene)-hydrazino]-thiazole-5-carboxylic acid (3-nitro-phenyl)-amide can be linked via modification of the isolated phenyl ring (off of the bicyclic moiety) with a carboxylic acid and subsequent amide bond formation with a linker molecule.

Also described herein are compositions and methods for inhibiting growth or proliferation of a cell, comprising contacting the cell with an amount of a compound that interferes with Myc and Max association effective to inhibit growth or proliferation of the cell, the compound having the formula:

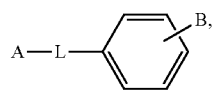

as described herein, wherein A and B interfere with Myc and Max association at different binding sites, and L is a flexible linker, in an amount effective to interfere with c-Myc and Max association effective to inhibit growth or proliferation of the cell, and a pharmaceutically acceptable excipient.

As used herein, the term "cell" and "cells" refer to cells lines and any types of cells from or within a subject, such as, without limitation, rat, mice, monkey, and human. As used herein, the term "subject" refers to members of the animal kingdom including but not limited to human beings and mammals, et alia.

The compounds described herein can be used to treat a subject, such as a patient, with a cancer that implicates c-Myc. Increased activity by c-Myc is broadly known for its central role in many cancers. Non-limiting examples of diseases implicating a role of c-Myc include: Burkitt's lymphoma, non-Burkitt's lymphoma, prostate cancer; breast cancer; gastrointestinal cancer; melanoma; multiple myeloma; and myeloid leukemia. As shown herein, the compounds and compositions described herein are shown to directly affect growth of members of this group, including Burkitt's lymphoma and myeloid Leukemia (HL-60) cells. As such, methods are provided for reducing cell growth rates of tumor (proliferating) cells in a subject (e.g., patient, or a human subject or patient) having a cancer in which interference with c-Myc expression, e.g., interference with Myc-Max binding results in decreased growth rate of the tumor cells, which is readily determinable by a person of ordinary skill using the binding assays and/or growth assays, such as the fluorescent polarization, EMSA and MTT assays described herein. As indicated above, and in the data presented herein, those cancers include, without limitation one or more of Burkitt's lymphoma; non-Burkitt's lymphoma; prostate cancer; breast cancer; gastrointestinal cancer; melanoma; multiple myeloma; and myeloid leukemia.

As used herein, "pharmaceutically acceptable," means acceptable for use in humans and animals. "Excipients" include, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, wax(es), oil(s) and water. The choice of excipient depends on the dosage form in question. The drug product may be administered, without limitation, intravenously, intramuscularly, orally, topically, intratumorally, intraperitoneally, intrathecally, rectally, vaginally, nasally, optically, buccally, transdermally, subdermally, intradermally, etc., as is appropriate and/or desirable for treatment. Parenteral administration may require at a minimum buffers and salts to match physiological conditions, and thus includes salt and buffer, such as, without limitation, normal saline or phosphate-buffered saline. Depending on the solubility of the compound (active ingredient), the dosage form may be aqueous, micellular (including liposomes) or lipophilic. Formulation of a drug product and choice of suitable excipient(s) with adequate bioavailability is within the average skill of those in the pharmaceutical and formulary arts. The compound may be administered via any useful delivery route, including, without limitation, orally or parenterally, and the drug product/dosage form is tailored to the desired delivery route. For example and without limitation, an HCl salt of a compound described herein may be administered intravenously or intramuscularly in normal saline, or may be administered in tablet or capsule form with appropriate excipients. A large variety of dosage forms are known in the pharmaceutical arts, and many of which may be appropriate for treatment using the methods and compositions described herein (see generally, Troy, D B, Editor, Remington: The Science and Practice of Pharmacy, $21^{st}$ Edition, Lippincott, Williams & Wilkins (2005)).

In any case, as used herein, any agent used for interfering with Myc and Max association is administered in an amount effective to slow or stop growth of a cell in an amount and in a dosage regimen effective to prevent, reduce the rate of cellular growth. As shown herein, dose-response curves indicate that, for example and without limitation, concentration ranges of from about 0.01 nM (nanomolar) to about 100 μM (micromolar) of any given drug product may prove useful. Different excipients or reagent systems, dosage forms, administration routes and salt or free-base forms of the active ingredients would be expected to affect bioavailability and the specific activity of the active agent, and thus the ability of any given active ingredient to decrease cellular growth rates in an individual. Administration of different amounts or concentrations of the active ingredient using different dosage regimens will achieve similar results, with the drug product administered, typically and without limitation, from one to ten times daily, including 2, 3, 4, 5, 6, 7, 8, 9 and 10 times daily. The amount of the drug product administered to the subject, also may vary depending on the dosage form. A person of average skill in the pharmaceutical and medical arts will appreciate that it will be a matter of simple design choice and optimization to identify a suitable dosage regimen for treatment of any given disease state (e.g., cancer).

Dosage forms include, without limitation, tablets, capsules, liquids for injection, eyedrops (liquids), ointments, oils, multi-phase systems (such as, liposome, micellular, homogenates or suspensions of liquids or semi-solid or solid particles), gels, creams and transdermal devices.

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

Methods for determining if a compound binds to c-Myc, comprise, for example and without limitation: determining by fluorescent polarization if the presence of a first amount of one of a Myc protein or a portion of Myc protein that contains a c-Myc bHLH-ZIP dimerization/DNA binding domain in a solution containing a fluorescent polarizing compound depolarizes light to a different degree as a solution containing a different amount, or none of the Myc protein or portion thereof; determining by x-ray crystallography if a compound binds to c-Myc bHLH-LZ; or determining by NMR spectroscopy if a compound binds to c-Myc bHLH-LZ. In one embodiment, as shown below, fluorescent polarization is used to determine if the compound binds to cMyc.

Examples

The following Examples are provided for illustration and, while providing specific example of embodiments described herein, are not intended to be limiting.

Methods

Chemical structures relating to reference numbers provided below are shown in FIGS. 1-10. Synthetic procedures and compounds characterization. All reagents and solvents were >98% purity and were purchased from Sigma-Aldrich. Mono Boc protected 1,5 N-pentyldiamine was purchased from Novabiochem (Läufelfingen, CH). Dichloromethane (DCM) and dimethylformamide (DMF) were dried on molecular sieves. Glassware was dried by flaming before usage. NMR, recorded on 400 MHz or 300 MHz Varian INOVA instruments, and LC-MS, performed with a Varian 500-MS Ion Trap spectrometer, were employed for product characterization. HPLC, with a 30 minutes gradient 100% A:0% B to 0% A-100% B (where A=water, 0.1% V/V trifluoroacetic acid [TFA], B=acetonitrile, 0.1% V/V TFA) on a Varian ProStar instrument equipped with a C18 reversed phase Alltech Econosphere column was employed for product purification, when needed, and purity assessment. Detection wavelengths were set at 350 and 450 nm.

Condensation of benzaldehydes with rhodanine or 2,4-thiazolidinedione

Rhodanine or 2,4-thiazolidinedione (3 mmol) and 0.69 g ammonium acetate were dissolved with heating in 4.5 mL glacial acetic acid. The aldehyde substrate (1.1 equivalents) was slowly added. The mixture was refluxed for 2 hours, cooled to room temperature and diluted with 50 mL water to precipitate the product. The reaction is stereoselective and only Z product is detectable by NMR. Yields were 99% for 1, 95% for 9, 91% for 14 and 60% for 24.

Nucleophylic aromatic substitution of 4-choro-7-nitrobenzofurazan with aromatic amines or dimethylamine To 300 mg 4-Chloro-7-nitrobenzofurazan (1.5 mmol), dissolved in 4 mL anhydrous methanol, 10 µL triethylamine were added, followed by dropwise addition of 1.05 equivalents of reactant primary or secondary amine, dissolved in 6 mL anhydrous methanol. The reactions were stirred at room temperature for three hours, diluted with water, precipitate was collected and recrystallized from water-DMF or water-methanol mixtures. Yields ranged between 73% and 94%. A small-scale reaction (20 µmol) was similarly performed in the final step of preparation of the bivalent compounds 11, 16, 25, 26, 28 using 32, 34, 36, 38 or 40 respectively as the amine reactant, with yields ranging between 58% and 86%, due to extensive formation of byproducts when attempting to react 31, 33, 35, 37 or 39 with 5.

Amide Formation.

The carboxylic substrate (0.4 mmol to 40 µmol, 1 equivalent) was dissolved in the presence of 1.2 equivalents 1-ethyl-3-(3-dimethylaminopropyl)carbodiimide hydrochloride (EDC) in 5 mL to 1.5 mL anhydrous 2:1 DCM-DMF mixture. A catalytic amount of triethylamine was then added, followed by the amine (1.1 equivalents), and the reaction stirred at room temperature for 24 hours. The reaction mixture was then diluted with DCM if necessary to a final volume of 5 mL, quenched with basic water (to remove unreacted acid), it was then washed with diluted aqueous HCl (to remove unreacted amine), followed by solvent evaporation. Yields ranged between 55% and 95%.

Nucleophilic substitution at 2,4-thiazolidinedione imide nitrogen

Compound 14 or 24 (0.4 mmol) was dissolved in 5 mL acetone in the presence of 60 mg $K_2CO_3$. 6-(Boc-amino)hexil bromide or 4-(Boc-amino)butyl bromide (1.05 eq.) was added and the reaction heated to reflux for 3 hours; after cooling to room temperature, precipitate salts were removed by filtration and the solvent evaporated to yield 83%-98% product.

Acetilation of tert-butyl N-(5-aminopentyl)carbamate and 33

Tert-butyl N-(5-aminopentyl)carbamate (0.75 mmol, 1 equivalent) or 33 (60 mmol, 1 equivalent) were dissolved in 5 mL or 1 mL respectively anhydrous DCM, cooled to 0° C. Acetyl chloride (1.5 equivalents) was then added and the reaction let heat up to room temperature over a 20 minutes period, followed by quenching with water. The solvent was the evaporated to yield 99% N-(5-acetamidopentyl)carbamate or 97% 15.

Boc Deprotection.

Substrates were dissolved in anhydrous DCM, 5% TFA (1 to 2 mL) and stirred at room temperature for 2 hours, followed by wash with aqueous $K_2CO_3$ and solvent evaporation. Yields were nearly quantitative in all cases.

Protein Cloning, Expression and Purification.

A c-Myc$_{353-437}$ full-length bHLH-ZIP domain and its truncated version c-Myc$_{390-439}$ were produced from the c-Myc/pET SKB3 construct, kindly supplied by Dr. S. K. Nair (University of Illinois, Urbana-Champaign), by insertion into the pET151D vector, encoding an N-terminal hexahistidine (6× His), separated by a TEV protease digestion site, with the TOPO® ligation system, and over-expressed in E. coli BL21DE3(pLysS). The 6× His tagged human Max isoform p21, with low homodimerization affinity[70], cloned into the pQE10 vector (Qiagen, Inc.), was over-expressed in E. coli M15(pRep4). Bacterial cultures were grown at 37° C. in LB medium to $OD_{600} \approx 0.8$, then induced with 0.5 mM IPTG for 5 hours. Proteins were purified by Ni-agarose chromatography with a pH gradient elution. The 6× His tag of c-MYC$_{353-437}$ and c-Myc$_{390-439}$ was cleaved using TEV protease (the TEV protease was expressed in a pET24 vector [courtesy of S. K. Nair] and purified by Ni-agarose chromatography under native conditions). All the proteins were further purified by HPLC and lyophilized. Protein concentrations were determined by measurement of $OD_{280}$. The synthetic peptide c-Myc$_{363-381}$ is described in Follis, A. V., Hammoudeh, D. I., Wang, H., Prochownik, E & Metallo, S. J. Structural rationale for the coupled binding and unfolding of the c-Myc oncoprotein by small molecules. *Chemistry & Biology* 15, 1149-1155 (2008).

Fluorescence Polarization Titrations.

Samples were analyzed in a Photon Technology International QuantaMaster fluorimeter (Birmingham, N.J.) equipped with polymer sheet polarizers. Titration experiments were performed upon serial dilution of 1:1 equimolar solution of inhibitor and either c-Myc$_{353-437}$, c-Myc$_{390-439}$ or c-Myc$_{363-381}$ in a 1×PBS buffer (137 mM NaCl, 2.7 mM KCl, 4.3 mM Na$_2$HPO$_4$, 1.4 mM KH$_2$PO$_4$, pH=7.4), 5% DMSO, over concentrations ranging between 200 μM and 1.5 nM. Excitation and emission wavelengths were independently determined for each inhibitor. Reported data represent the average of at least three independent experiments. Data were fit to a quadratic equation derived from the thermodynamic expression of binding equilibrium:

$$\frac{[complex]}{[C]_0} = \frac{2 + K_D/[C]_0 - \sqrt{(-2 - K_D/[C]_0)^2 - 4}}{2}, \quad \text{Eq. 1}$$

where $[C]_0$ represents the total concentration of inhibitor and of c-Myc peptide. The value of $K_D$ was determined from the experimental polarization data by fitting to Eq. 2 using KaleidaGraph (Synergy Software, Reading, Pa.) where pol$_0$ is the polarization in the absence of binding and Δpol is the total change in polarization (Park, S. H. & Raines, R. T. Fluorescence polarization assay to quantify protein-protein interactions. *Methods in Molecular Biology* 261, 161-6 (2004)).

$$polarization = pol_0 + \Delta pol \cdot \left(\frac{[complex]}{[C]_0}\right) \quad \text{Eq. 2}$$

Due to the very tight binding of some of the tested compounds, it was impossible to perform a full binding titration with an acceptable fluorescence intensity, therefore the pol$_o$ parameter was experimentally determined from samples of each compound in the absence of c-Myc$_{353-437}$ at a concentration of 25 μM. Binding specificity experiments were performed by monitoring the FP of 10 μM inhibitors solutions in the above-described buffer in the presence of equimolar p21 Max. This protein has low affinity for homodimer formation[70] and no inhibitor showed a change in polarization in its presence.

Circular Dichroism.

Samples of c-Myc$_{353-437}$ (5 μM) in the absence and presence of an equimolar concentration of each tested inhibitor were prepared in 1×PBS buffer. The inhibitors were added from 10 mM stock solutions in ethanol. Spectra were recorded at 25° C. in a 1 mm path-length quartz cuvette on a Jasco J720 spectro-polarimeter. Shown spectra are averaged from three independent samples.

NMR Spectroscopy.

Experiments were performed on a 500 MHz magnet Varian INOVA instrument equipped with a 5 mm single nucleus indirect detection probe. Solutions of c-Myc$_{353-437}$ (~500 μM) in the absence or presence of equimolar inhibitor 18, or 1 and 2 simultaneously, added from a 0.1 M stock in DMSOd$_6$, were prepared in 100% D$_2$O, 5 mM sodium phosphate buffer, pH 7.5. Samples were also prepared of c-Myc$_{353-437}$ alone in 90% H$_2$O—10% D$_2$O, 5 mM sodium phosphate buffer, pH 6.3 (for H$_\alpha$(i)—H$_N$(i+1) NOE sequential assignments). 2D $^1$H homo-nuclear spectra were recorded at 25° C. over sweep widths of ~10×10 ppm with 32-64 scans/t$_1$ increment, 1.5-2 s relaxation delay and sizes of 512-1024×2048 complex points. TOCSY and NOE mixing times of respectively 60 and 150 milliseconds were employed. All spectra were acquired with selective presaturation water suppression. Partial backbone assignments for c-Myc$_{353-437}$ were obtained from TOCSY, COSY and H$_\alpha$(i)—H$_N$(i+1) NOEs of low pH, 90% H$_2$O—10% D$_2$O samples of the pure peptide. Spectra were processed using MestReC software (MestreLab Research, Santiago de Compostela, Spain). Data were filled by linear prediction to a final Fourier transform size of 2048×2048 points and weighted by sine square and sine bell apodization over t$_1$ and t$_2$ respectively before Fourier transformation.

Electrophoretic Mobility Shift Assays (EMSA).

Reactions containing c-Myc$_{353-437}$ and varying concentrations of each tested inhibitor in a buffer containing 1×PBS, 1 mM EDTA; 0.1% NP40; 5% Glycerol; 1 mM DTT; 0.4 mg/mL BSA were incubated for 30 minutes, followed by addition of pre-mixed p21 Max and a synthetic double-stranded oligonucleotide containing a consensus c-Myc-binding "E-Box" element (CACGTG). The final protein concentration was 1 μM for both c-Myc$_{353-437}$ and p21 Max, 10 nM E-Box DNA. The binding reaction was then allowed to proceed for an additional 15 minutes before loading on an 8% running gel (80:1 poly acrylamide:bis-acrylamide). Control experiments with the monovalent parent inhibitors 1 and 2 were similarly performed using a lower (50 nM) concentration of each protein component. Gels were run at 20° C. in 0.5×TBE and scanned on a BioRad FX molecular imager. Data were analyzed with BioRad Quantity One software.

Cell-Based Assays.

These assays were performed as previously described using HL60 promyelocytic leukemia cells and Daudi Burkitt lymphoma cells, each of which expresses high levels of endogenous c-Myc (Wang, H. et al. *Mol. Cancer Ther.* 6, 2399-408 (2007)). As controls for non-specific effects of bivalent compounds, we utilized a c-Myc nulllizygous strain of rat fibroblasts (Mateyak, M. K., et al. *Cell Growth & Differentiation* 8, 1039-48 (1997)) expressing the c-Myc target genes MT-MC1 and HMGAIb, each of which restores a normal growth rate as well as the TGR1 fibroblast line from which the nullizygous line was derived (Wang, H. et al. *Mol. Cancer Ther.* 6, 2399-408 (2007); Mateyak, M. K., et al. *Cell Growth & Differentiation* 8, 1039-48 (1997); and Rothermund, K. et al. *Cancer Research* 65, 2097-107 (2005)). Stock concentrations of parental compounds or bivalent compounds, prepared in DMSO, were added to the indicated final concentration to cells that had been plated the day before in 96 well plates. Cell quantification was performed on triplicate wells over the ensuing 4-5 days without changing the medium by measuring the absorbance at 490 nm using the MTT assay (Mosmann, T. *Journal of Immunological Methods* 65, 55-63 (1983)). IC$_{50}$ values were estimated from linear regression of the inhibition data at the third day of each experiment.

Co-Immunoprecipitation (Co-IP) Assays.

2×10$^6$ HL60 cells were incubated with the indicated amounts of compounds for 6 hr at which time they were centrifuged and washed twice in ice cold PBS. Total cellular lysates were then prepared as previously described (Wang, H. et al. *Mol. Cancer Ther.* 6, 2399-408 (2007)). Lysates were immuno-precipitated with a 1:250 dilution of a rabbit ant-Max antibody (Wang, H. et al. *Mol. Cancer Ther.* 6, 2399-408 (2007) and Zhang, H., et al. *J. Biol. Chem.* 272, 17416-24 (1997)) followed by immuno-blotting with a 1:5000 dilution of the 9E10 anti-c-Myc monoclonal antibody (Santa Cruz Biotechnology, Santa Cruz, Calif.) (Wang, H. et al. *Mol. Cancer Ther.* 6, 2399-408 (2007)). A horseradish peroxidase-conjugated goat ant-rabbit IgG antibody (Santa Cruz) was used as the secondary antibody followed by developing using a chemiluminescence-based signal detection kit (SuperSignal West Maximum Sensitivity, Pierce, Rockford, Ill.) in accordance with the directions of the supplier.

Results

Design and Synthesis of Bivalent c-Myc Compounds.

Figure 6:
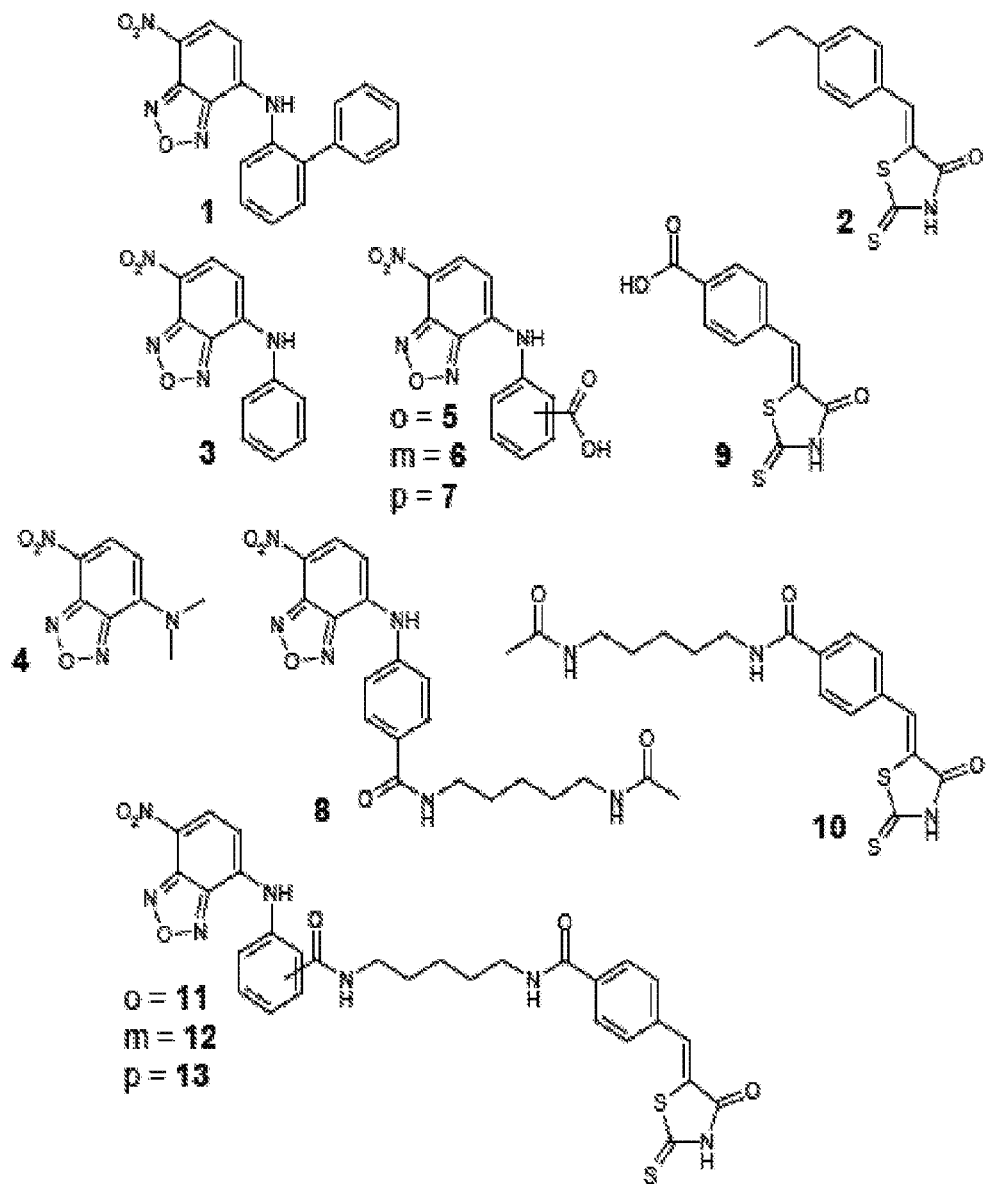
FIG. 6 provides compounds employed to design cross-linked bivalent inhibitors and examples of bivalent inhibitors (11-13).
Figures 1, 7:
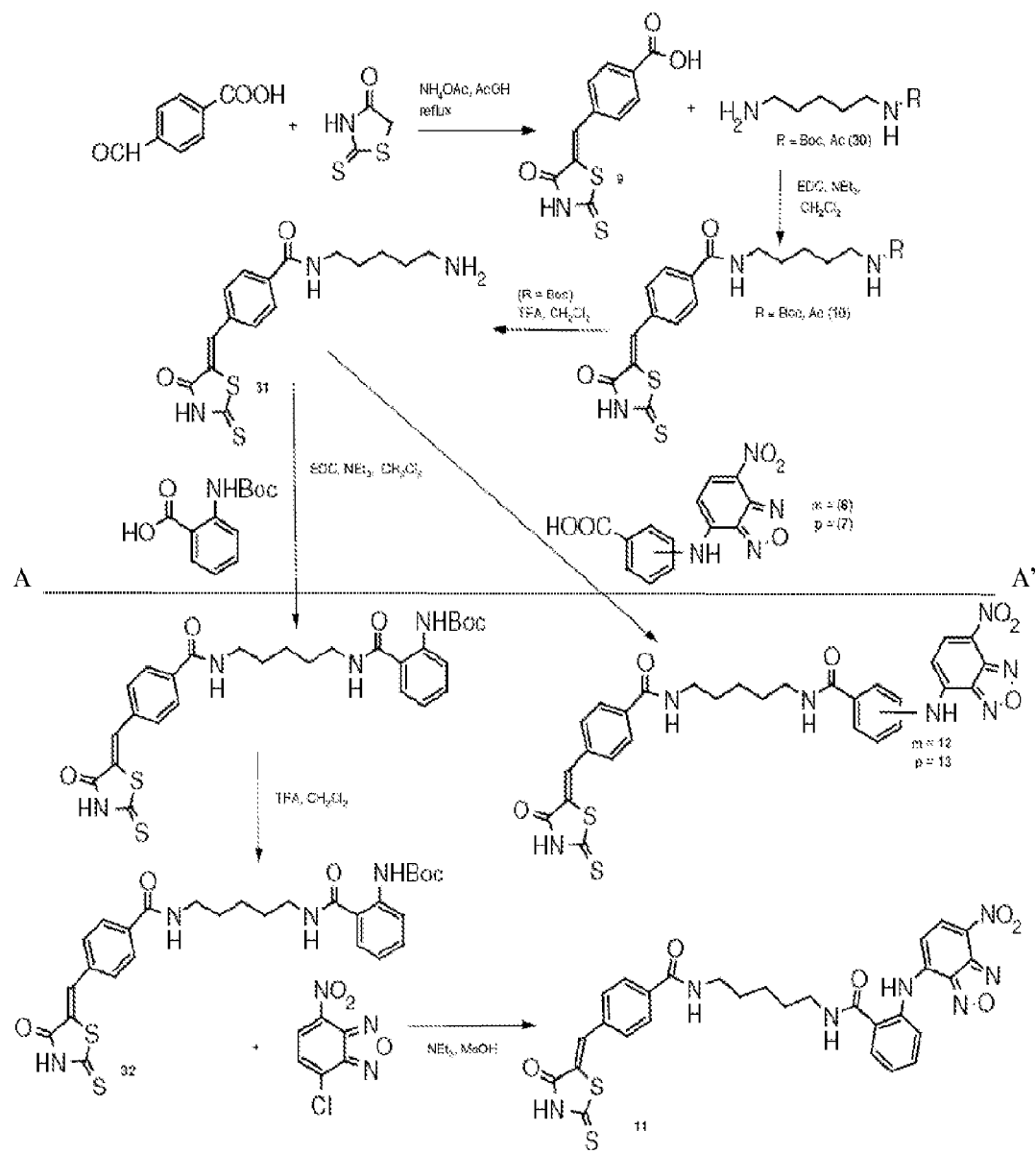
FIG. 7 provides a synthetic scheme for bivalent compounds 11, 12, 13.
Figures 2, 7:
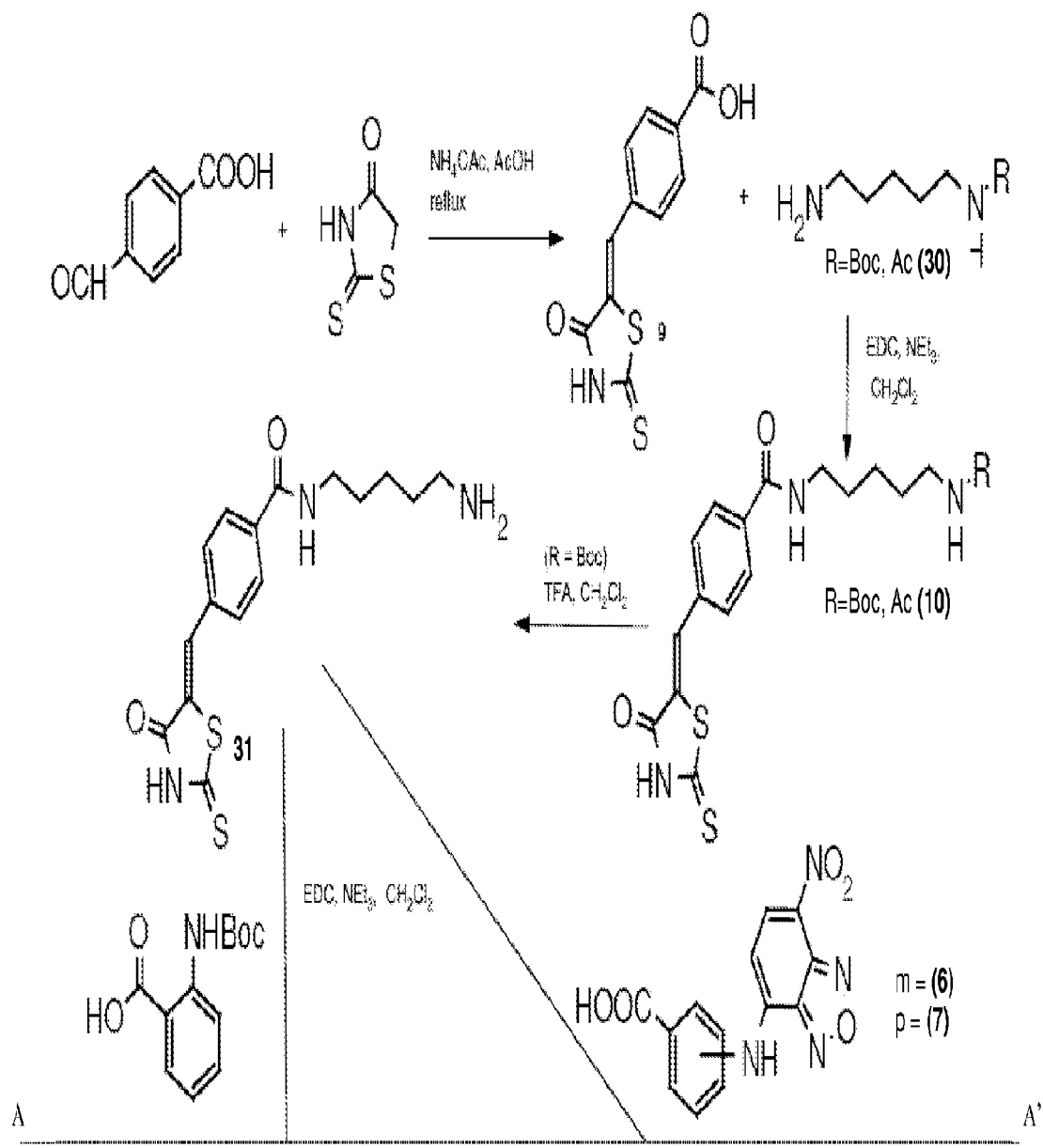
Figures 3, 7:
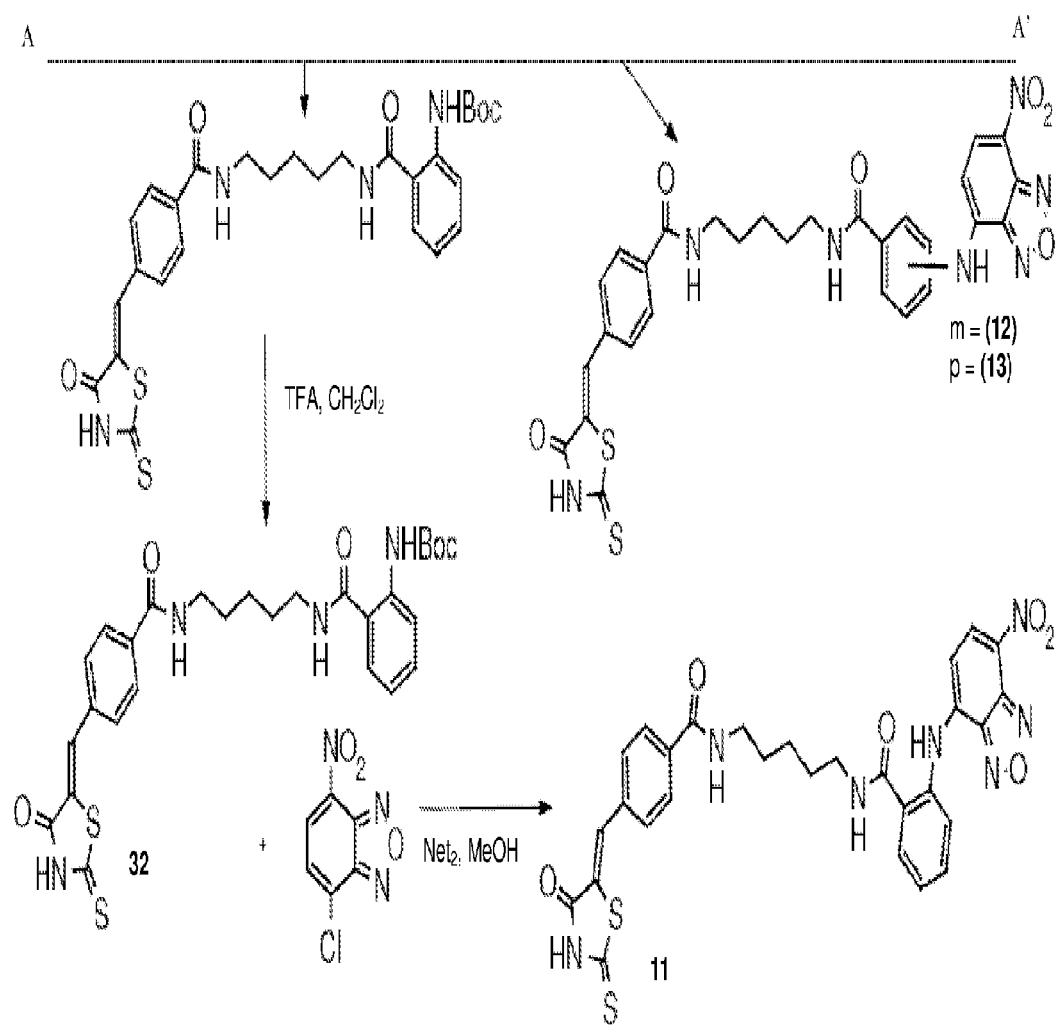
Figure 8:
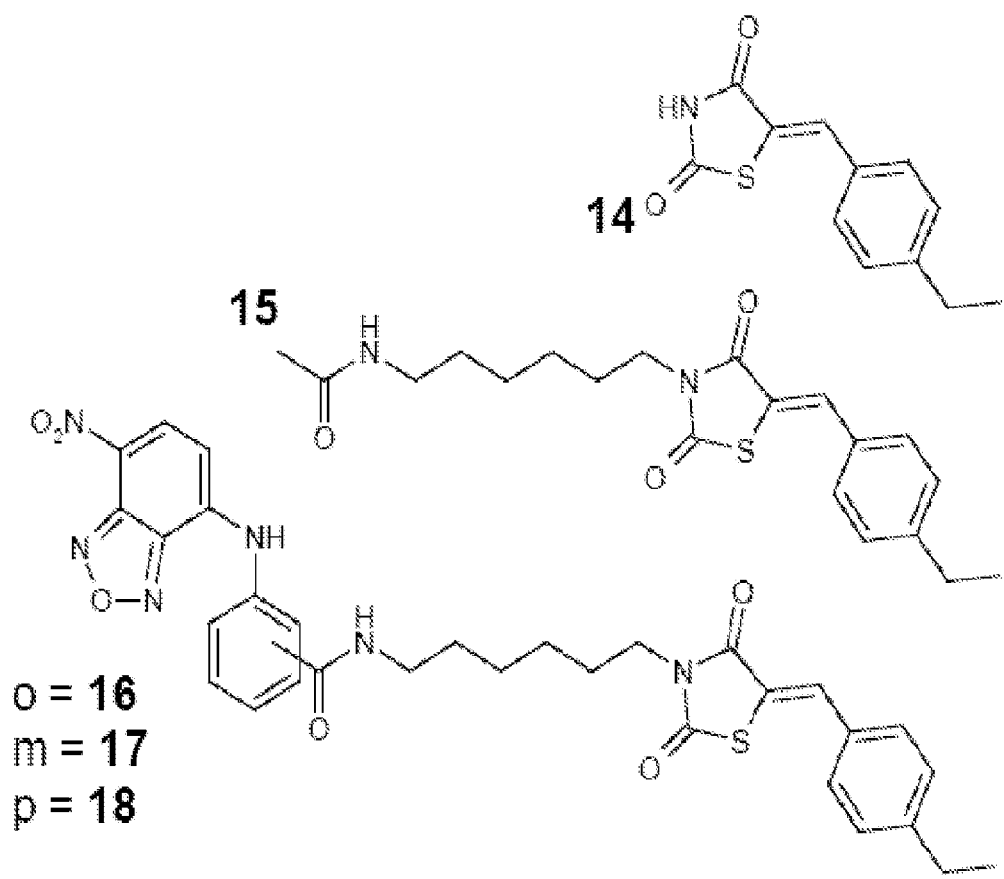
FIG. 8 provides bivalent inhibitors obtained by connecting the aliphatic linker chain to the imide nitrogen of a 2,4-thiazolidinedione derivative of 10058-F4 (2).
Figures 1, 9:
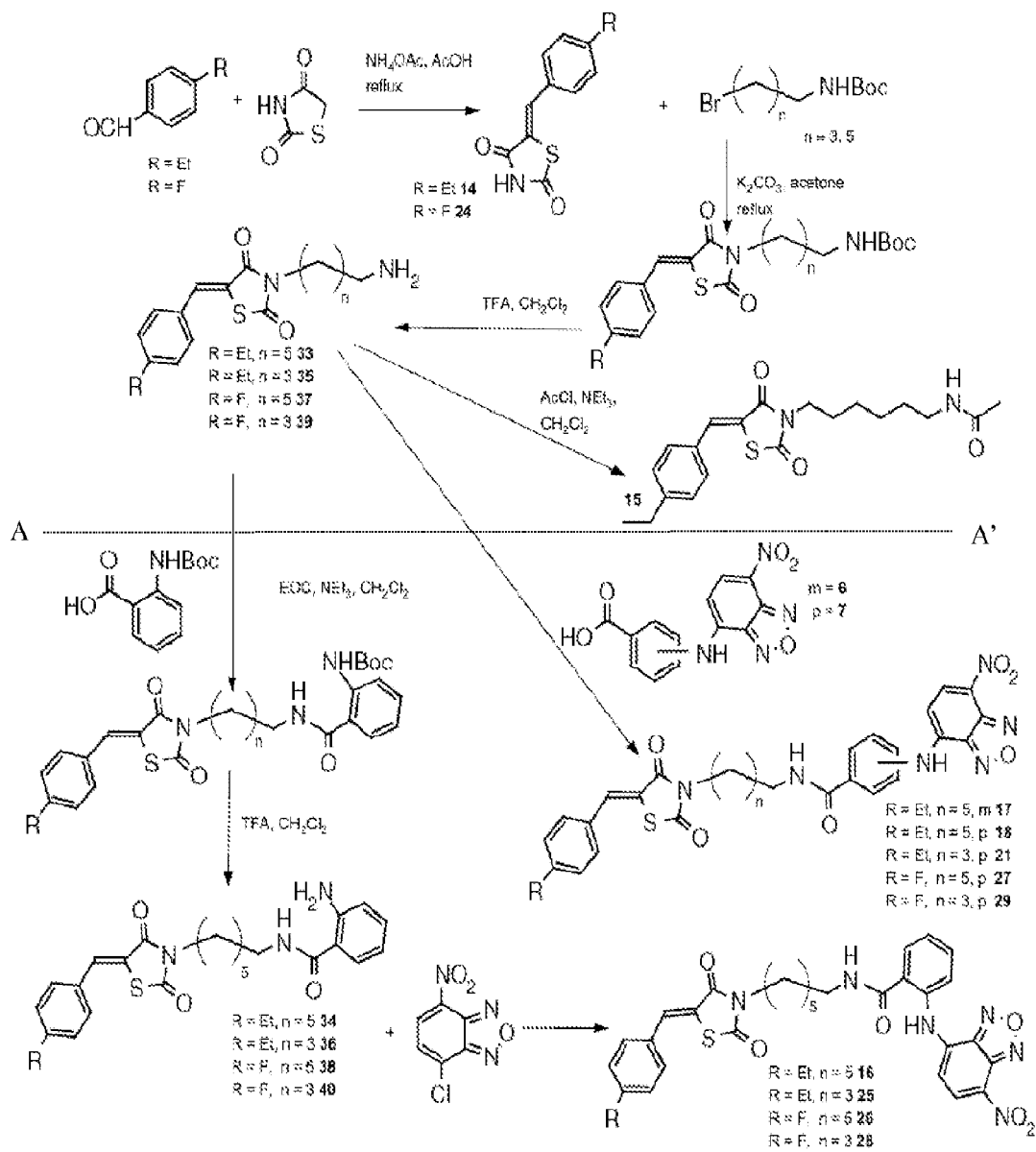
FIG. 9 provides a synthetic scheme for bivalent compounds 16, 17, 18, 21.
Figures 2, 9:
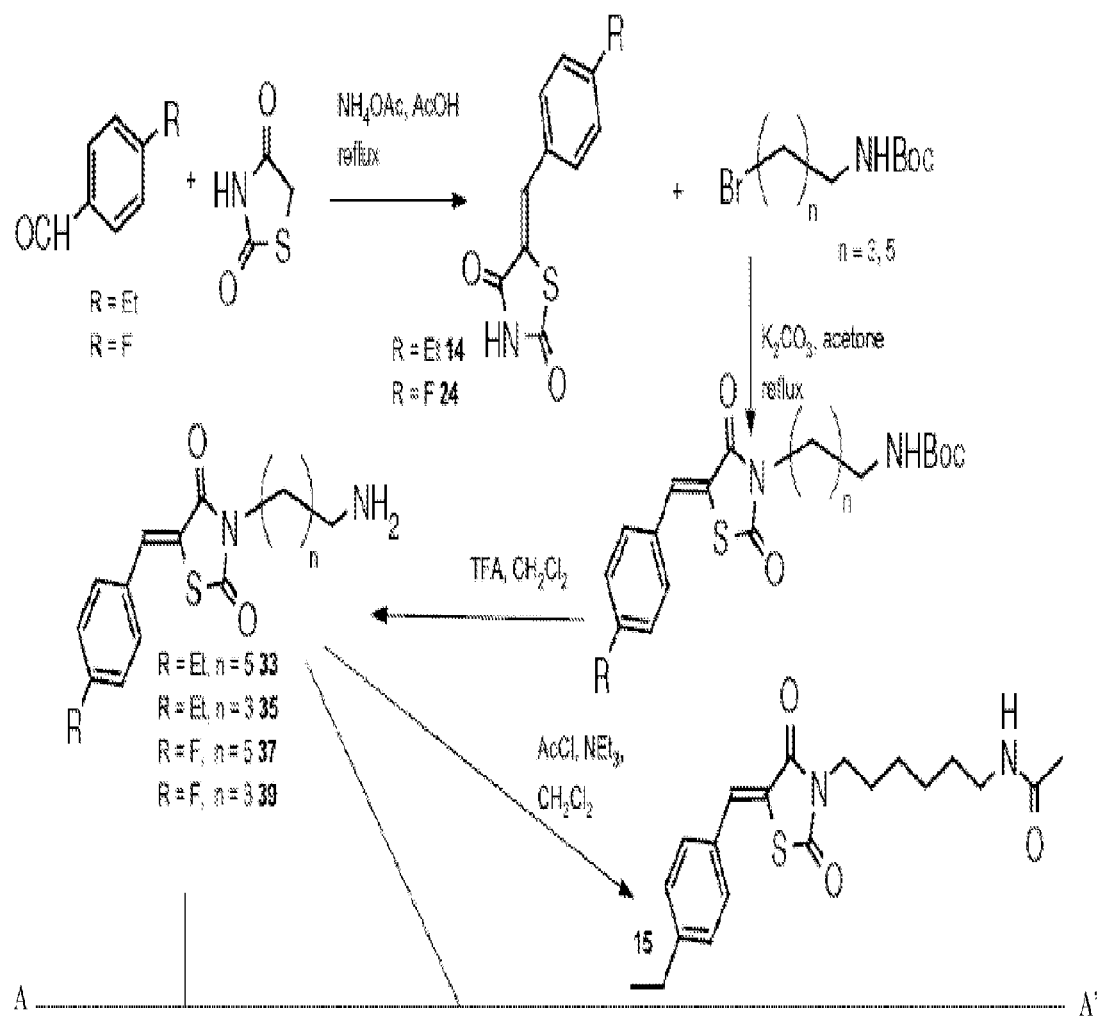
Figures 3, 9:
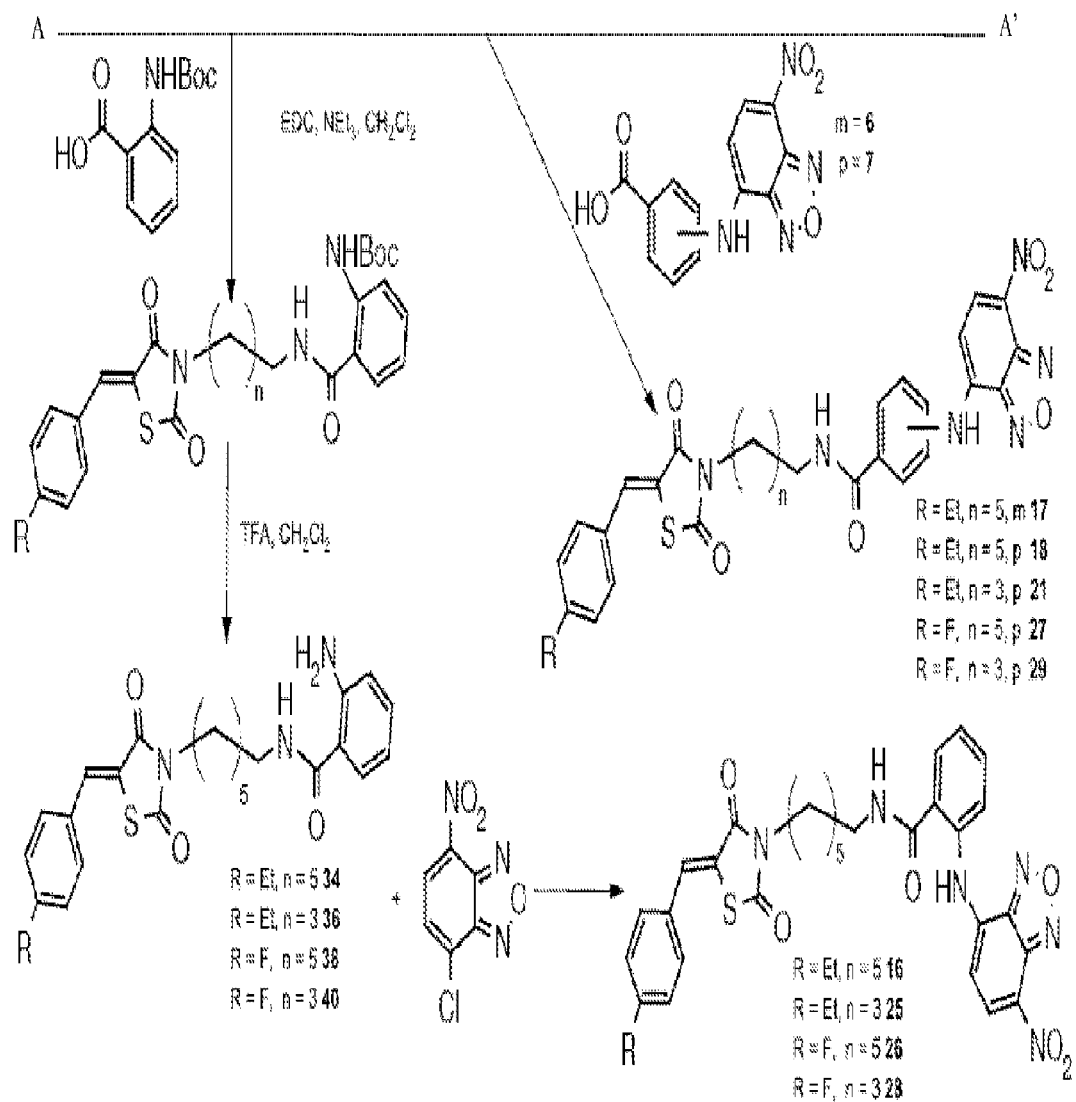

In order to synthesize bivalent inhibitors we designed derivatives of 1 and 2 with functionalities suitable for the connection of a linker moiety. Amino benzoic acid derivatives of 1 were chosen at this purpose. The removal of the second phenyl ring found in 1 improved the atom economy of these structures. The choice of these compounds was based on the observed minor loss of c-Myc affinity of derivatives of 1 upon substitution of the biphenyl moiety with a phenyl ring (3). When replacing the aromatic substituted primary amine with dimethyl amine (4) a complete loss of binding affinity was observed. It was also observed that reduction to amine of the nitro group in position 7 of the condensed heteroaromatic core, achieved by treatment with sodium dithionite (Drin, G. et al. *European Journal of Biochemistry* 268, 1304-14 (2001)), also resulted in a complete loss of binding affinity. This is consistent with the hypothesized interaction of the partial negative charge of this strong dipolar group with positively charged arginine side chains. The reported derivatives of 1, including 2, 3 and 4 amino benzoic acid derivatives (5, 6, 7), were all obtained by nucleophylic aromatic substitution of amines with 4-chloro-7-nitrobenzofurazan (Summers, et al. *J. Org. Chem.* 40, 1559-1561 (1975)). With the goal of assessing the effect of the linker only on the binding moiety derived from compound 1 N-(5-aminopentyl)acetamide was condensed with compound 7 to yield compound 8. We synthesized three bivalent inhibitors by connecting a mono Boc protected pentane-1,5-diamine linker via amide bond formation to a carboxylic derivative of 2 (compound 9)[52]. Condensation of 9 with N-(5-aminopentyl)acetamide was also performed (compound 10) in order to assess the effect of the linker only on the binding affinity for c-Myc of the parent structure 2. The deprotected terminal amine on the linker chain bound to compound 9 was reacted by amide formation with the described carboxylic derivatives of 1 to yield bivalent compounds 11, 12, 13 (FIGS. 6 and 7).

We explored an alternative linking approach, meant to test the modification of the connection between the linker chain and the binding moiety derived from 2, similarly to what done for 1 by connecting the linker chain to 5, 6 or 7. In this strategy we connected, by nucleophilic substitution, Boc protected 6-bromo N-hexan-1-amine to the imide nitrogen of a 2,4-thiazolidinedione derivative of 2 (compound 14)[53]. The obtained product, after deprotection, was acetylated to obtain compound 15, or connected by amide formation to 5, 6 or 7 to yield a second set of bivalent compounds (16, 17, 18, FIGS. 8 and 9).

Figure 10:
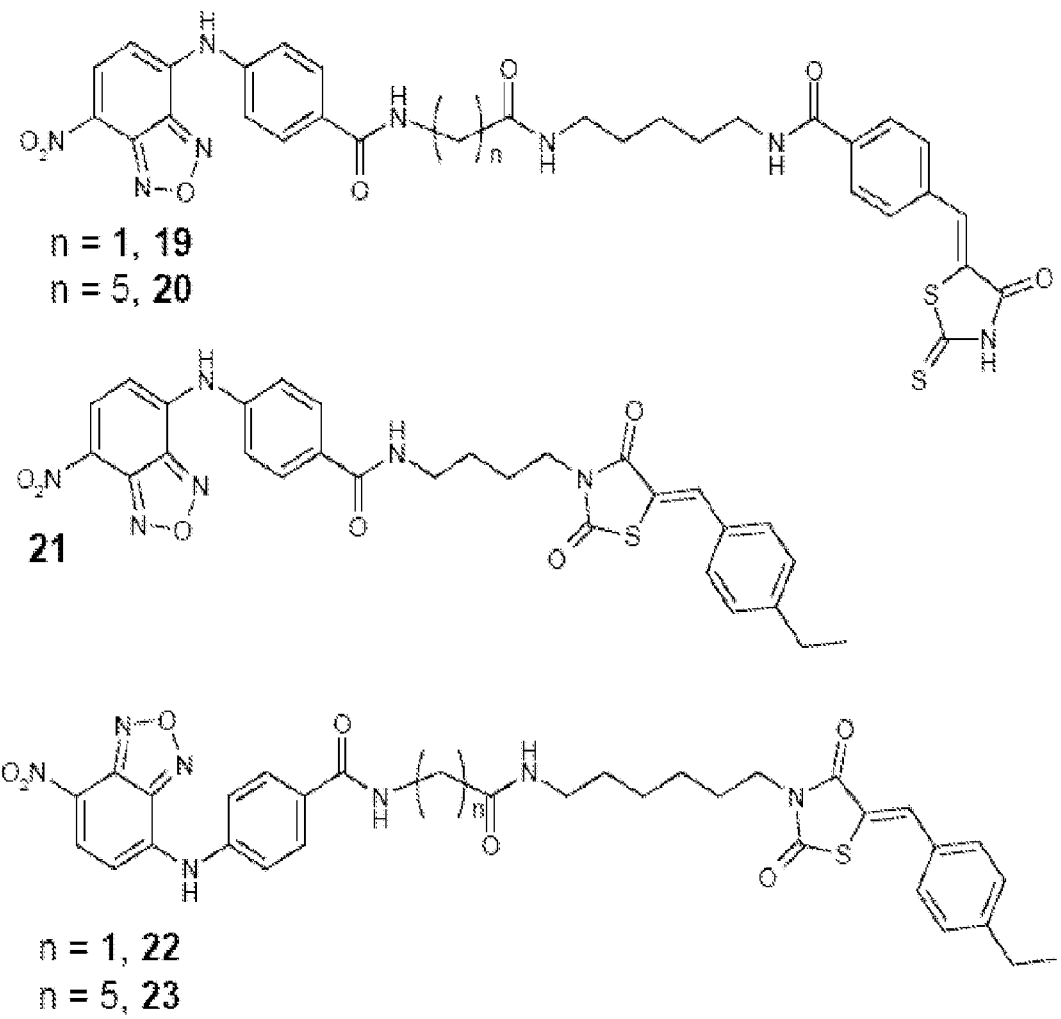
FIG. 10 provides structures of bivalent compounds with variations of the linker chain length.

Lastly, we prepared a series of bivalent inhibitors with longer or shorter linker moieties in order to explore how the length of the linker chain would affect their c-Myc affinity. We reduced the length of the linker chain introduced on 14 by reacting this compound with Boc protected 4-bromobutan-1-amine, or extended the one previously introduced on compounds 9 and 14 by means of amide formation with Boc protected linear amino acids (Boc-glycine or Boc-aminocaproic acid). Further deprotection and amide formation with 7 produced bivalent compounds 19, 20, 21, 22, 23 (FIG. 10).

Affinity of Bivalent Inhibitors for c-Myc Monomer.

Figures 1, 11:
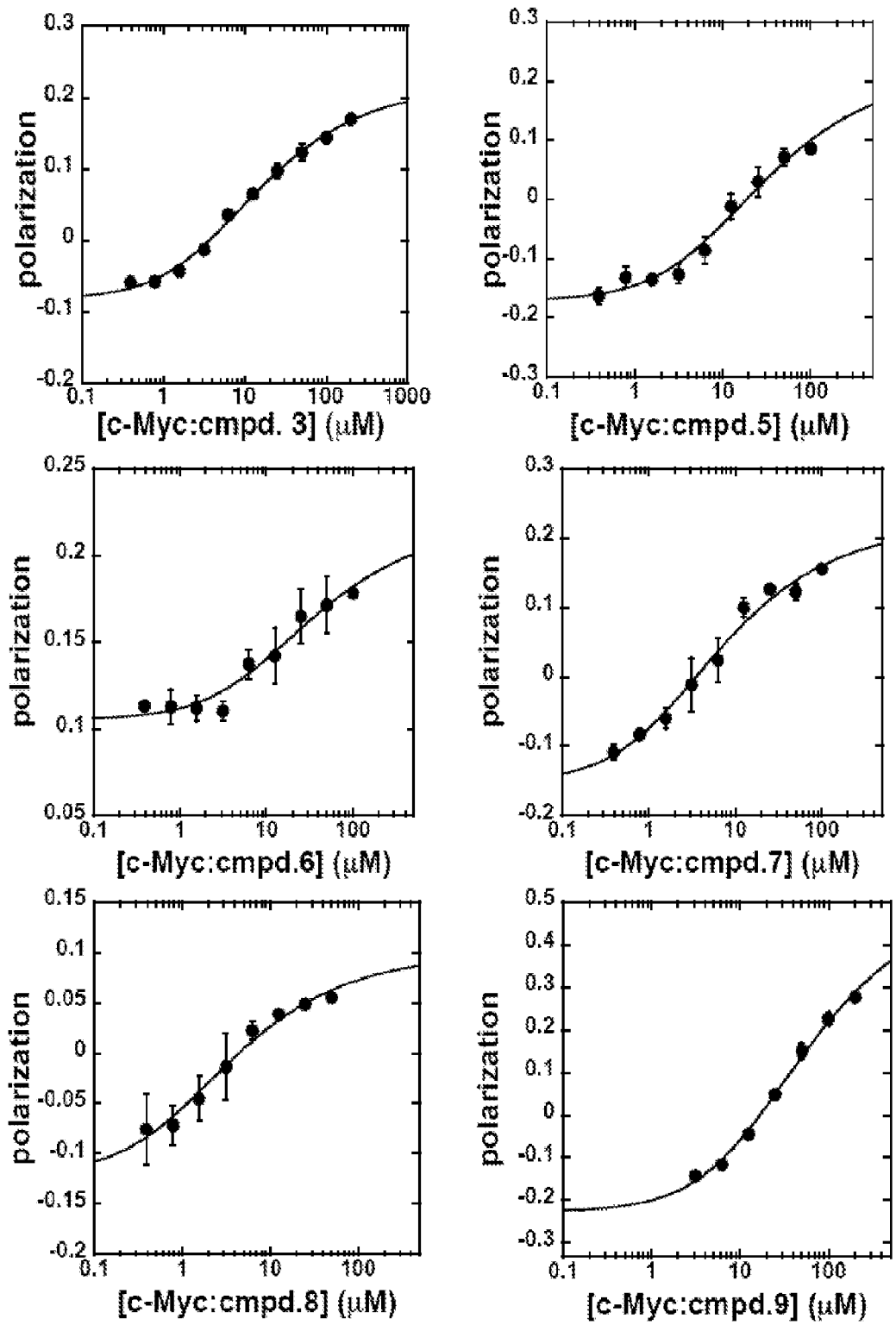
FIG. 11. Fluorescence polarization titrations of binding between c-Myc bHLHZip and the studied compounds. The data shown for compound 15, which lacks intrinsic fluorescence, represent a competition titration where increasing concentrations of this compound displaced the fluorescent parent structure 2 from c-Myc binding. Error bars represent standard error of the mean.
Figures 2, 11:
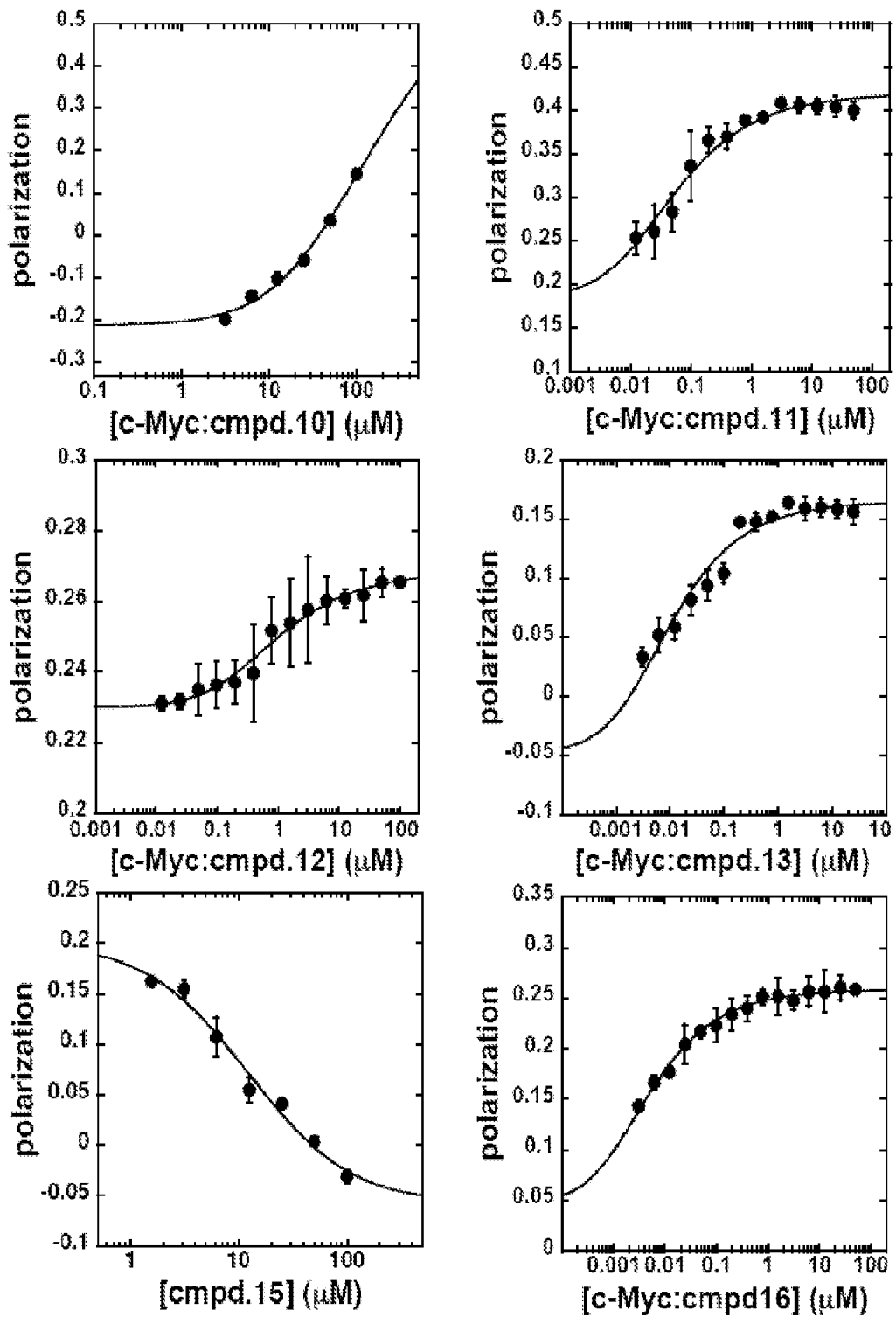
Figures 3, 11:
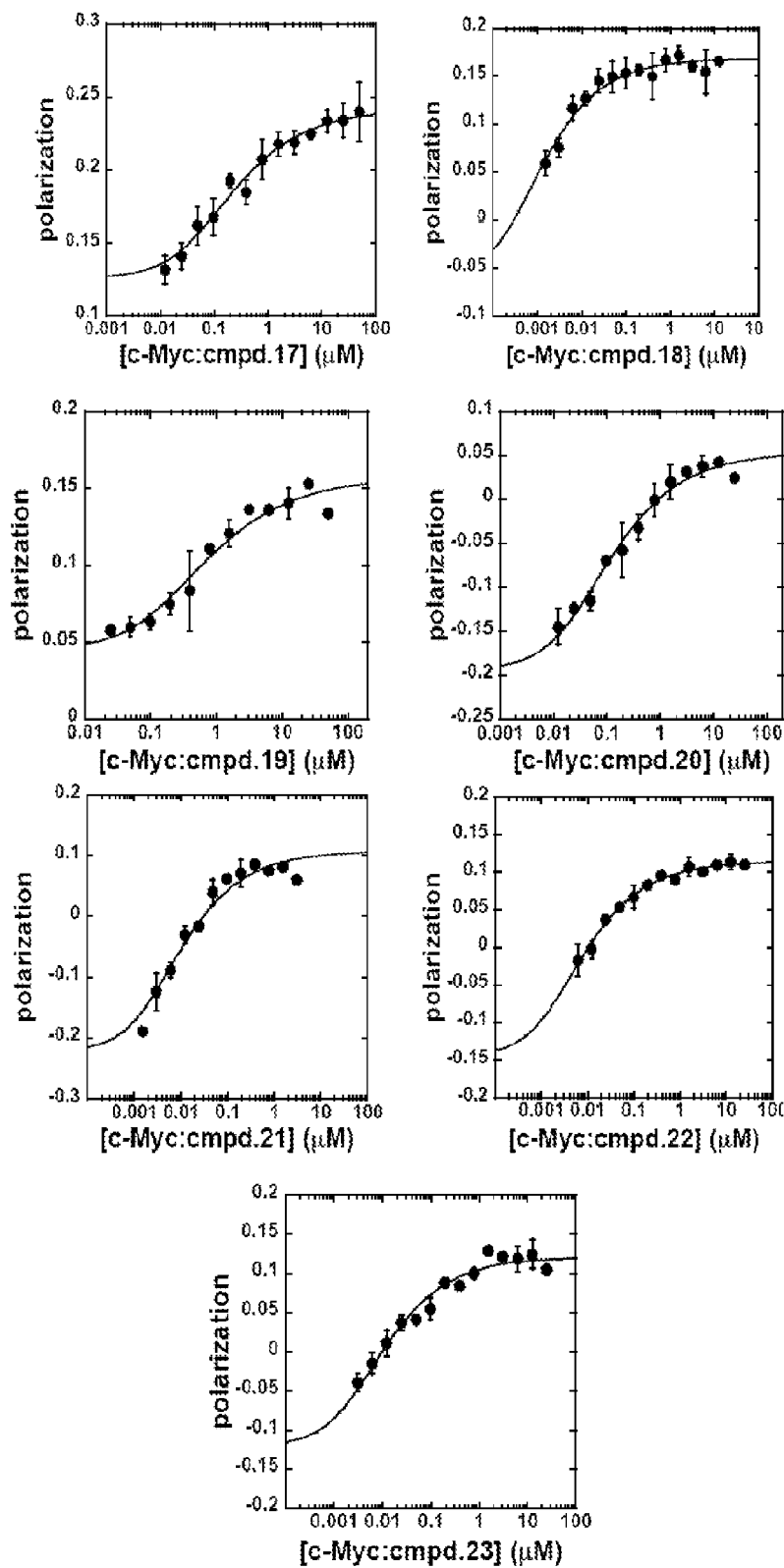

We first measured the binding affinity of the monovalent binding derivatives of the parent compounds 1 and 2 for recombinant monomeric c Myc bHLH-ZIP (amino acids 353-437) in a fluorescence polarization (FP) assay (Park, S. H. et al. *Methods in Molecular Biology* 261, 161-6 (2004)): when a small molecule binds to the bulky peptide its tumbling rate in solution decreases, thus the residual polarization of the emitted light increases. The observed affinities were generally close to those of the parent structures; in the series of amino benzoic acid derivatives of compound 1, namely 5, 6, 7 the para substituted compound 7 bound c-Myc ~5 times tighter than 5 and 6. The effect of the acetylated linker in compound 8 only mildly improved the binding affinity of 7, and, in the case of compound, 10 was actually detrimental on that of 9. In the context of the second explored connection between the linker chain and a derivative of compound 2, due to the low fluorescence of the 2,4-thiazolidinedione derivative compounds compared to the rhodanine derivatives, the c-Myc affinity of 15 was assessed in a competition assay where the displacement of the fluorescent compound 2 from c-Myc binding upon addition of increasing concentrations of 15 was measured. Also in this case the c-Myc binding affinity was little affected by the introduction of the linker chain (Table 1, FIG. 11).

TABLE 1 c-Myc affinities of monovalent and bivalent compounds.

| monovalent | $K_D$ (µM) | bivalent | $K_D$ (nM) |
|---|---|---|---|
| 1 (10074-G5) | 2.8 ± 0.7 | 11 | 24 ± 4 |
| 2 (10058-F4) | 5.7 ± 0.7 | 12 | 400 ± 100 |
| 3 | 7 ± 1 | 13 | 4.7 ± 0.8 |
| 4 | >200 | 16 (linkN1) | 2.2 ± 0.2 |
| 5 | 13 ± 5 | 17 | 110 ± 20 |
| 6 | 16 ± 6 | 18 | 0.6 ± 0.1 |
| 7 | 3 ± 1 | 19 | 320 ± 50 |
| 8 | 1.7 ± 0.9 | 20 | 55 ± 8 |
| 9 | 26 ± 7 | 21 | 4 ± 1 |
| 10 | 90 ± 40 | 22 | 3.6 ± 0.3 |
| 15 | 7 ± 2 | 23 | 5.0 ± 0.8 |

Figure 12:
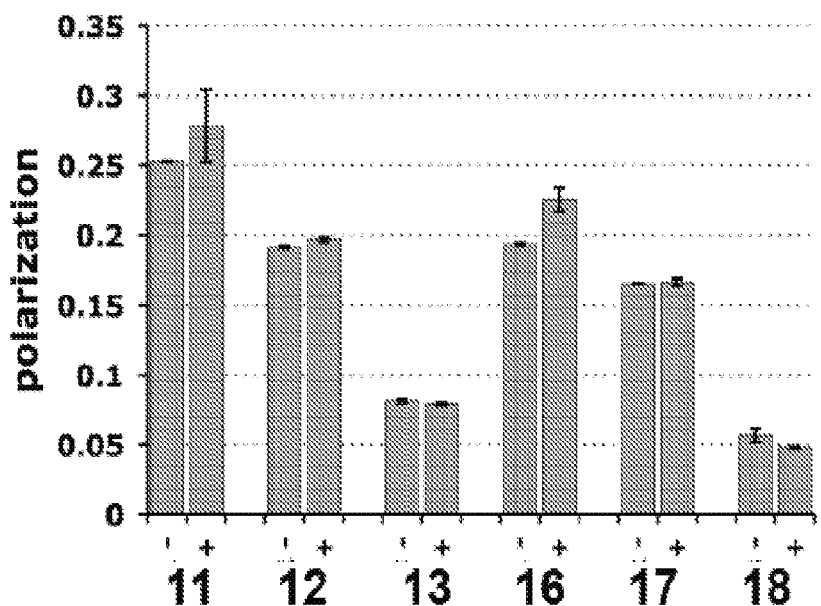
FIG. 12. Control experiments assessing the bivalent c-Myc inhibitors' binding specificity. The inhibitors fluorescence polarization shows little or no increase upon addition of Max p21 isoform (with low homodimerization affinity), indicating that these compounds do not bind to this protein monomer.

We then measured the affinity of the synthesized bivalent inhibitors, by monitoring the FP of the compounds nitrobenzofurazan moiety. The compounds affinities were enhanced by more than 3 orders of magnitude compared to the corresponding monovalent binding unlinked structures, and better than that of c Myc Max dimer formation. It was found that the linker connection by amide formation with the carboxylic group substituting the benzene ring of 9 (compounds 11, 12, 13) resulted in lower affinities than substitution of the 2,4-thiazolidinedione imide nitrogen (compounds 16, 17, 18). With respect to the variations on the compound 2 binding scaffold, the para substituted derivatives displayed the highest affinities and the meta the lowest. The compounds specificities were confirmed by their lack of binding to Max p21 at a concentation of 10 µM Unlike the Max p22 isoform, the p21 Max isoform shows low homodimerization affinity, thus making its disordered monomeric bHLH-ZIP domain an excellent negative control for non-specific binding (FIG. 12). The estimated free energy of binding of the bivalent compounds was roughly proportional to the sum of those of their monovalent components. In the thermodynamic analysis of multivalent binding a $\Delta G^s$ term is used to relate the free energy of binding of a multivalent compound to the sum of those of its monovalent components. This term implies the diverse energy contributions resulting from the linking of independent binding components. The $\Delta G^s$ term generally constitutes a negative contribution to the binding affinity of distinct binding components connected by a flexible linker to a given target. The estimated $\Delta G^s$ for the studied bivalent compounds binding to c-Myc bHLH-ZIP, based on the sum of the affinities of their unlinked components 5, 6 or 7 and 9 or 2, is relatively low, in spite of the lack of optimization of length, chemical nature, and connection site of the linking moiety, suggesting that the flexible nature of the target protein might facilitate the binding of bivalent ligands compared to more rigidly structured binding sites. The low $\Delta G^s$ further indicates that no major loss in conformational entropy of the target protein occurs as a consequence of binding, which seems to involve mainly the localized interaction sites of the parent compounds and only to a minor extent the flexible protein segment connecting them.

The observed binding affinities of the series of bivalent inhibitors with different linker length further supported this mode of binding: variations of the linker length resulted in minor changes in binding affinity—generally a mild loss (with the only exception of compound 19, which displayed considerably reduced binding affinity)—compared to the original series of bivalent compounds with a 6 heavy atoms chain linker. These results suggest that extension of the linker length may allow for an optimal interaction of each binding moiety with its c-Myc site with only limited rotational constraints on the flexible chain connecting them. Correspondingly, the backbone plasticity of the target protein may allow for the correct binding of such moieties when connected by shorter chains.

Structural Study of the Interaction Between c-Myc bHLH-ZIP and a Bivalent Compound.

Figure 5:
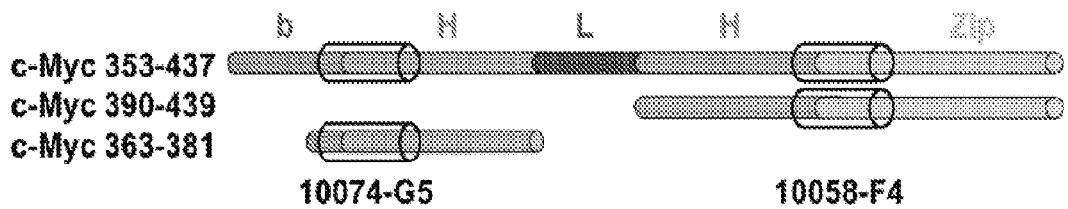
FIG. 5. Bivalent binding scaffolds derived from monovalent inhibitors binding to the intrinsically disordered monomeric c-Myc bHLH-ZIP domain, providing a schematic representation of the recombinant proteins and synthetic peptides encompassing one or both monomeric inhibitors binding sites.

To confirm the occurrence of simultaneous bivalent binding at the expected protein sites, we measured by FP the affinity of linked compounds 11 and 13 for peptides encompassing segments of c-Myc bHLH-ZIP containing the binding site of either 1 (amino acids 363-381) or 2 (amino acids 390-439). The observed affinities correlated well with those of the corresponding unlinked derivatives of 1 and 2 to the full-length c-Myc bHLH-ZIP, confirming that the binding of each component of the linked compounds occurs at the expected site and that the high binding affinity of these molecules actually depends on their bivalent binding to the target protein (FIG. 5, Table 2).

TABLE 2

Binding affinities of bivalent compounds to truncated c-Myc bHLH-ZIP segments. Values are nM.

|    | c-Myc 363-381 | c-Myc 400-439 |
| --- | --- | --- |
| 11 | 10 ± 3 | 122 ± 9 |
| 13 | 0.8 ± 0.6 | 53 ± 16 |

Figure 13:
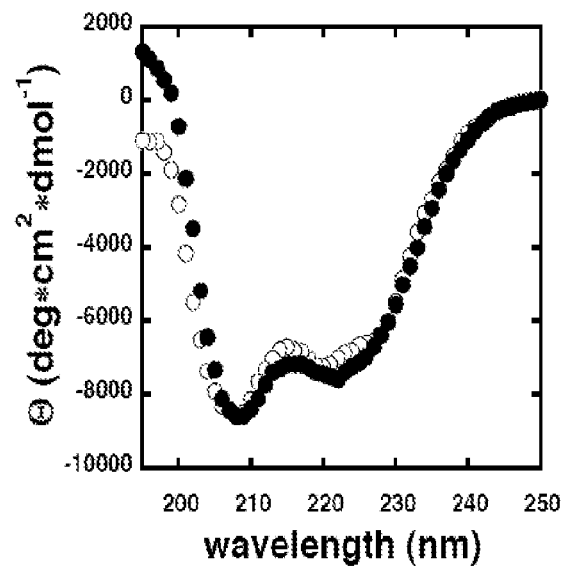
FIG. 13. Circular dichroism (CD) spectrum of 5 μM c-Myc bHLH-ZIP in the absence (white) and presence (black) of 10 μM bivalent compound 18.
Figure 14:
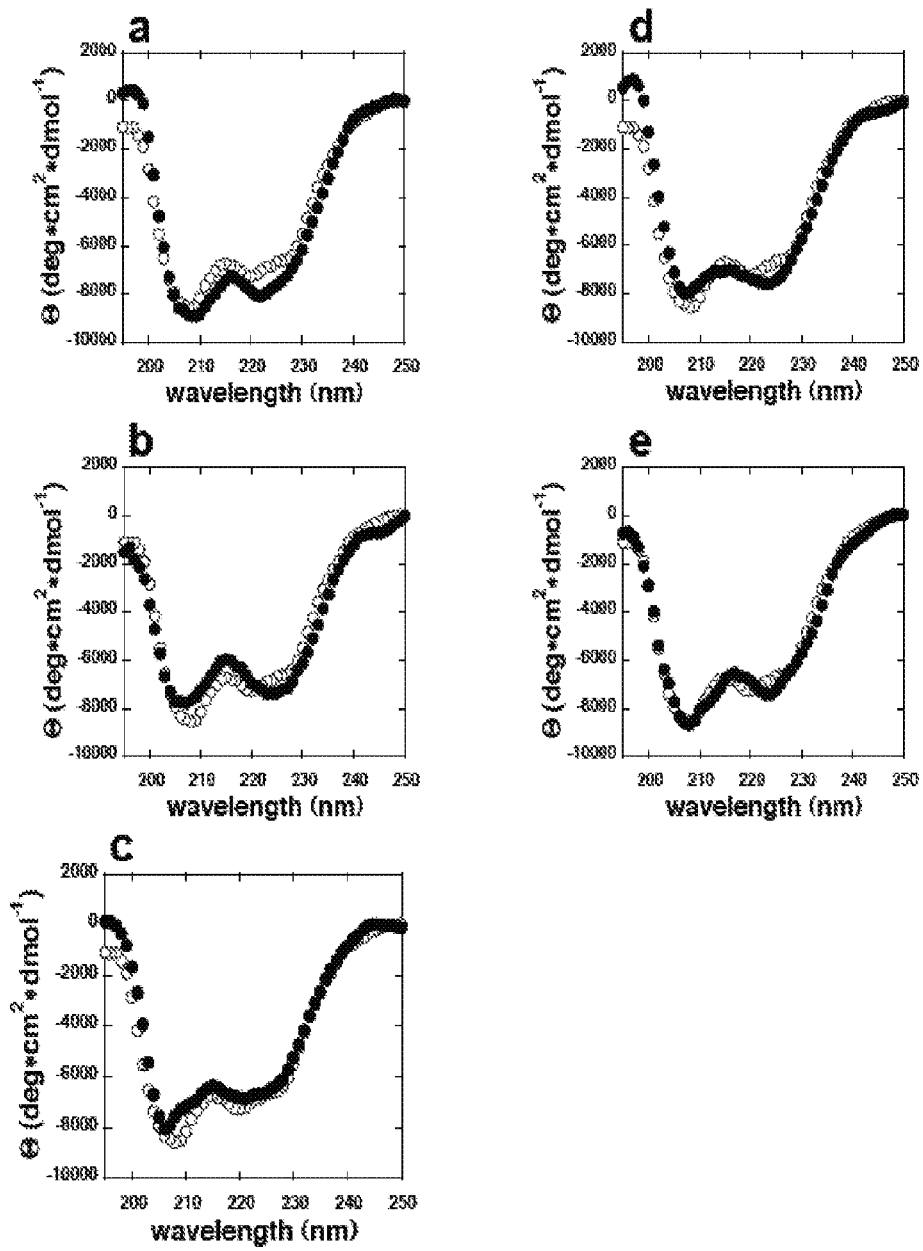
FIG. 14 Circular Dichroism spectra of c-Myc bHLHZip in the absence (white circles) and presence (black circles) of bivalent inhibitors 11(a), 12(b), 13(c), 16(d), 17(e), as shown in FIG. 4 of the main text for compound 18.

We examined the overall effect of bivalent ligands binding to c-Myc bHLH-ZIP by monitoring the circular dichroism (CD) spectrum of this protein in the absence and presence of compounds 11, 12, 13, 16, 17, 18. We had previously observed that the effect of either monovalent compound 1 or 2 on the c-Myc bHLH-ZIP CD spectrum was rather limited: the typical random coil features of this peptide, characterized by low signal intensity and a minimum at ~208 nm (Sreerama, N. et al. *Methods in Enzymology* 383, 318-51 (2004)), were conserved upon binding of either of these compounds. We demonstrated that this behavior is related to the localized nature of the inhibitors binding sites, as conformational rearrangements of the peptide upon ligand binding are limited to a narrow set of amino acids and hard to detect within the CD spectrum of the full length target protein domain, which remains mainly flexible and unstructured (Follis, A. V., et al. *Chemistry & Biology* 15, 1149-1155 (2008)). In the present case of bivalent compounds it is unclear whether the introduced distance constraint between the binding moieties interacting with each protein site would result in more consistent conformational rearrangements over the entire target protein domain. We observed however that binding of any bivalent inhibitor did not result in major changes in shape or intensity of the c-Myc bHLH-ZIP CD spectrum (FIGS. 13 and 14). This result further confirms that the flexible nature of the protein segment between the two binding sites, which seems to facilitate optimal bivalent binding of the studied ligands, is preserved to a large extent when this event occurs.

Figures 1, 15:
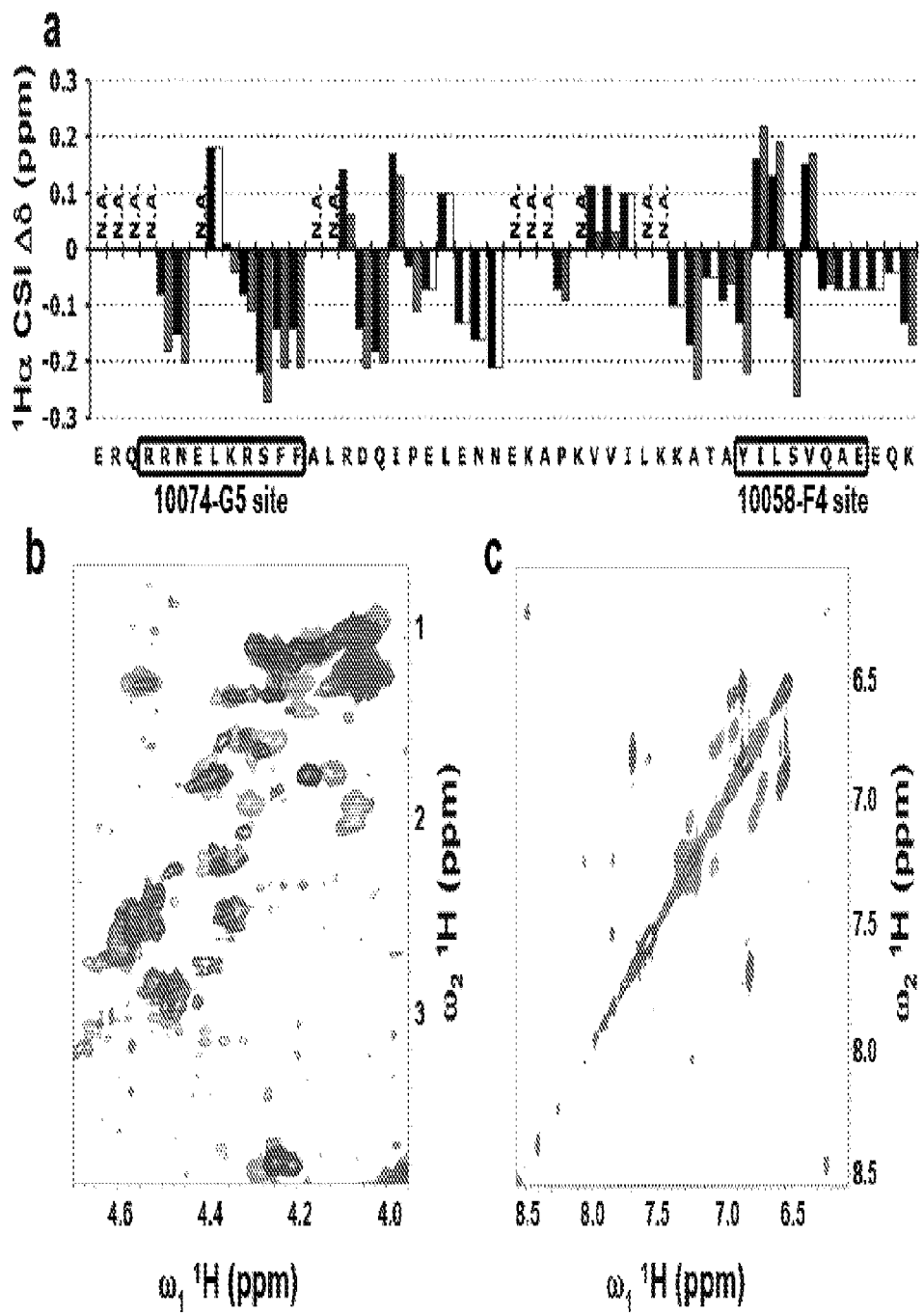
FIG. 15 NMR study of the interaction between c-Myc bHLH-ZIP and compound 18. a. Chemical Shift Indexing analysis of assigned backbone $^1H$ α resonances of c-Myc$_{353-437}$ in the absence (black) and presence (red) of 18 (SEQ ID NO: 1, residues 378-427). b. Overlaid $^1H$ α region of the COSY spectra of pure c-Myc$_{353-437}$ (grey), the same protein in the presence of both 10074-G5 (1) and 10058-F4 (2) (blue), or compound 18 (red). c. Overlaid aromatic region of the COSY spectra of c-Myc$_{353-437}$ in the absence (grey) and presence (red) of 18. d. Schematic mapping of assigned intermolecular NOESY cross-peaks between 18 and protein side chains.
Figures 2, 15:
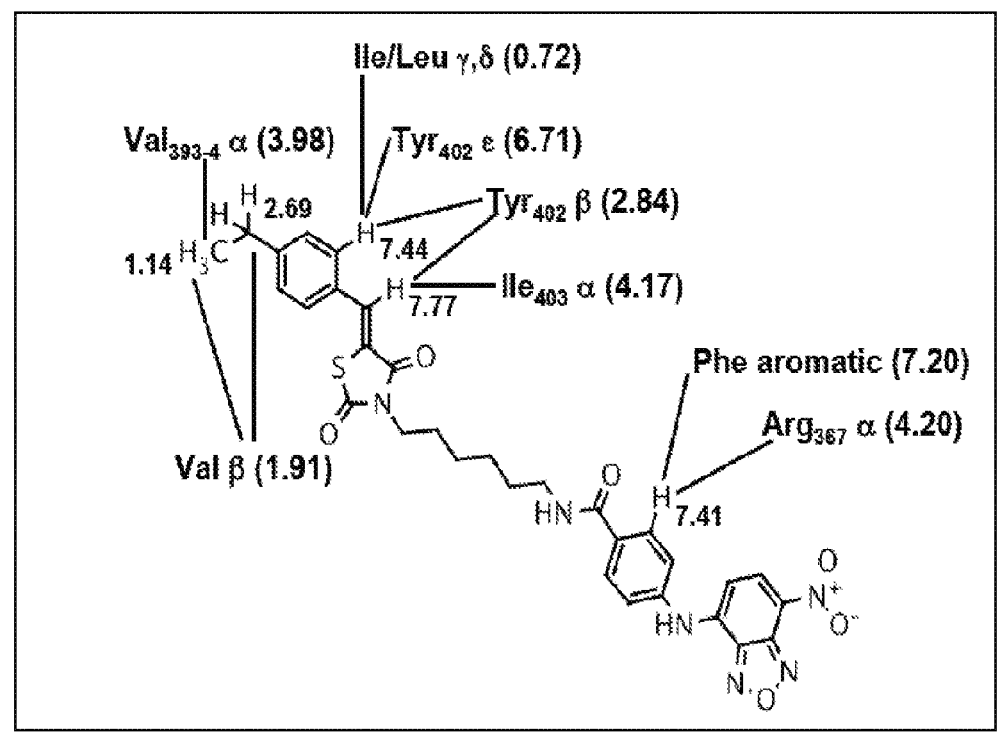
Figure 16:
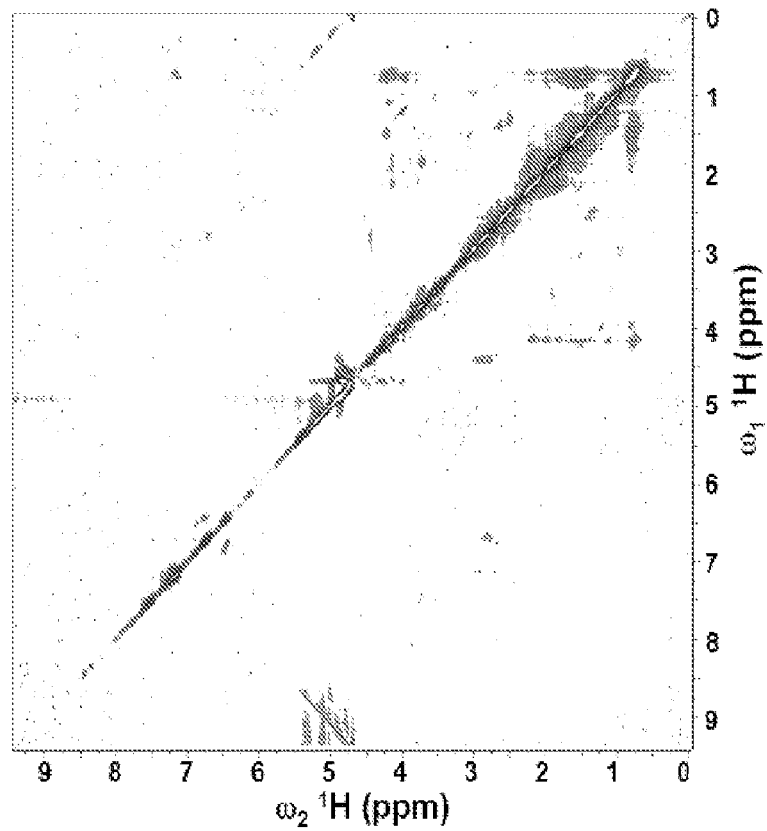
FIG. 16. NOESY NMR spectrum of c-Myc353-437 in the presence of compound 18.

We obtained further structural insight on the c-Myc interaction of 18, the compound with the highest affinity for this protein target, by means of analyzing the effects of binding on c-Myc backbone α $^1$H NMR signals. The magnetic field distribution of these signals is coherently associated with the secondary structure of each amino acid, and their change in shift upon a molecular event such as ligand binding can be related to conformational rearrangements associated with it. Other effects on backbone chemical shift signals, unrelated to conformational changes, might be induced by shielding effects dependent on the different chemical environment in proximity of an amino acid upon ligand binding. In both cases changes in backbone chemical shift can help identify residues directly involved in a binding interaction. In the case of the unbound ID c-Myc bHLH-ZIP monomer, the α $^1$H backbone resonances were only partially assigned, but to a satisfactory extent for the sequence regions spanning the binding sites of 1 and 2, thanks to the low redundancy of several amino acids found within these segments. The chemical shift pattern of the assigned resonances is typical of ID protein regions, and does not display extended segments with a consistent secondary structure trend, suggesting instead the presence of residual structure at a local level. Upon addition of 18, changes in the $\alpha^1$H signals of several residues within the binding sites of both 1 and 2, including respectively Phe$_{374-375}$ and Tyr$_{402}$, were observed (FIG. 15A). Similar changes in the Tyr$_{402}$ aromatic signals to those induced upon binding of 2 were also observed (FIG. 15b). Comparison of COSY spectra of the α $^1$H region of c-Myc in the presence of 18 or both 1 and 2 simultaneously further suggested that the overall interaction of the first molecule with the target protein results in a pattern of chemical shift changes that closely resembles that induced by the independent and simultaneous binding of the two latter (FIG. 15c). The NOESY spectrum of c-Myc bHLH-ZIP in the presence of 18 shows a series of intermolecular cross-peaks that involve the same residues or proximal ones to those whose backbone resonances are affected by this compound's binding (FIGS. 15d and 16).

Efficacy of Bivalent c-Myc-Max Inhibitors.

Figure 17:
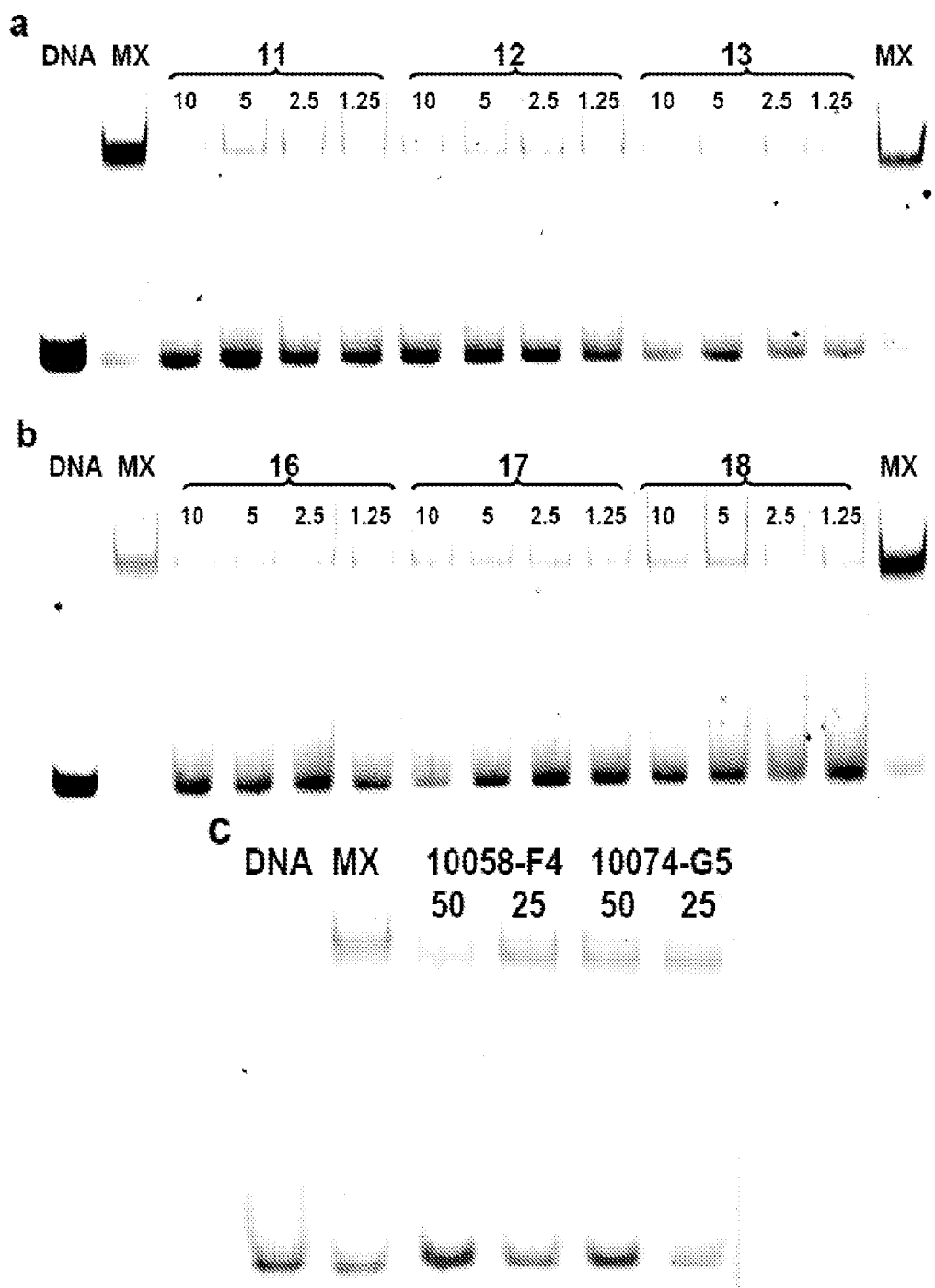
FIG. 17. Inhibition of c-Myc-Max DNA binding measured by electrophoretic mobility shift assay (EMSA). a. Inhibition by bivalent compounds 11, 12, 13. b. Inhibition by bivalent compounds 16, 17, 18. c. Inhibition by monovalent compounds 10074-G5 (1) and 10058-F4 (2). Inhibitor concentrations are micromolar. The c-Myc-Max dimer concentration was 1 μM in a and b, 50 nM in c.
Figure 18:
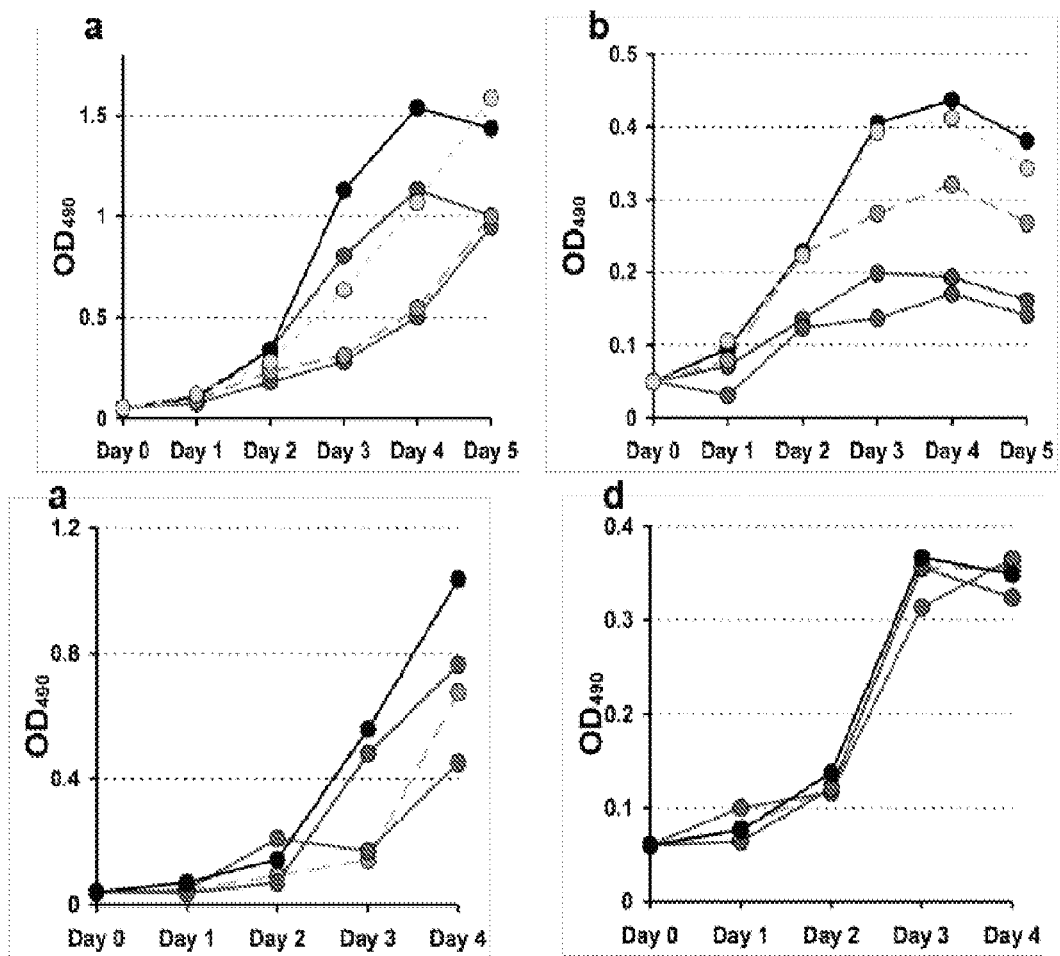
FIG. 18. Compound 16 (linkN1) cell growth inhibition for HL60 (a), Burkitt's lymphoma (b), TGR1 (c) and c-Myc knockout (d) cells. Black: cell growth in the absence of inhibitor, blue: +40 μM 10058-F4 (2); red: +4 μM (d), 2 μM (a, c) or 1 μM (b) linkN1; orange: +2 μM (d), 1 μM (a, c) or 500 nM (b) linkN1; yellow+500 nM (a) or 200 nM (b) linkN1.
Figure 19:
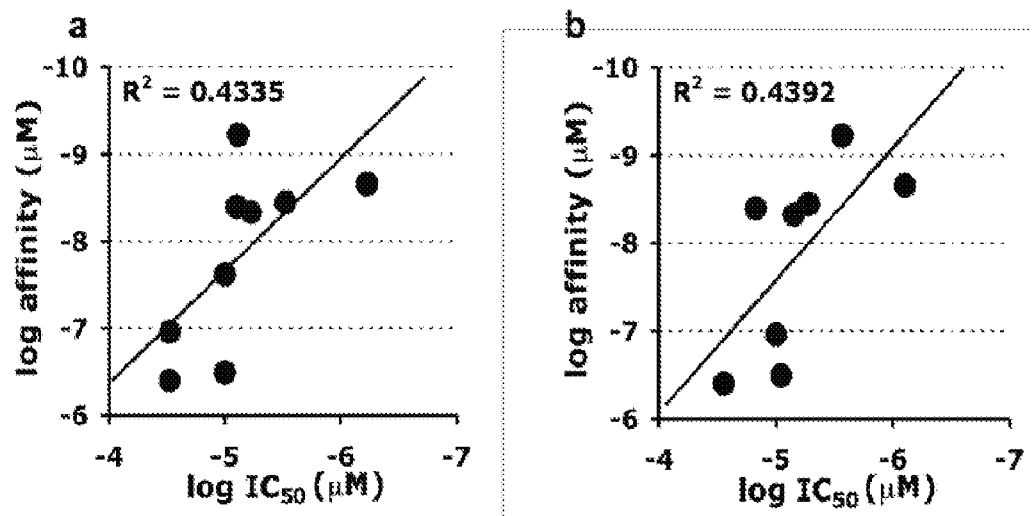
FIG. 19. Correlation between c-Myc binding affinity and growth inhibition of HL60 (a) or Burkitt's lymphoma (b) cells for the studied bivalent inhibitors.
Figure 20:
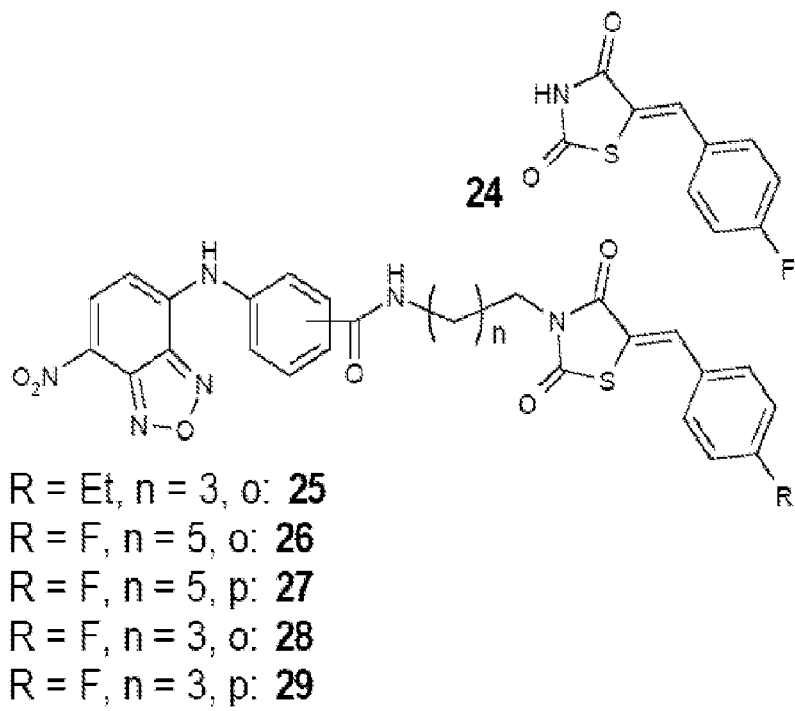
FIG. 20. New building block derivative of 2 and second group of bivalent inhibitors.
Figure 21:
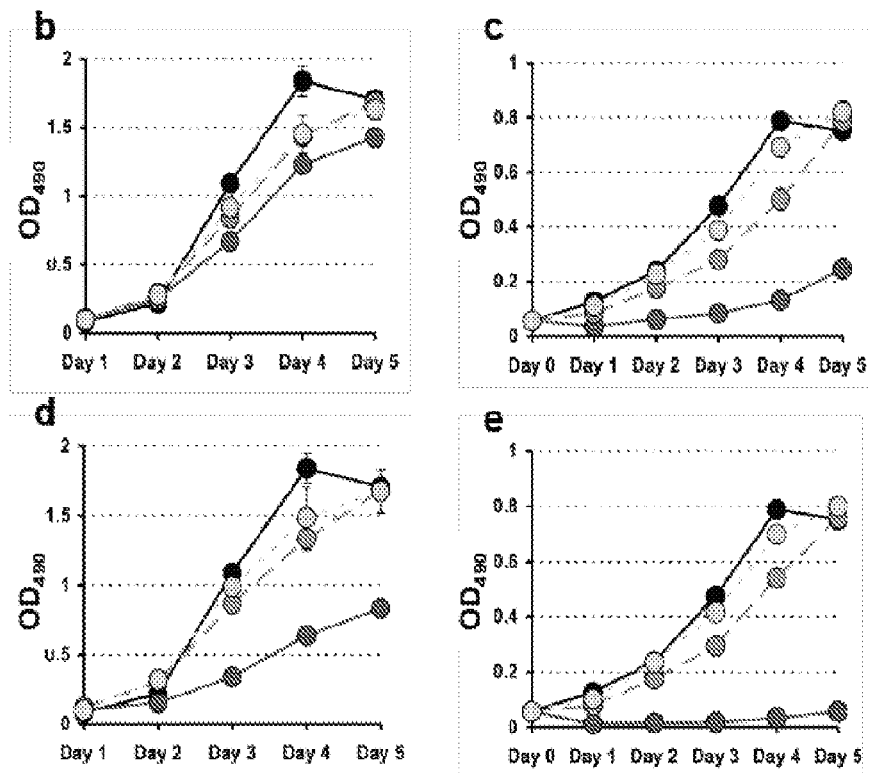
FIG. 21. Activity data for the second group of bivalent inhibitors (25-29). a. Fluorescence polarization titrations of c-Myc binding. Inhibition of HL60 (b) and BL (c) cell growth by compound 27. Inhibition of HL60 (d) and BL (e) cell growth by compound 28 (red: +2 μM inhibitor; orange: +1 μM inhibitor; yellow: +0.5 μM inhibitor; black: DMSO only).

We evaluated the efficacy of the linked compounds 11, 12, 13, 16, 17, 18 in inhibiting the c-Myc-Max interaction by measuring the binding of a target DNA sequence (E-Box) by the protein heterodimers in an electrophoretic mobility shift assay (EMSA). Strong disruption of DNA binding was observed in all cases at higher protein concentrations and lower inhibitor concentrations than those required in similar experiments performed with the parent compounds 1 and 2, demonstrating the appeal of the bivalent binding approach to enhance the inhibition of c-Myc function by small molecules (FIG. 17). We have previously shown that 1, 2 and numerous analogs of 2 can specifically inhibit the growth of c-Myc-dependent human cancer cell lines but exert substantially less effect on the growth of c-Myc knockout cells. Several analogs of 2 have also been previously identified as being 5-8-fold more potent than the parental compound in both HL60 promyelocytic cells (Leglise, M. C. et al. *Blood Cells* 13, 319-37 (1988)) and Burkitt lymphoma (BL) cells (Li, Z. et al. *Proc. Nat'l Acad. Sci.* (*USA*) 100, 8164-9 (2003)) and these values generally correlated with those obtained using purified recombinant proteins in FP and EMSA based assays. We therefore tested the bivalent compounds for growth inhibition of HL60 and BL cells, and found that most compounds outperform the parent compounds in this assay. Several of the compounds were found to be quite potent and significantly better than 1, 2 or any of the former compounds' previously tested analogs. Of these, the best was compound 16 (LINK N1), with an $IC_{50}$ in the 0.5-1.0 μM in both of the above cell lines. In contrast, higher concentrations of the compounds were required to inhibit the growth of the non-transformed rat fibroblast line TGR1 or of TGR1-derived c-Myc null rat fibroblasts reconstituted with either of the c-Myc target genes HMGA1b or MT-MC1, which restore a normal growth rate. These results indicate that the studied bivalent compounds are specifically growth inhibitory for cells expressing the highest levels of c-Myc (Table 3, FIG. 18). The lower, albeit promising, potency of the bivalent inhibitors in cell based assays compared to ones involving purified components, and the partial lack of correlation between the first and the latter, may reflect a generally poor cell permeability of these compounds, which are relatively bulky and display higher than optimal polar surface areas. The effects of the linker chain connectivity on the compounds conformation and shape may also affect their cell permeability in a different manner from what observed for their c-Myc binding affinity, resulting in the aforementioned incomplete correlation between their performance in cell based and purified components assays (FIG. 19). Five additional bivalent inhibitors were promptly synthesized with the goal of evaluating the dependance of the molecules' poor activity against cancer cell growth on their cell permeability and metabolic stability. A fluorinated substitute of 14, 24, the choice of which was based upon the results of structure activity relationship studies described in Wang, H. et al. (*Mol. Cancer Ther.* 6, 2399-408 (2007)), was employed at this purpose (Muller, K., et al. *Science* 317, 1881-6 (2007) and Kirk, K. L. *Current Topics in Medicinal Chemistry* 6, 1447-56 (2006)). The obtained compounds, 25, 26, 27, 28, 29 (FIG. 20) display on average lower molecular weights and polar surface areas than the first group of bivalent compounds (589 vs. 657 and 188.6 vs. 226.6 respectively—compound 21 was included in the new set of inhibitors in these statistics), and the metabolic stability of their binding moiety derived from compound 2, previously demonstrated to be low (Guo, J. et al. *Cancer Chemoterapy and Pharmacology* 63, 615-625 (2009)), is likely to be improved as well (Muller, K., et al. *Science* 317, 1881-6 (2007) and Kirk, K. L. *Current Topics in Medicinal Chemistry* 6, 1447-56 (2006)). The c-Myc affinities of compounds 25, 26, 27, 28, 29, as measured by FP, were slightly lower than those of corresponding bivalent compounds from the first group, their inhibitory potencies against the growth of HL60 and BL cells were however on average twice as high as those of the previously tested compounds, although none of the new molecules outperformed compound 16-LINK N1 (Table 4, FIG. 21). The consistently promising activity of the last group of bivalent compounds suggests that the scaffold of molecule 24 might be chosen as a starting point for further optimization of bivalent inhibitors.

TABLE 3

Growth inhibition of HL60 and Burkitt's Lymphoma c-Myc dependent cancer cell lines by bivalent compounds. Values are μM.

|   |           | HL60    | BL      |
|---|-----------|---------|---------|
| 1 | (10074-G5)| 25      | 20      |
| 2 | (10058-F4)| 50      | 40      |
| 11|           | >10     |         |
| 12|           | >30     | 20-35   |
| 13|           | 6       | 5-10    |
| 16| (linkN1)  | 0.5-0.7 | 0.7-0.9 |
| 17|           | >30     | >10     |
| 18|           | 7-9     | 2-4     |
| 19|           | 7-13    | 7-11    |
| 21|           | 7-9     | 14-16   |
| 22|           | 2-4     | 4-6     |

TABLE 4 c-Myc affinities and cell line growth inhibition of the second group of bivalent compounds.

|    | $K_D$ (nM)  | HL60 (μM) | BL (μM) |
|----|-------------|-----------|---------|
| 25 | 3.0 ± 0.5   | 2-6       | 2-2.5   |
| 26 | 4.6 ± 0.8   | 3-3.5     | 6-8     |
| 27 | 1.7 ± 0.4   | 3-4       | 1.2     |
| 28 | 11 ± 2      | 1.5-1.7   | 1-1.2   |
| 29 | 3.6 ± 0.6   | 6-10      | 6-7     |

Growth inhibition of HL60 cells correlates with reductions in c-Myc-Max heterodimers.

Figure 22:
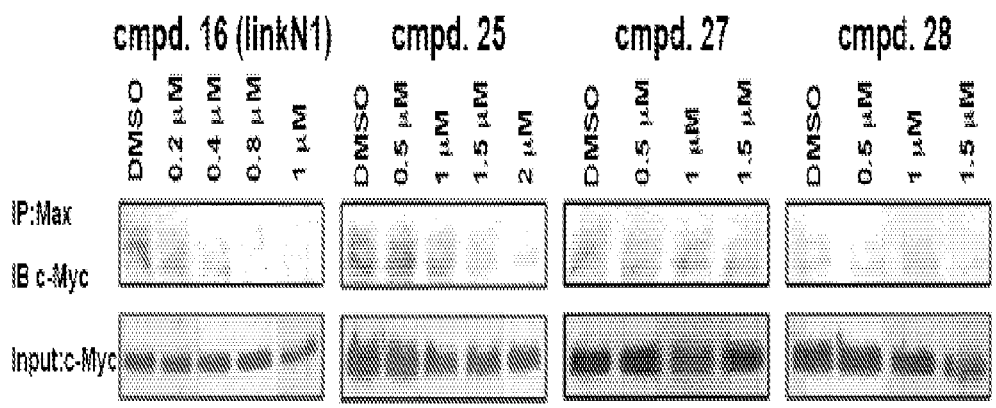
FIG. 22. Co-immunoprecipitation assays with the four most potent bivalent compounds. HL60 cells were incubated for 6 hr with the indicated concentration of each compound. 10058-F4 at the indicated concentration was used as a control. Total cell lysates were then prepared and precipitated with an anti-Max antibody. The immuno-precipitate was then subjected to SDS-PAGE and immunolotting with an anti-c-Myc mAb as previously described.

To determine whether the disruption of c-Myc-Max heterodimers by bivalent compounds observed with recombinant proteins (FIG. 22) could be reproduced in cultured cells in a manner than correlated with growth inhibition, HL60 cells were incubated for 6 hours with serial dilutions of the four most effective bivalent compounds (Tables 3, 4). Equivalent numbers of cells were then lysed and subjected to immunopecipitation with an anti-Max antibody (Zhang, H., et al. *J. Biol. Chem.* 272, 17416-24 (1997)) followed by SDS-PAGE and immunoblotting with an anti-c-Myc mAb. As seen in FIG. 22, all four bivalent compounds were highly effective in preventing and/or disrupting the c-Myc-Max association in a concentration-dependent manner. In general the concentrations of compounds required to achieve a >50% dissociation between c-Myc and max were in good agreement with the concentrations needed to inhibit cell growth. Interestingly, the incubation times required to observe disruption of c-Myc-Max dimer formation were considerably shorter than previously observed for monovalent inhibitors (16 hours, Wang, H. et al. *Mol. Cancer Ther.* 6, 2399-408 (2007)), suggesting that faster disruption kinetics may be associated with bivalent binding. Longer incubation times (>16 hours) resulted in decreased inhibitory effect of the studied bivalent compounds on c-Myc-Max dimerization as detected by this technique, suggesting low metabolic stability of these molecules. This indication is in agreement with metabolic stability data obtained for their monovalent counterparts.

Spectroscopic Information:

The following are exemplary data for compounds 12 and 16. Data not shown for compounds 1-37; Boc-38; 39; 40; tert butyl N-(5-acetamidopentyl)carbamate; tert-butyl N-{5-[(4-{[(5Z)-4-oxo-2-sulfanylidene-1,3-thiazolidin-5-ylidene]methyl}phenyl)formamido]pentyl}carbamate; tert-butyl N-{6-[(5Z)-5-[(4-ethylphenyl)methylidene]-2,4-dioxo-1,3-thiazolidin-3-yl]hexyl}carbamate; tert-butyl N-[2-({6-[(5Z)-5-[(4-ethylphenyl)methylidene]-2,4-dioxo-1,3-thiazolidin-3-yl]hexyl}carbamoyl)phenyl]carbamate; tert-butyl N-[({5-

[(4-{[(5Z)-4-oxo-2-sulfanylidene-1,3-thiazolidin-5-ylidene] methyl}phenyl)formamido]pentyl}carbamoyl)methyl] carbamate; tert-butyl N-[5-({5-[(4-{[(5Z)-4-oxo-2-sulfanylidene-1,3-thiazolidin-5-ylidene]methyl}phenyl) formamido]pentyl}carbamoyl)pentyl]carbamate; tert-butyl N-{4-[(5Z)-5-[(4-ethylphenyl)methylidene]-2,4-dioxo-1,3-thiazolidin-3-yl]butyl}carbamate; tert-butyl N-[({6-[(5Z)-5-[(4-ethylphenyl)methylidene]-2,4-dioxo-1,3-thiazolidin-3-yl]hexyl}carbamoyl)methyl]carbamate; 2-amino-N-{6-[(5Z)-5-[(4-ethylphenyl)methylidene]-2,4-dioxo-1,3-thiazolidin-3-yl]hexyl}acetamide; tert-butyl N-[5-({6-[(5Z)-5-[(4-ethylphenyl)methylidene]-2,4-dioxo-1,3-thiazolidin-3-yl]hexyl}carbamoyl)pentyl]carbamate; 1TZD-C4-2BnNHBoc tert-butyl N-[2-({4-[(5Z)-5-[(4-ethylphenyl) methylidene]-2,4-dioxo-1,3-thiazolidin-3-yl] butyl}carbamoyl)phenyl]carbamate; tert-butyl N-{6-[(5Z)-5-[(4-fluorophenyl)methylidene]-2,4-dioxo-1,3-thiazolidin-3-yl]hexyl}carbamate; tert-butyl N-{4-[(5Z)-5-[(4-fluorophenyl)methylidene]-2,4-dioxo-1,3-thiazolidin-3-yl] butyl}carbamate; and tert-butyl N-[2-({4-[(5Z)-5-[(4-fluorophenyl)methylidene]-2,4-dioxo-1,3-thiazolidin-3-yl] butyl}carbamoyl)phenyl]carbamate.

N-[5-({3-[(7-nitro-2,1,3-benzoxadiazol-4-yl)amino] phenyl}formamido)pentyl]-4-{[(5Z)-4-oxo-2-sulfanylidene-1,3-thiazolidin-5-ylidene] methyl}benzamide (12)

UV/Vis (solvent: ethanol): $\lambda_{max}$ 466 nm; Emission $\lambda_{max}$ 560 nm (ex. 466 nm);
$^1$H NMR (300 MHz, CDCl$_3$): δ (ppm) 8.43 (d, J=8.7 Hz, 1H), 8.03 (s, 1H), 8.00 (d, J=7.8 Hz, 1H), 7.86 (d, J=8.1 Hz, 2H), 7.60 (d, J=7.8 Hz, 1H), 7.56 (s, 1H), 7.53 (d, J=7.8 Hz, 2H), 7.48 (t, J=7.8 Hz, 1H), 6.73 (d, J=8.7 Hz, 1H), 6.68 (bs, 1H), 4.82-4.65 (bs, 1H), 4.65-4.58 (bs, 1H), 3.47 (dt, J$^1$=6.6 Hz, J$^2$=7.2 Hz, 1H), 3.37 (dt, J$^1$=6.6 Hz, J$^2$=7.2 Hz, 1H), 3.13 (t, J=7.2 Hz, 2H), 1.65 (qt, J=7.2 Hz, 2H), 1.52 (qt, J=7.2 Hz, 2H), 1.18 (qt, J=7.2 Hz, 2H);
$^{13}$C NMR—$^1$H decoupled (75 MHz, DMSO d$_6$): δ (ppm) 198.0, 184.9, 182.9, 175.1, 166.7, 165.3, 158.0, 155.6, 153.6, 151.8, 148.6, 145.5, 145.0, 144.4, 142.9, 138.3, 134.1, 132.3, 127.8, 124.0, 122.4, 77.1, 57.2, 42.5, 34.8, 25.2, 23.5;
ESI-MS (m/z), solvent H$_2$O: 325.1 ([m+1*H$_2$O]$^{2+}$).

N-{6-[(5Z)-5-[(4-ethylphenyl)methylidene]-2,4-dioxo-1,3-thiazolidin-3-yl]hexyl}-2-[(7-nitro-2,1,3-benzoxadiazol-4-yl)amino]benzamide amine (16, LinkN1)

UV/Vis (solvent: ethanol): $\lambda_{max}$ 466 nm; Emission $\lambda_{max}$× 550 nm (ex. 466 nm);
$^1$H NMR (300 MHz, CDCl$_3$): δ (ppm) 8.61 (d, J=8.4 Hz, 1H), 8.48 (d, J=7.5 Hz, 1H), 7.67 (d, J=7.8 Hz, 2H), 7.62 (t, J=7.5 Hz, 2H), 7.60 (s, 1H), 7.52 (d, J=8.4 Hz, 1H), 7.42 (d, J=7.8 Hz, 2H), 7.31 (d, J=7.5 Hz, 1H), 3.49 (m, 1H), 3.41 (dt, J$^1$=6.0 Hz, J$^2$=6.9 Hz, 2H), 3.15 (m, 1H), 2.70 (q, J=7.5 Hz, 2H), 2.27 (m, 1H), 1.87 (m, 1H), 1.62 (qt, J=6.9 Hz, 2H), 1.39 (qt, J=6.9 Hz, 2H), 1.28 (m, 2H), 1.25 (t, J=7.5 Hz, 3H);
$^{13}$C NMR—$^1$H decoupled (75 MHz, CDCl$_3$): δ (ppm) 183.2, 175.5, 166.6, 158.7, 154.2, 153.3, 151.4, 145.2, 141.4, 137.6, 137.1, 133.4, 130.3, 129.5, 128.4, 120.3, 116.3, 116.0, 109.1, 97.4, 80.9, 40.9, 35.2, 29.5, 29.2, 26.3, 25.3, 17.4, 15.8.
ESI-MS (m/z), solvent H$_2$O: 615.8 ([m+1]$^+$).

DISCUSSION

We have designed a new generation of compounds with the intent of achieving bivalent binding to the intrinsically disordered monomeric bHLH-ZIP domain of c-Myc.

Figure 23:
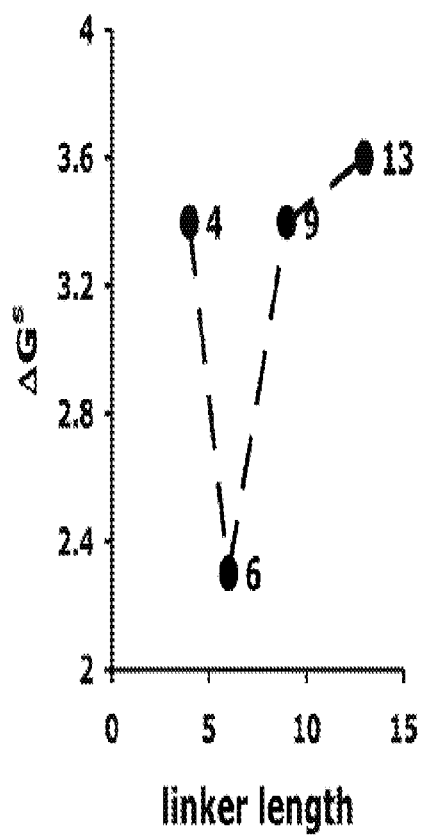
FIG. 23. Effect of linker chain length on c-Myc binding affinity for the series of bivalent inhibitors 18, 21, 22, 23.
Figure 24:
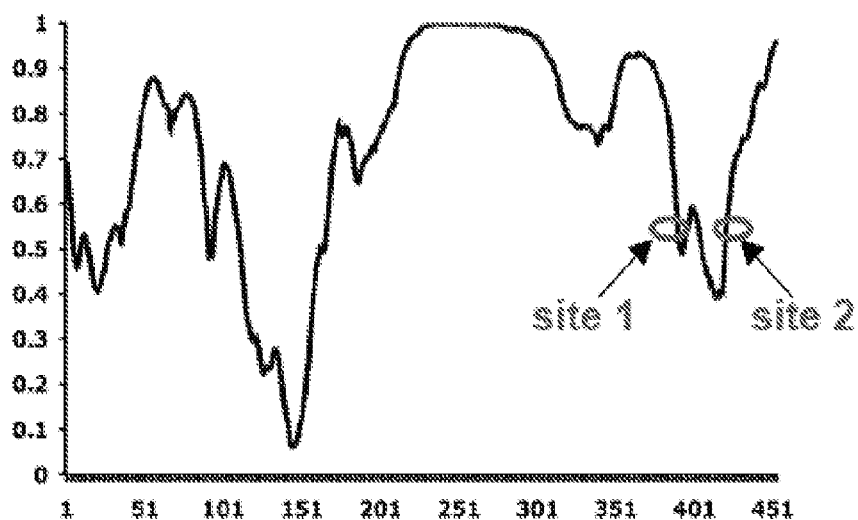
FIG. 24. Prediction of disordered regions with the PONDR VSL2 algorithm for the full sequence of three, biologically relevant, intrinsically disordered proteins: c-Myc, MDM2 and Amyloid beta (A4) precursor protein (APP). The pattern of narrow regions with low disorder probability, observed within the c-Myc bHLHZip domain in correspondence of the sites exploited here for bivalent binding, is consistently found over the sequence of these three proteins. Shaded areas indicate natively folded domains.
Figure 1:
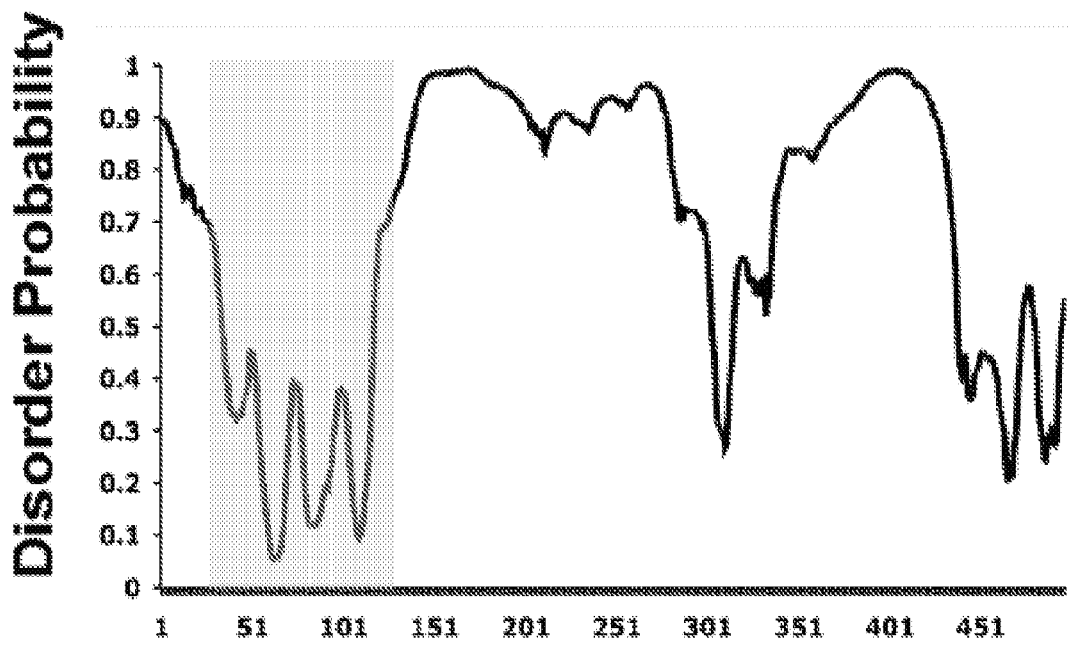
Figures 2, 24:
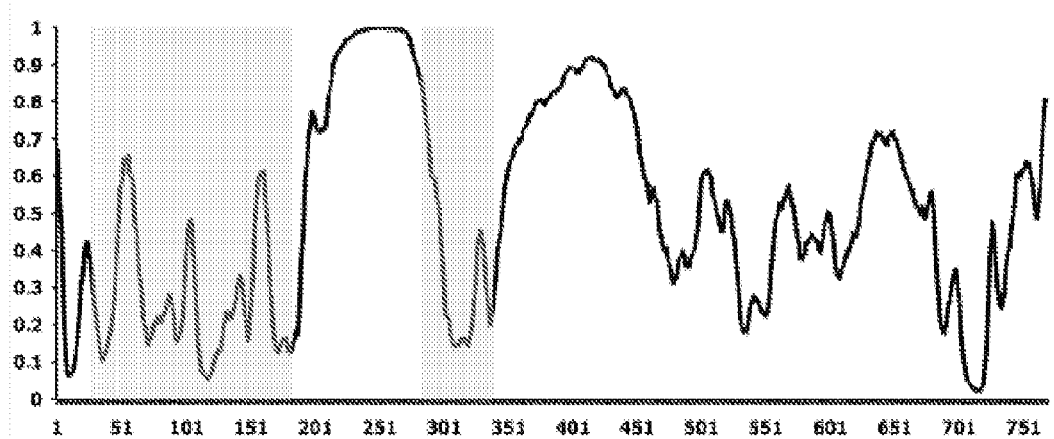
Figures 1, 25:
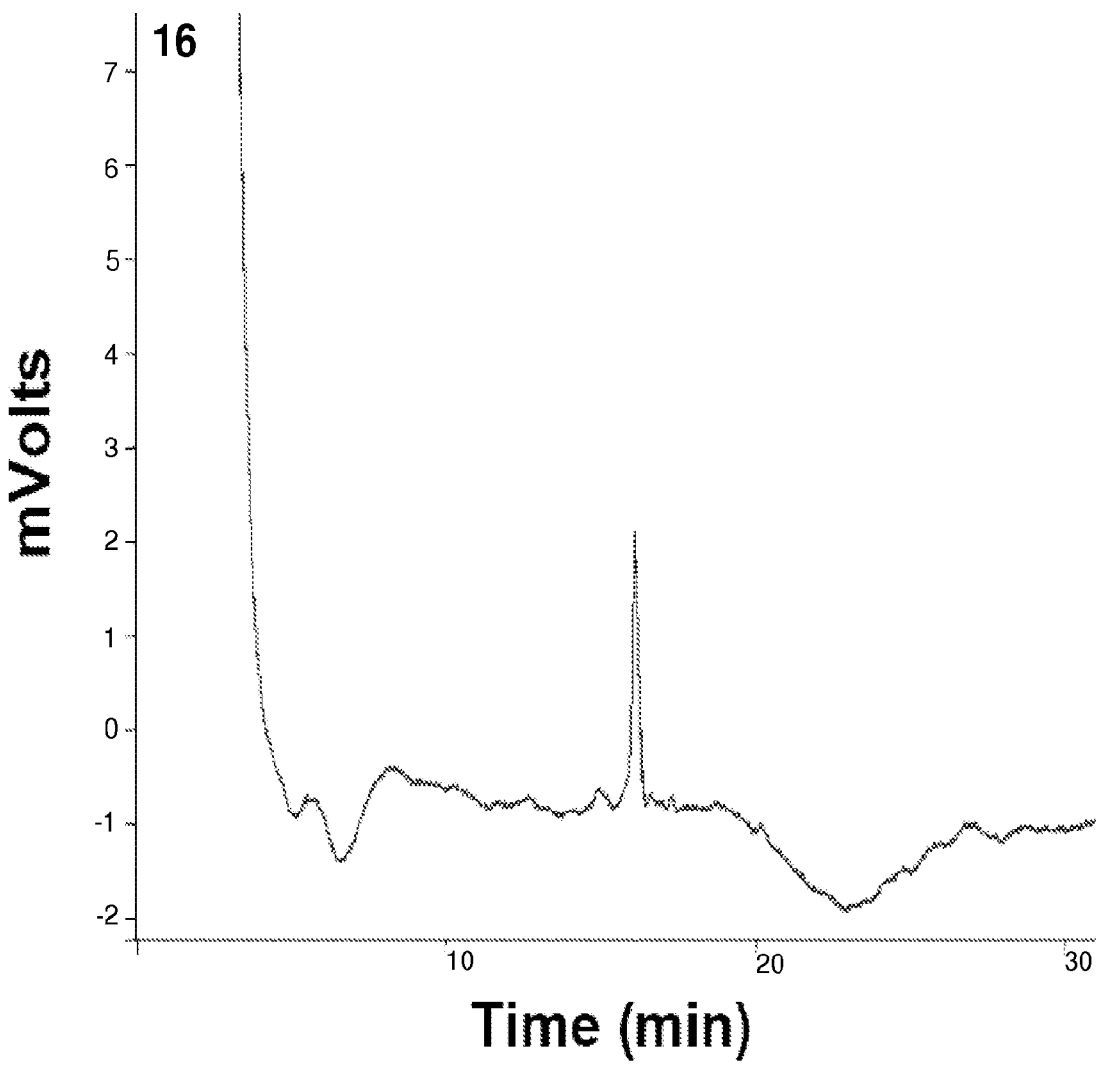
FIG. 25. HPLC traces of examples of bivalent inhibitors (compounds 12 and 16 shown).
Figures 2, 25:
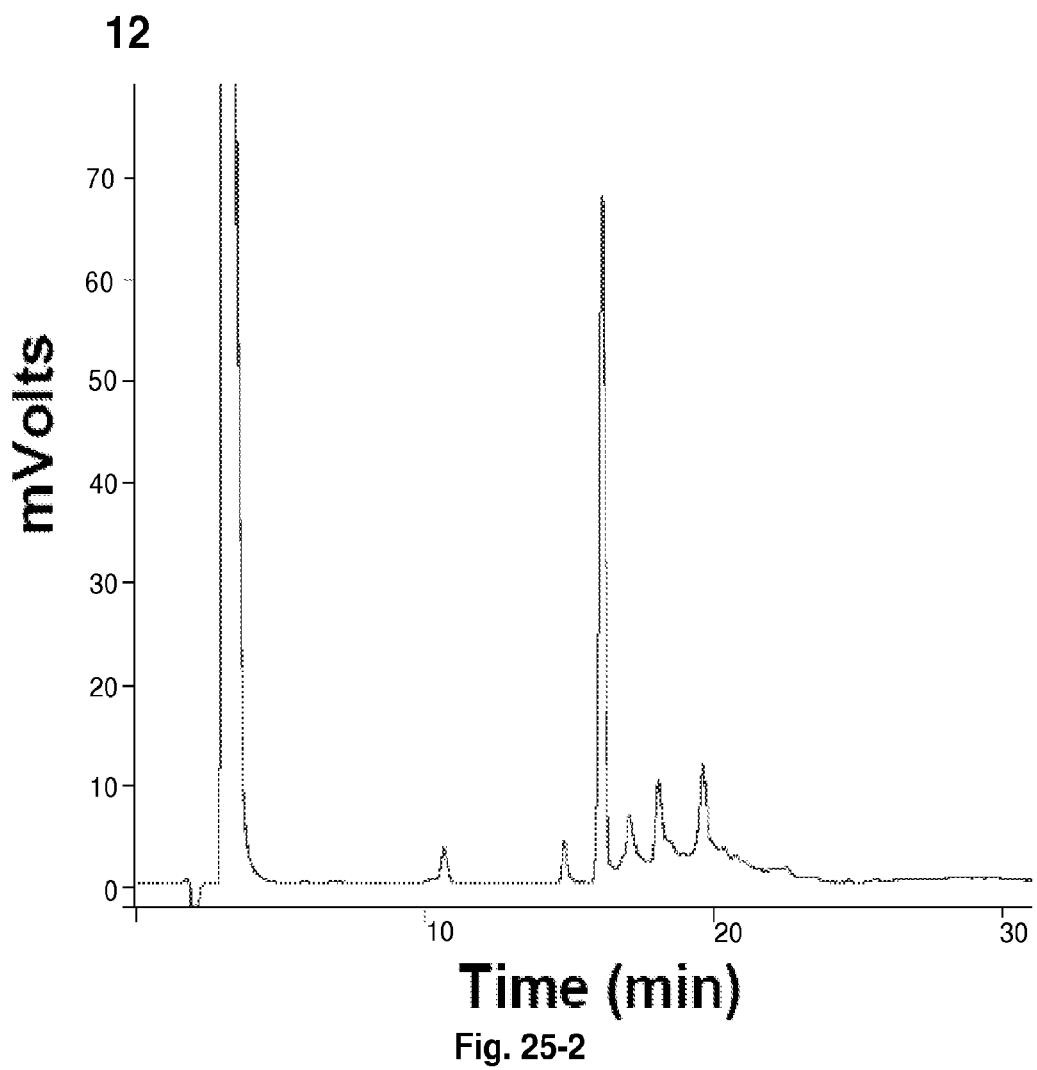

The analysis of the observed c-Myc binding affinities of the bivalent compounds described here shows that derivatives with the linker chain connected to the 5 member ring of the binding moiety derived from 2 have higher affinities than derivatives where the linker is connected to the phenyl ring found within this ligand scaffold. As for modifications of the binding moiety derived from 1,4-aminobenzoic acid derivatives have the highest affinities within the series of different aminobenzoic acid stereoisomers while the 3-substituted compounds the lowest. These observations are, as indicated, in fair agreement with the relative binding affinities of the non-linked scaffold components of each linked compound. Changes in the linker length lead to minor changes in affinity, with the optimal linker size estimated in 5-6 heavy atoms (FIG. 23).

We confirmed that the increased affinity for c-Myc binding of the synthesized inhibitors is indeed a consequence of their bivalent binding to the expected target sites on this protein. NMR and CD experiments provided structural information about the mode of interaction of these compounds with c-Myc and confirmed that upon their binding the flexible nature of the ID target protein is mainly preserved, as previously shown for monovalent binding inhibitors.

The ability of the described bivalent compounds of interfering with c-Myc biological functions was confirmed in vitro in an EMSA assay. The bivalent inhibitors were all superior by orders of magnitude to the monovalent ones in disrupting target DNA binding by c-Myc-Max heterodimers. These compounds were finally tested for growth inhibition of c-Myc over expressing human cancer cell lines HL60 and Burkitt's lymphoma. The observed potencies were strongly encouraging, albeit lower than the direct c-Myc binding affinities of these compounds would have suggested, and their correlation with the latter was incomplete. This likely reflects a combination of factors such as uptake, subcellular distribution and metabolism that have not been studied here. For example, we would note that the molecular weight of each bivalent compound, including its linker, is more than twice that of each parental compound. Moreover, the polar surface of bivalent compounds is quite high. Both of these factors are known to dramatically affect compounds' uptake. The results obtained upon screening of a second group of bivalent compounds with reduced polar surface areas and lower molecular weights support such indication.

Despite the above-cited disparities, we did note that both HL60 cells and BL cells, both of which express extremely high levels of c-Myc, were more sensitive to bivalent compounds than were fibroblasts with normal levels of the protein. This might reflect any one of a number of non-mutually exclusive differences between transformed and non-transformed cells such as differential compound uptake, distribution and metabolism as well as the possibility that both tumor cell lines are "addicted" to c-Myc or have developed "oncogene amnesia" and are therefore unable to tolerate as severe a reduction as are non-transformed cells. HL60 and BL cells might also be formally analogous to those that over-express Topoisomerase I or II, which tend to be more sensitive, rather than less sensitive, to chemotherapeutic agents that target these enzymes.

Overall, the described bivalent compounds displayed strongly enhanced activities compared to the monovalent parent structures, and are promising for further development with therapeutic purposes.

We claim:
1. A compound represented by the formula

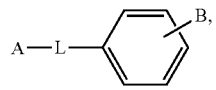

wherein
A is one of a)

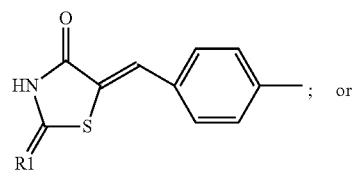

; or b)

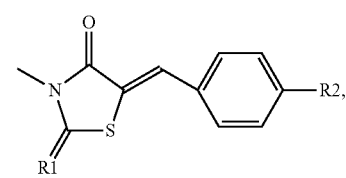

wherein $R_1$ is O or S and $R_2$ is halo or ethyl,
(ii) L is selected from
—$(CH_2)_n$— wherein n is an integer from 1 to 10;
—$[C(O)—NH]_m—[(CH_2)_n—NH—C(O)]_p$—, wherein m is an integer from 0 to 1, n is an integer from 1 to 10, and p is an integer from 1 to 3; or
—$[(CH_2)_m—Ar_n]_p$—, wherein Ar is an aryl group, m is from 1 to 10, n is from 1 to 5, and p is from 1 to 5; and
(iii) B is

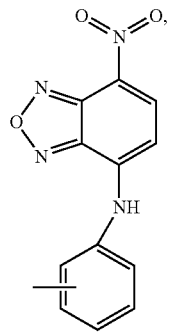

or a pharmaceutically acceptable salt thereof.

2. The compound of claim 1, wherein A represents the structure

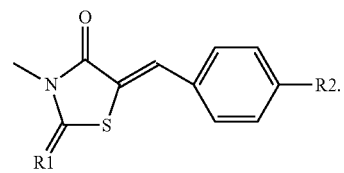

3. The compound of claim 1, wherein A represents the structure

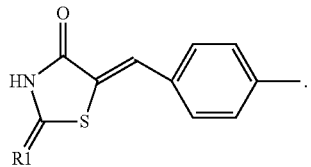

4. The compound of claim 1, wherein A represents the structure

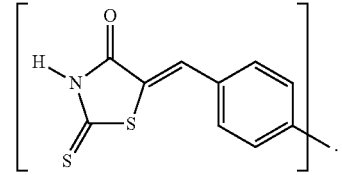

5. The compound of claim 1, wherein A represents the structure:

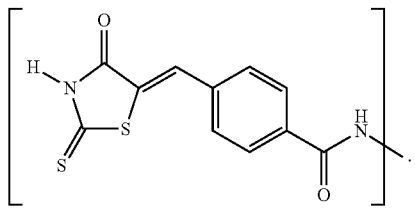

6. The compound of claim 1 in which $R_1$ is S.
7. The compound of claim 1 in which $R_1$ is O.
8. The compound of claim 1 in which $R_2$ is F.
9. The compound of claim 1, wherein L is —$[C(O)—NH]_m—[(CH_2)_n—NH—C(O)]_p$—, m is an integer from 0 to 1, n is an integer from 1 to 6, and p is an integer from 1 to 2.

10. The compound of claim 1 chosen from one of:
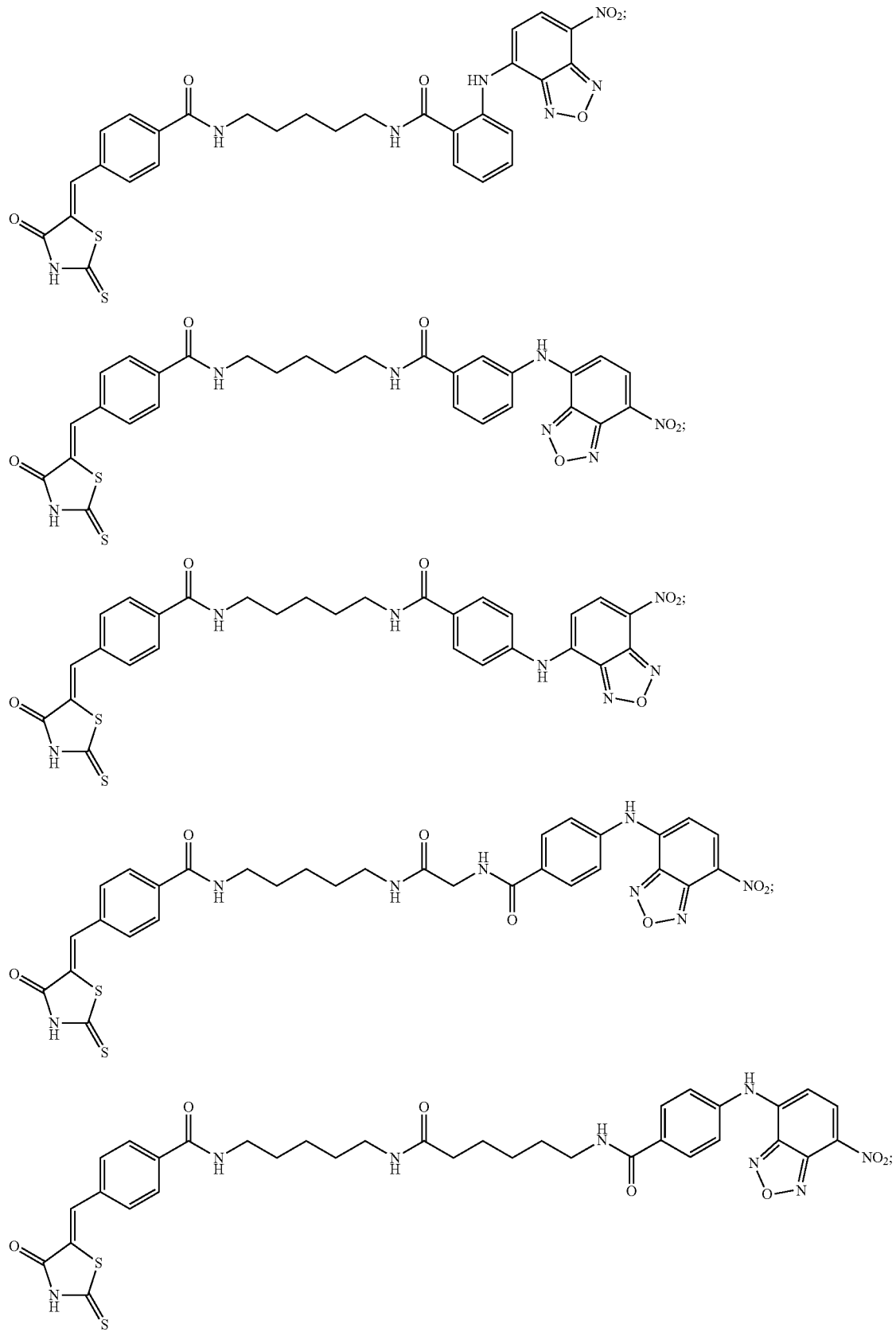

-continued
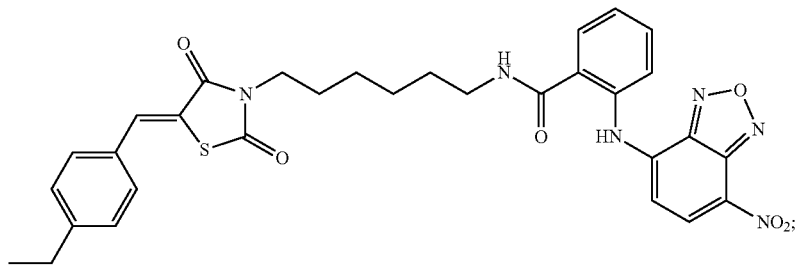
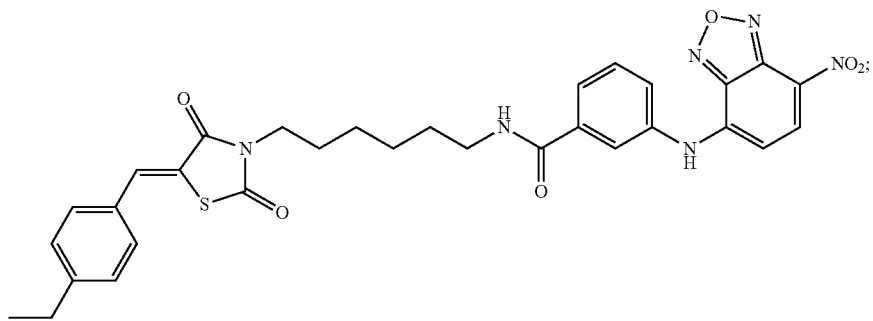
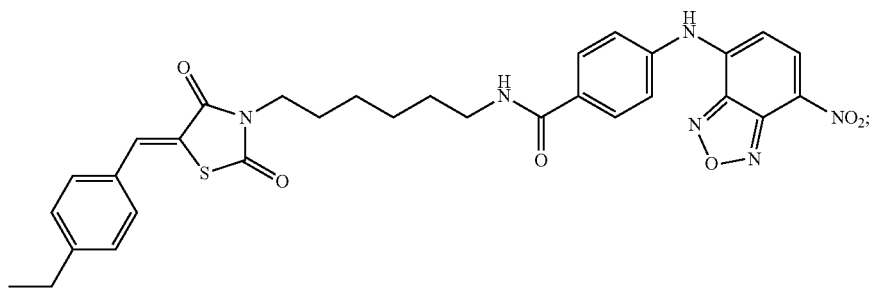
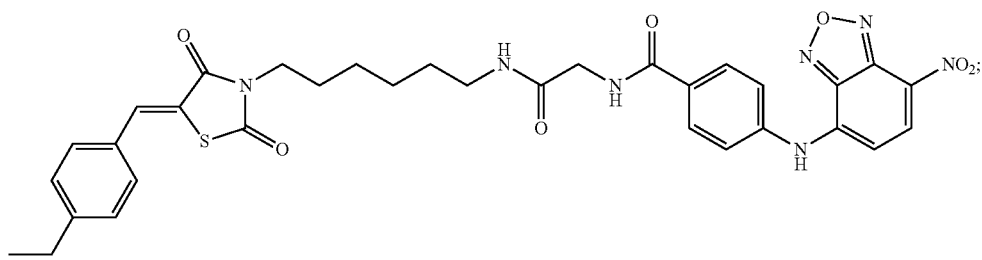
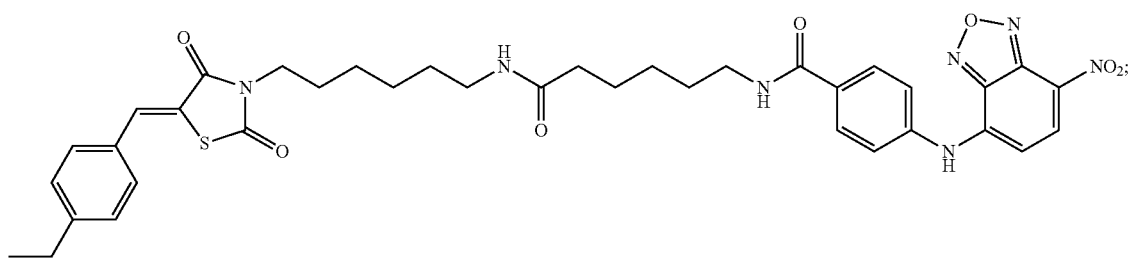
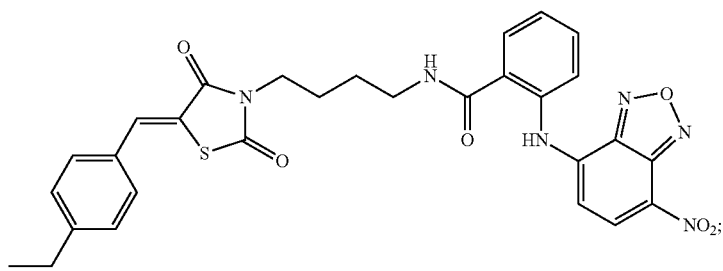

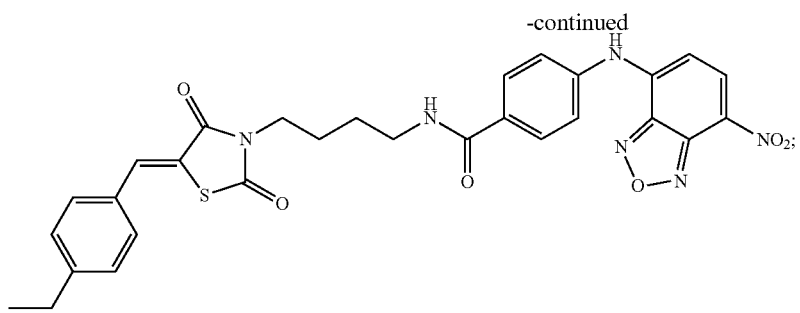

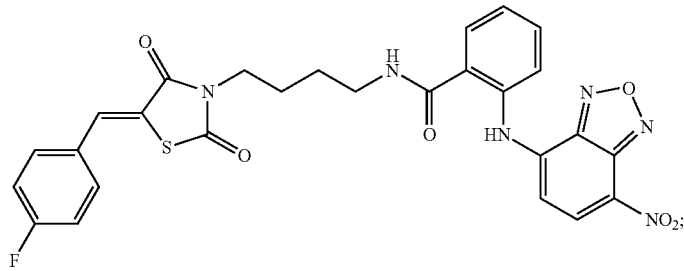

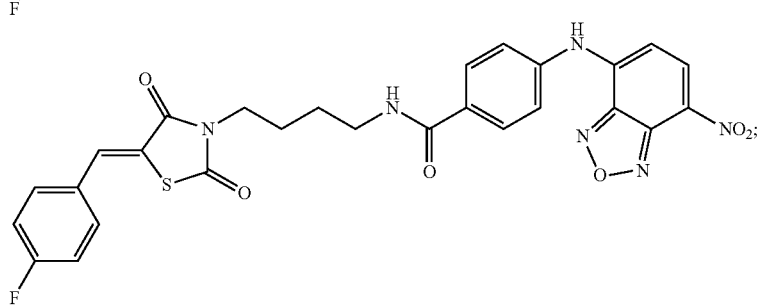

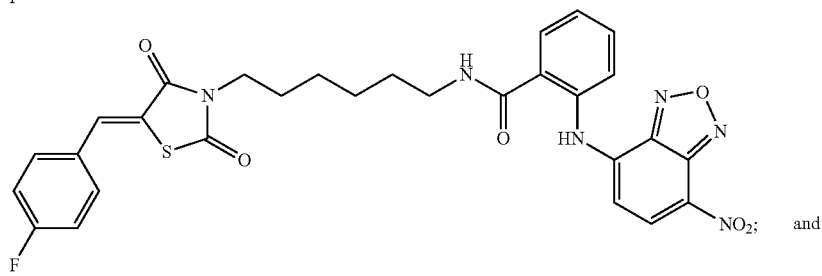

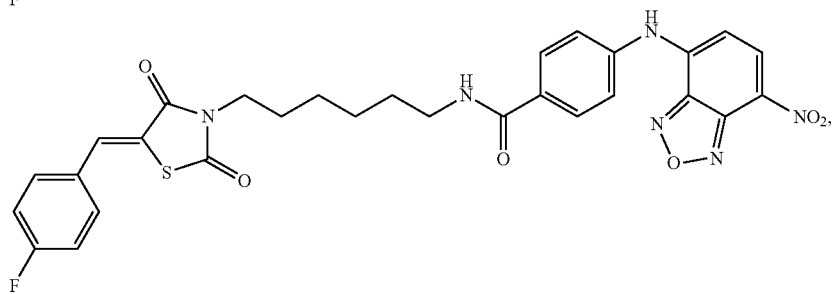

or a pharmaceutically acceptable salt thereof.

11. The compound of claim 1, wherein the compound is a salt of one of an inorganic acid salt, an organic acid salt and a basic salt.

12. The compound of claim 1, wherein the compound is a salt chosen from hydrochloric acid salts, hydrobromic acid salts, phosphoric acid salts, metaphosphoric acid salts, nitric acid salts, sulfuric acid salts, acetic acid salts, benzenesulfonic acid salts, benzoic acid salts, citric acid salts, ethanesulfonic acid salts, fumaric acid salts, gluconic acid salts, glycolic acid salts, isethionic acid salts, lactic acid salts, lactobionic acid salts, maleic acid salts, malic acid salts, methanesulfonic acid salts, succinic acid salts, p-toluenesulfonic acid salts, tartaric acid salts, ammonium salts, alkali metal salts, alkaline earth metal salts, trometamol (2-amino-2-hydroxymethyl-1,3-propanediol) salts, diethanolamine salts, lysine salts or ethylenediamineone salts.

13. A pharmaceutical composition comprising a compound of claim 1, or a pharmaceutically acceptable salt thereof, and a pharmaceutically acceptable excipient.

14. A method of inhibiting growth or proliferation of a cancer cell, comprising contacting the cancer cell with an amount of a compound of claim 1, or a pharmaceutically acceptable salt thereof effective to inhibit growth or proliferation of the cancer cell, wherein the cancer cell is a cell in which interference with c-Myc-Max binding results in decreased growth rate of the cell, and the cancer cell is one of a Burkitt's lymphoma cell; a non-Burkitt's lymphoma cell; a multiple myeloma cell; and a myeloid leukemia cell.

15. A method of inhibiting growth or proliferation of cancer cells in a subject, comprising administering to the subject in need thereof an amount of a compound of claim 1, or a pharmaceutically acceptable salt thereof, in an amount effective to interfere with c-Myc and Max association effective to inhibit growth or proliferation of the cancer cell, and the cancer cell is one of a Burkitt's lymphoma cell; a non-Burkitt's lymphoma cell; a multiple myeloma cell; and a myeloid leukemia cell.

16. The method of claim 15, wherein the cancer cell is a cell in which interference with c-Myc-Max binding, results in decreased growth rate of the cell.

17. The method of claim 15, wherein the cancer cell is a Burkitt's lymphoma cell or a myeloid leukemia cell.

18. The method of claim 15, wherein the compound is

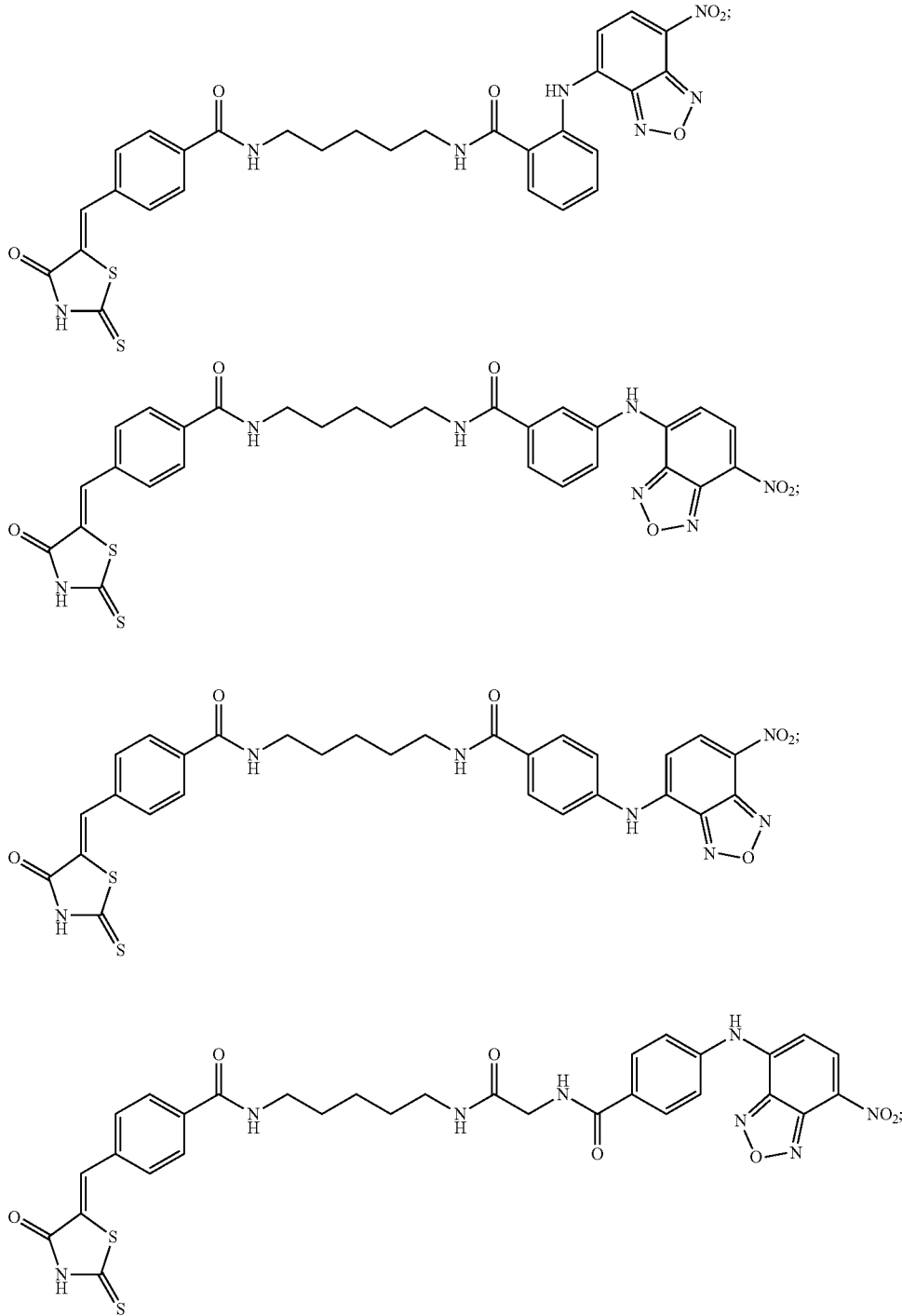

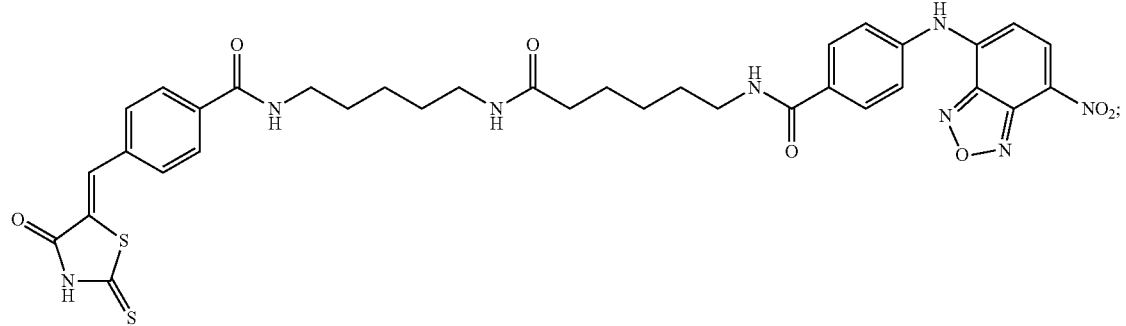
or a pharmaceutically acceptable salt thereof.
* * * * *

UNITED STATES PATENT AND TRADEMARK OFFICE
CERTIFICATE OF CORRECTION

PATENT NO. : 8,637,556 B2  Page 1 of 4
APPLICATION NO. : 13/144674
DATED : January 28, 2014
INVENTOR(S) : Steven J. Metallo et al.

It is certified that error appears in the above-identified patent and that said Letters Patent is hereby corrected as shown below:

In the Claims:

Column 36, line 11, Claim 18 thru Column 38

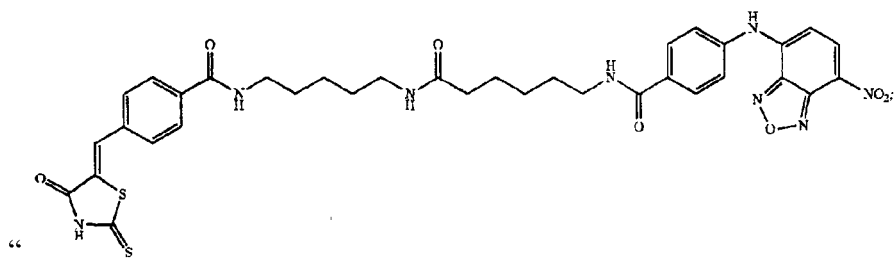

"

or a pharmaceutically acceptable salt thereof."

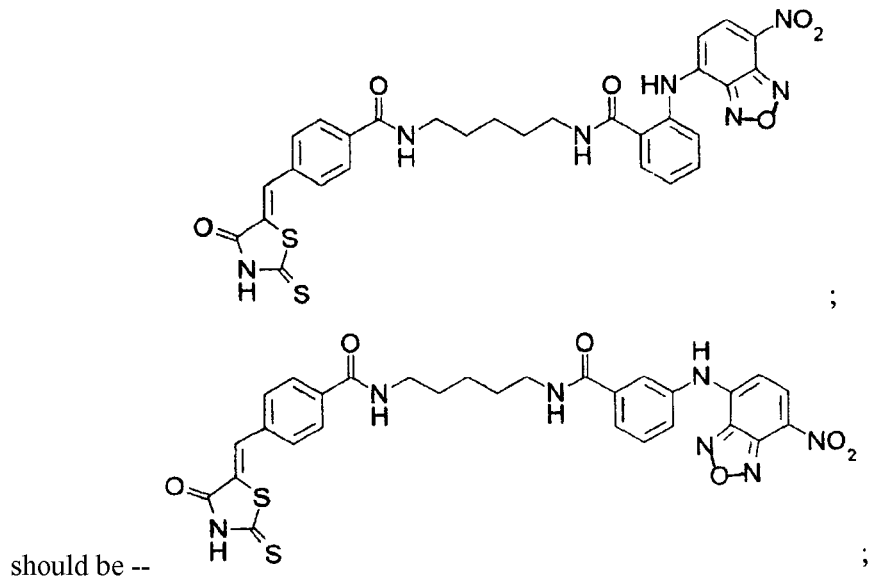

should be --                                                                 ;

Signed and Sealed this
Twenty-ninth Day of September, 2015

Michelle K. Lee
*Director of the United States Patent and Trademark Office*

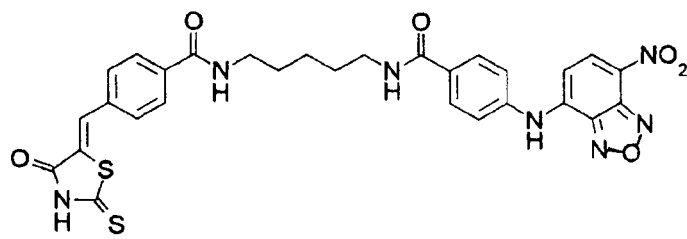
;
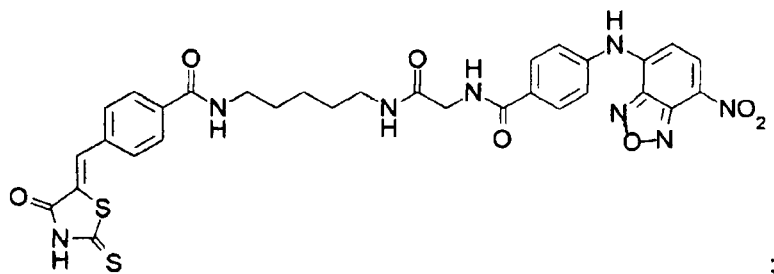
;
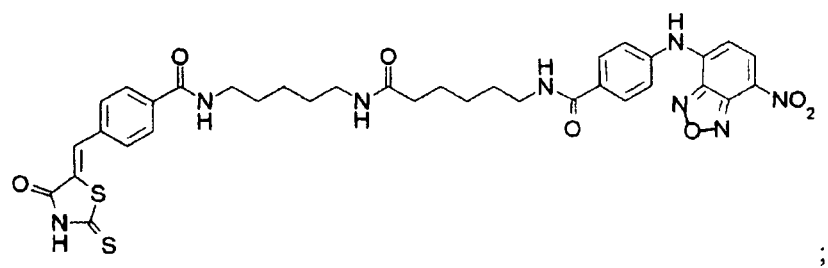
;
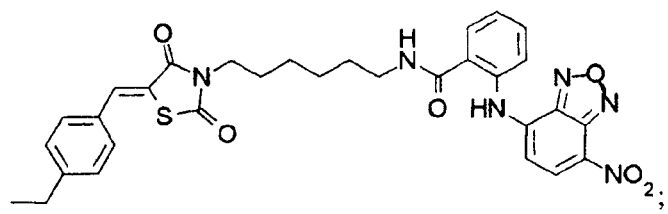
;
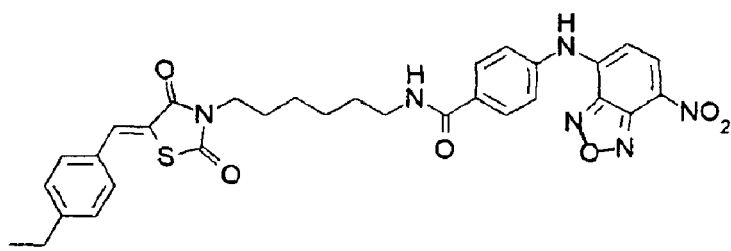
;
;

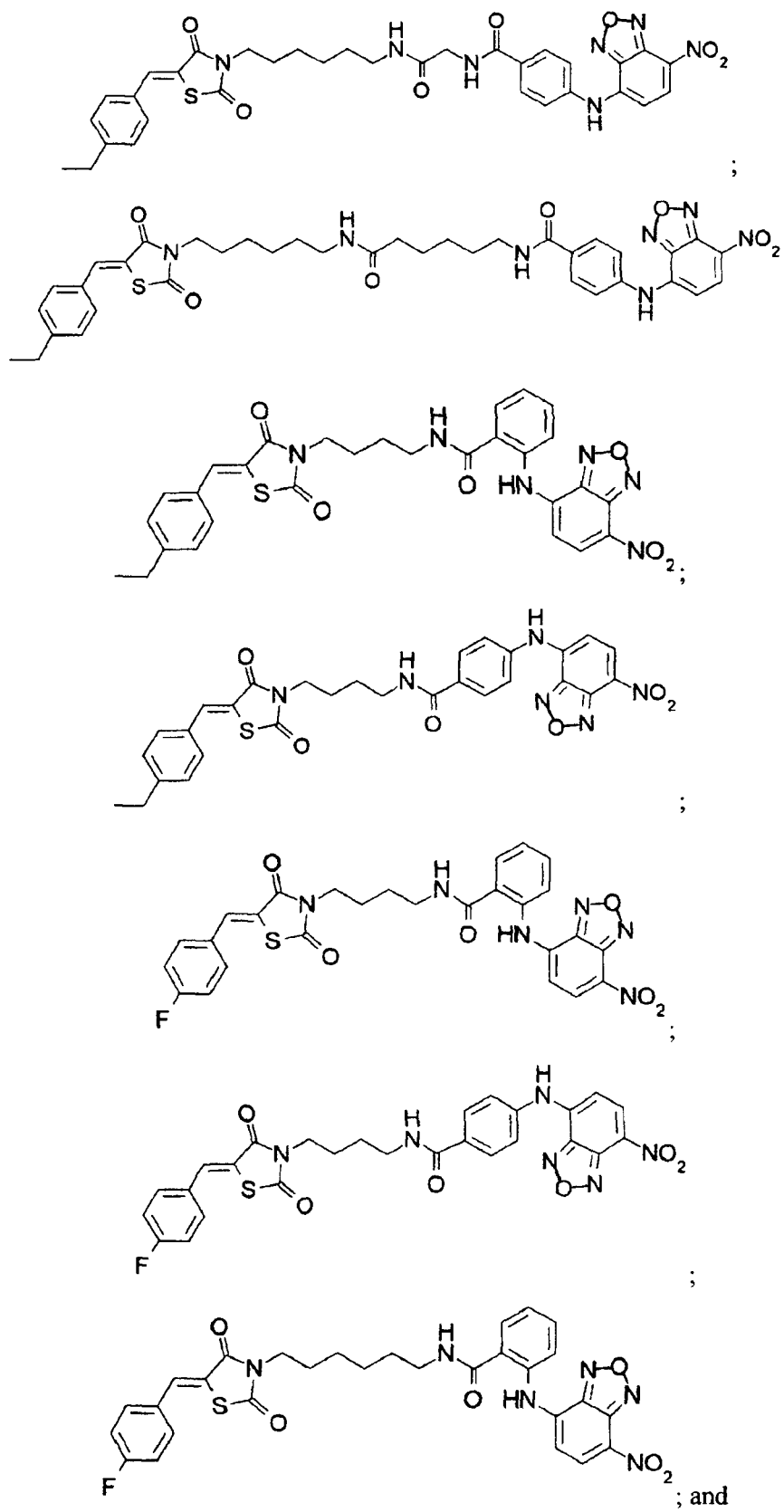

CERTIFICATE OF CORRECTION (continued)
U.S. Pat. No. 8,637,556 B2

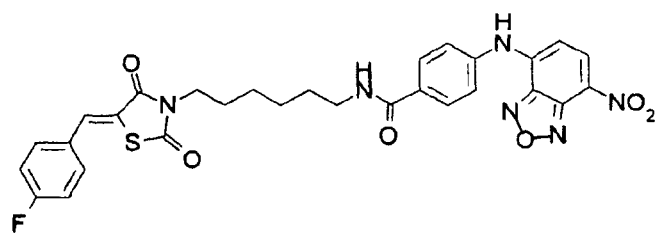

or a pharmaceutically acceptable salt thereof.--

SEQUENCE LISTING

<160> NUMBER OF SEQ ID NOS: 1

<210> SEQ ID NO 1
<211> LENGTH: 454
<212> TYPE: PRT
<213> ORGANISM: Homo sapiens

<400> SEQUENCE: 1

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365
```

```
Val Lys Arg Arg Thr His Asn Val Leu Glu Arg Gln Arg Arg Asn Glu
    370                 375                 380
Leu Lys Arg Ser Phe Phe Ala Leu Arg Asp Gln Ile Pro Glu Leu Glu
385                 390                 395                 400
Asn Asn Glu Lys Ala Pro Lys Val Val Ile Leu Lys Lys Ala Thr Ala
                405                 410                 415
Tyr Ile Leu Ser Val Gln Ala Glu Glu Gln Lys Leu Ile Ser Glu Glu
                420                 425                 430
Asp Leu Leu Arg Lys Arg Arg Glu Gln Leu Lys His Lys Leu Glu Gln
                435                 440                 445
Leu Arg Asn Ser Cys Ala
    450
```